(12) United States Patent
Mauro et al.

(10) Patent No.: US 7,456,273 B2
(45) Date of Patent: Nov. 25, 2008

(54) METHODS OF IDENTIFYING SYNTHETIC TRANSCRIPTIONAL AND TRANSLATIONAL REGULATORY ELEMENTS, AND COMPOSITIONS RELATING TO SAME

(75) Inventors: Vincent P. Mauro, San Diego, CA (US); Gerald M. Edelman, La Jolla, CA (US); Stephen A. Chappell, Del Mar, CA (US); Frederick S. Jones, Cardiff, CA (US); Geoffrey Owens, San Diego, CA (US); Robyn Meech, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 99 days.

(21) Appl. No.: 11/607,131

(22) Filed: Nov. 29, 2006

(65) Prior Publication Data

US 2007/0270580 A1 Nov. 22, 2007

Related U.S. Application Data

(63) Continuation of application No. 10/182,329, filed as application No. PCT/US01/02733 on Jan. 26, 2001, now Pat. No. 7,183,395.

(60) Provisional application No. 60/261,312, filed on Jan. 12, 2001, provisional application No. 60/230,956, filed on Sep. 7, 2000, provisional application No. 60/230,852, filed on Sep. 7, 2000, provisional application No. 60/207,804, filed on May 30, 2000, provisional application No. 60/186,496, filed on Mar. 2, 2000, provisional application No. 60/178,816, filed on Jan. 28, 2000.

(51) Int. Cl.
C07H 21/04 (2006.01)
C07H 21/02 (2006.01)
C12Q 1/68 (2006.01)

(52) U.S. Cl. .................. 536/24.1; 536/23.1; 435/6
(58) Field of Classification Search ............... None
See application file for complete search history.

(56) References Cited

U.S. PATENT DOCUMENTS 5,686,120 A 11/1997 Mertz et al. ............ 435/320.1

FOREIGN PATENT DOCUMENTS

| WO | WO 94/24870 | 11/1994 |
|----|----|----|
| WO | WO 99/02719 | 1/1999 |
| WO | WO 99/25817 | 5/1999 |

Primary Examiner—Teresa E Strzelecka
(74) Attorney, Agent, or Firm—DLA Piper LLP (US)

(57) ABSTRACT

Provided are methods of identifying oligonucleotides having transcriptional or translational activity by integrating ilie oligonucleotide into a eukaryotic cell genome such that the oligonucleotide is operatively linked to an expressible polynucleotide, and detecting a change in expression of the expressible polynucleotide due to the operatively linked oligonucleotide. Also provided are vectors useful for identifying an oligonucleotide having transcriptional or translational regulatory activity according to a method of the invention. In addition, isolated synthetic transcriptional or translational regulatory elements identified according to a method of the invention are provided, as are kits, which contain a vector useful for identifying a transcriptional or translational regulatory element, or an isolated synthetic transcriptional or translational regulatory element or plurality of such elements. Also provided are isolated transcriptional regulatory elements.

5 Claims, 5 Drawing Sheets

| | | |
|---|---|---|
| YAP1 (87–96) | ACGAGCCAUU | (90) |
| | \| \|\|\|\|\|\|\|\| | |
| 18S (101–92) | UACUCGGUAA | (91) |
| YAP1 (142–127) | CCCAAAACGUUUAAAG | (92) |
| | \|\|\|\| \|\|\|\|\|\|◦ \|\|\| | |
| 18S (1453–1438) | GGGUCUUGCAAGAUUC | (93) |

---

| | | |
|---|---|---|
| p150 (110–122) | CAGACUUCCAUCG | (94) |
| | \|\|◦\|\|\|\|\|\|\|\|\| | |
| 18S (1413–1401) | GUUUGAAGGUAGC | (95) |
| p150 (145–163) | GCGCUAUCCUCAUCGCGAC | (96) |
| | \|\| \|\|\|\|\|\|◦\|\| \|◦\|\|\|\| | |
| 18S (1547–1529) | CGAGAUAGGGGUCGUGCUG | (97) |
| p150 (403–417) | UUAUGAUUCUUCCUC | (98) |
| | \| \|\|\|\|\|◦\|\|\|\|\| \| | |
| 18S (1798–1784) | AUUACUAGGAAGGCG | (99) |
| p150 (417–441) | CUUCCUUCAAUUUCUUAAAGCUUC | (100) |
| | \|◦\| \|\| \|\|\|\|\|\|\|◦\|\|\| \|\|\| \|\|\| | |
| 18S (1151–1127) | GGAAGGCAGUUAAGGAAAUUCAAAG | (101) |

SEQUENCE LISTING

<160> NUMBER OF SEQ ID NOS: 112

<210> SEQ ID NO 1
<211> LENGTH: 6279
<212> TYPE: DNA
<213> ORGANISM: Artificial sequence
<220> FEATURE:
<223> OTHER INFORMATION: vector

<400> SEQUENCE: 1

```
gaattctcat gtttgacagc ttatcatcga ttagtccaat ttgttaaaga caggatatca      60
gtggtccagg ctcagttttg actcaacaat atcaccagct gaagcctata gagtacgagc     120
catagataga ataaaagatt ttatttagtc tccagaaaaa gggggaatg aaagacccca      180
cctgtaggtt tggcaagcta gaaatgtagt cttatgcaat acacttgtag tcttgcaaca     240
tggtaacgat gagttagcaa catgccttac aaggagagaa aaagcaccgt gcatgccgat     300
tggtggaagt aaggtggtac gatcgtgcct tattaggaag gcaacagaca ggtctgacat     360
ggattggacg aaccactcta gagaaccatc agatgtttcc agggtgcccc aaggacctga     420
aaatgaccct gtgccttatt tgaactaacc aatcagttcg cttctcgctt ctgttcgcgc     480
gcttctgctc cccgagctca ataaaagagc ccacaacccc tcactcggcg cgccagtcct     540
ccgattgact cgctcgcccg ggtacccgta ttcccaataa agcctcttgc tgtttgcatc     600
cgaatcgtgg actcgctgat ccttgggagg gtctcctcag attgattgac tgcccacctc     660
ggggtctttc atttggaggt tccaccgaga tttggagacc ccagcccagg gaccaccgac     720
ccccccgccg ggaggtaagc tggccagcgg tcgtttcgtg tctgtctctg tctttgtgcg     780
tgtttgtgcc ggcatctaat gtttgcgcct gcgtctgtac tagttagcta actagctctg     840
tatctggcgg acccgtggtg gaactgacga gttctgaaca cccggccgca accctgggag     900
acgtcccagg gactttgggg ccgtttttg tggcccgacc tgaggaaggg agtcgatgtg      960
gaatccgacc ccgtcaggat atgtggttct ggtaggagag gagaacctaa aacagttccc    1020
gcctccgtct gaattttgc tttcggtttg gaaccgaagc cgcgcgtctt gtctgctgca     1080
gcatcgttct gtgttgtctc tgtctgactg tgtttctgta tttgtctgaa aattagggcc    1140
agactgttac cactcccta agtttgacct taggtcactg gaaagatgtc gagcggatcg     1200
ctcacaacca gtcggtagat gtcaagaaga gacgttgggt taccttctgc tctgcagaat    1260
ggccaacctt taacgtcgga tggccgcgag acggcacctt taaccgagac ctcatcaccc    1320
aggttaagat caaggtcttt cacctggccc gcatggacac ccagaccagg tcccctacat    1380
cgtgacctgg gaagccttgg cttttgaccc ccctccctgg gtcaagccct tgtacacccc    1440
taagcctccg cctcctcttc ctccatccgc ccgtctctc ccccttgaac ctcctcgttc     1500
gaccccgcct cgatcctccc tttatccagc cctcactcct tctctaggcg ccggaattcg    1560
ttcatggtga gcaagggcga ggagctgttc accggggtgg tgcccatcct ggtcgagctg    1620
gacggcgacg taaacggcca caagttcagc gtgtccggcg agggcgaggg cgatgccacc    1680
tacggcaagc tgaccctgaa gttcatctgc accaccggca agctgcccgt gccctggccc    1740
accctcgtga ccaccctgac ctacggcgtg cagtgcttca gccgctaccc cgaccacatg    1800
aagcagcacg acttcttcaa gtccgccatg cccgaaggct acgtccagga gcgcaccatc    1860
ttcttcaagg acgacggcaa ctacaagacc cgcgccgagg tgaagttcga gggcgacacc    1920
ctggtgaacc gcatcgagct gaagggcatc gacttcaagg aggacggcaa catcctgggg    1980
cacaagctgg agtacaacta caacagccac aacgtctata tcatggccga caagcagaag    2040
aacggcatca aggccaactt caagacccgc cacaacatcg aggacggcgg cgtgcagctc    2100
gccgaccact accagcagaa cacccccatc ggcgacggcc ccgtgctgct gcccgacaac    2160
cactacctga gcacccagtc cgccctgagc aaagacccca acgagaagcg cgatcacatg    2220
gtcctgctgg agttcgtgac cgccgccggg atcactctcg gcatggacga gctgtacaag    2280
```

```
taaagcggcc gcgactctag agtcgaggat cctctagagg aattcccgcc cctctccctc    2340
cccccccct  aacgttactg gccgaagccg cttggaataa ggccggtgtg cgtttgtcta    2400
tatgttattt tccaccatat tgccgtcttt tggcaatgtg agggcccgga aacctggccc    2460
tgtcttcttg acgagcattc ctaggggtct ttcccctctc gccaaaggaa tgcaaggtct    2520
gttgaatgtc gtgaaggaag cagttcctct ggaagcttct tgaagacaaa caacgtctgt    2580
agcgaccctt tgcaggcagc ggaaccccc  acctggcgac aggtgcctct gcggccaaaa    2640
gccacgtgta taagatacac ctgcaaaggc ggcacaaccc cagtgccacg ttgtgagttg    2700
gatagttgtg gaaagagtca aatggctctc ctcaagcgta ttcaacaagg ggctgaagga    2760
tgcccagaag gtaccccatt gtatgggatc tgatctgggg cctcggtgca catgctttac    2820
atgtgtttag tcgaggttaa aaaaacgtct aggccccccg aaccacgggg acgtggtttt    2880
cctttgaaaa acacgatgat aagcttgcca caacccacaa ggagacgacc ttccatgacc    2940
gagtacaagc ccacggtgcg cctcgccacc cgcgacgacg tccccgggc  cgtacgcacc    3000
ctcgccgccg cgttcgccga ctaccccgcc acgcgccaca ccgtcgaccc ggaccgccac    3060
atcgagcggg tcaccgagct gcaagaactc ttcctcacgc gcgtcgggct cgacatcggc    3120
aaggtgtggg tcgcggacga cggcgccgcg gtggcggtct ggaccacgcc ggagagcgtc    3180
gaagcggggg cggtgttcgc cgagatcggc ccgcgcatgg ccgagttgag cggttcccgg    3240
ctggccgcgc agcaacagat ggaaggcctc ctggcgccgc accggcccaa ggagcccgcg    3300
tggttcctgg ccaccgtcgg cgtctcgccc gaccaccagg gcaagggtct gggcagcgcc    3360
gtcgtgctcc ccggagtgga ggcggccgag cgcgccgggg tgcccgcctt cctggagacc    3420
tccgcgcccc gcaacctccc cttctacgag cggctcggct tcaccgtcac cgccgacgtc    3480
gagtgcccga aggaccgcgc gacctggtgc atgacccgca agcccggtgc ctgacgcccg    3540
ccccacgacc cgcagcgccc gaccgaaagg agcgcacgac cccatgtcga cggtatcgat    3600
aaaataaaag attttatttta gtctccagaa aaaggggggaa atgaaagacc ccacctgtag    3660
gtttggcaag ctagacatgc atcgacgcgt gaagatctga aggggggcta taaaagcgat    3720
ggatccgagc tcggccctca ttctggagac tctagaggcc ttgaattcgc ggccgcgcca    3780
gtcctccgat tgactgcgtc gcccgggtac cgtgtatcca ataaaccctc ttgcagttgc    3840
atccgacttg tggtctcgct gttccttggg agggtctcct ctgagtgatt gactacccgt    3900
cagcggggt  ctttcatttg ggggctcgtc cgggatcggg agaccctgc  ccagggacca    3960
ccgacccacc accgggaggt aagctggctg cctcgcgcgt ttcggtgatg acggtgaaaa    4020
cctctgacac atgcagctcc cggagacggt cacagcttgt ctgtaagcgg atgccgggag    4080
cagacaagcc cgtcagggcg cgtcagcggg tgttggcggg tgtcggggcg cagccatgac    4140
ccagtcacgt agcgatagcg gagtgtatac tggcttaact atgcggcatc agagcagatt    4200
gtactgagag tgcaccatat gcggtgtgaa ataccgcaca gatgcgtaag gagaaaatac    4260
cgcatcaggc gctcttccgc ttcctcgctc actgactcgc tgcgctcggt cgttcggctg    4320
cggcgagcgg tatcagctca ctcaaaggcg gtaatacggt tatccacaga atcagggggat    4380
aacgcaggaa agaacatgtg agcaaaaggc cagcaaaagg ccaggaaccg taaaaaggcc    4440
gcgttgctgg cgtttttcca taggctccgc cccctgacg  agcatcacaa aaatcgacgc    4500
tcaagtcaga ggtggcgaaa cccgacagga ctataaagat accaggcgtt ccccctgga    4560
agctccctcg tgcgctctcc tgttccgacc ctgccgctta ccggatacct gtccgccttt    4620
ctcccttcgg gaagcgtggc gctttctcat agctcacgct gtaggtatct cagttcggtg    4680
```

```
taggtcgttc gctccaagct gggctgtgtg cacgaacccc ccgttcagcc cgaccgctgc    4740
gccttatccg gtaactatcg tcttgagtcc aacccggtaa gacacgactt atcgccactg    4800
gcagcagcca ctggtaacag gattagcaga gcgaggtatg taggcggtgc tacagagttc    4860
ttgaagtggt ggcctaacta cggctacact agaaggacag tatttggtat ctgcgctctg    4920
ctgaagccag ttaccttcgg aaaaagagtt ggtagctctt gatccggcaa acaaaccacc    4980
gctggtagcg gtggtttttt tgtttgcaag cagcagatta cgcgcagaaa aaaggatct    5040 caagaagatc ctttgatctt ttctacgggg tctgacgctc agtggaacga aaactcacgt    5100
taagggattt tggtcatgag attatcaaaa aggatcttca cctagatcct tttaaattaa    5160
aaatgaagtt ttaaatcaat ctaaagtata tatgagtaaa cttggtctga cagttaccaa    5220
tgcttaatca gtgaggcacc tatctcagcg atctgtctat ttcgttcatc catagttgcc    5280 tgactcccccg tcgtgtagat aactacgata cgggagggct taccatctgg ccccagtgct    5340
gcaatgatac cgcgagaccc acgctcaccg gctccagatt tatcagcaat aaaccagcca    5400
gccggaaggg ccgagcgcag aagtggtcct gcaactttat ccgcctccat ccagtctatt    5460
aattgttgcc gggaagctag agtaagtagt tcgccagtta atagtttgcg caacgttgtt    5520
gccattgctg caggcatcgt ggtgtcacgc tcgtcgtttg gtatggcttc attcagctcc    5580
ggttcccaac gatcaaggcg agttacatga tcccccatgt tgtgcaaaaa agcggttagc    5640
tccttcggtc ctccgatcgt tgtcagaagt aagttggccg cagtgttatc actcatggtt    5700
atggcagcac tgcataattc tcttactgtc atgccatccg taagatgctt ttctgtgact    5760
ggtgagtact caaccaagtc attctgagaa tagtgtatgc ggcgaccgag ttgctcttgc    5820
ccggcgtcaa cacgggataa taccgcgcca catagcagaa ctttaaaagt gctcatcatt    5880
ggaaaacgtt cttcggggcg aaaactctca aggatcttac cgctgttgag atccagttcg    5940
atgtaaccca ctcgtgcacc caactgatct tcagcatctt ttactttcac cagcgtttct    6000
gggtgagcaa aaacaggaag gcaaaatgcc gcaaaaaagg gaataagggc gacacggaaa    6060
tgttgaatac tcatactctt cctttttcaa tattattgaa gcatttatca gggttattgt    6120
ctcatgagcg gatacatatt tgaatgtatt tagaaaaata aacaaatagg ggttccgcgc    6180
acatttcccc gaaaagtgcc acctgacgtc taagaaacca ttattatcat gacattaacc    6240
tataaaaata ggcgtatcac gaggcccttt cgtcttcaa                           6279
```

<210> SEQ ID NO 2
<211> LENGTH: 3404
<212> TYPE: DNA
<213> ORGANISM: Artificial sequence
<220> FEATURE:
<223> OTHER INFORMATION: vector

<400> SEQUENCE: 2

```
ctcgagatct gtaatacgac tcactatagg gctgcaggaa acagctatga ccatgatatc      60
atagcggccg cagatctggc gattgggggcg cgcgcgcctc cttcggtttg gggctaatta    120
taaagtggct ccagcagccg ttaagccccg ggacggcgag gcaggcgctc agagccccgc    180
agcctggccc gtgaccccgc agagacgctg aggaagcttc catggccaag ttgaccagtg    240
ccgttccggt gctcaccgcg cgcgacgtcg ccggagcggt cgagttctgg accgaccggc    300
tcgggttctc ccgggacttc gtggaggacg acttcgccgg tgtggtccgg gacgacgtga    360
ccctgttcat cagcgcggtc caggaccagg tggtgccgga caacaccctg gcctgggtgt    420
```

```
gggtgcgcgg cctggacgag ctgtacgccg agtggtcgga ggtcgtgtcc acgaacttcc      480
gggacgcctc cgggccggcc atgaccgaga tcggcgagca gccgtggggg cgggagttcg      540
ccctgcgcga cccggccggc aactgcgtgc acttcgtggc cgaggagcag gactgacact      600
cgacctcgaa acttgtttat tgcagcttat aatggttaca aataaagcaa tagcatcaca      660
aatttcacaa ataaagcatt tttttcactg cattctagtt gtggtttgtc caaactcatc      720
aatgtatctt atcatgtctg gatccgtcga cgtcaggtgg cacttttcgg ggaaatgtgc      780
gcggaacccc tatttgttta tttttctaaa tacattcaaa tatgtatccg ctcatgagac      840
aataaccctg ataaatgctt caataatatt gaaaaggaa gagtcctgag gcggaaagaa       900
ccagctgtgg aatgtgtgtc agttagggtg tggaaagtcc ccaggctccc cagcaggcag      960
aagtatgcaa agcatgcatc tcaattagtc agcaaccagg tgtggaaagt ccccaggctc      1020
cccagcaggc agaagtatgc aaagcatgca tctcaattag tcagcaacca tagtcccgcc      1080
cctaactccg cccatcccgc ccctaactcc gcccagttcc gcccattctc cgccccatgg      1140
ctgactaatt ttttttattt atgcagaggc cgaggccgcc tcggcctctg agctattcca      1200
gaagtagtga ggaggctttt ttggaggcct aggcttttgc aaagatcgat caagagacag      1260
gatgaggatc gtttcgcatg attgaacaag atggattgca cgcaggttct ccggccgctt      1320
gggtggagag gctattcggc tatgactggg cacaacagac aatcggctgc tctgatgccg      1380
ccgtgttccg gctgtcagcg caggggcgcc cggttctttt tgtcaagacc gacctgtccg      1440
gtgccctgaa tgaactgcaa gacgaggcag cgcggctatc gtggctggcc acgacgggcg      1500
ttccttgcgc agctgtgctc gacgttgtca ctgaagcggg aagggactgg ctgctattgg      1560
gcgaagtgcc ggggcaggat ctcctgtcat ctcaccttgc tcctgccgag aaagtatcca      1620
tcatggctga tgcaatgcgg cggctgcata cgcttgatcc ggctacctgc ccattcgacc      1680
accaagcgaa acatcgcatc gagcgagcac gtactcggat ggaagccggt cttgtcgatc      1740
aggatgatct ggacgaagag catcaggggc tcgcgccagc cgaactgttc gccaggctca      1800
aggcgagcat gcccgacggc gaggatctcg tcgtgaccca tggcgatgcc tgcttgccga      1860
atatcatggt ggaaaatggc cgcttttctg gattcatcga ctgtggccgg ctgggtgtgg      1920
cggaccgcta tcaggacata gcgttggcta cccgtgatat tgctgaagag cttggcggcg      1980
aatgggctga ccgcttcctc gtgctttacg gtatcgccgc tcccgattcg cagcgcatcg      2040
ccttctatcg ccttcttgac gagttcttct gagcgggact ctggggttcg aaatgaccga      2100
ccaagcgacg cccaacctgc catcacgaga tttcgattcc accgccgcct tctatgaaag      2160
gttgggcttc ggaatcgttt tccgggacgc cggctggatg atcctccagc gcgggatct       2220 catgctggag ttcttcgccc acccctagggg gaggctaact gaaacacgga aggagacaat      2280
accggaagga acccgcgcta tgacggcaat aaaaagacag aataaaacgc acggtgttgg      2340
gtcgtttgtt cataaacgcg gggttcggtc ccagggctgg cactctgtcg ataccccacc      2400
gagaccccat tggggccaat acgcccgcgt ttcttccttt tccccacccc acccccaag       2460 ttcgggtgaa ggcccagggc tcgcagccaa cgtcggggcg gcaggccctg ccatagcctc      2520
aggatgctac gttctagacg tcaggttact catatatact ttagattgat ttaaaacttc      2580 attttaatt taaaggatc taggtgaaga tccttttga taatctcatg accaaaatcc         2640
cttaacgtga gttttcgttc cactgagcgt cagacccgt agaaaagatc aaaggatctt       2700
cttgagatcc ttttttctg cgcgtaatct gctgcttgca acaaaaaaa ccaccgctac        2760 cagcggtggt ttgtttgccg gatcaagagc taccaactct ttttccgaag gtaactggct      2820
```

```
tcagcagagc gcagatacca aatactgtcc ttctagtgta gccgtagtta ggccaccact   2880
tcaagaactc tgtagcaccg cctacatacc tcgctctgct aatcctgtta ccagtggctg   2940
ctgccagtgg cgataagtcg tgtcttaccg ggttggactc aagacgatag ttaccggata   3000
aggcgcagcg gtcgggctga acgggggggtt cgtgcacaca gcccagcttg agcgaacga   3060 cctacaccga actgagatac ctacagcgtg agctatgaga aagcgccacg cttcccgaag   3120
ggagaaaggc ggacaggtat ccggtaagcg gcagggtcgg aacaggagag cgcacgaggg   3180
agcttccagg gggaaacgcc tggtatcttt atagtcctgt cgggtttcgc cacctctgac   3240
ttgagcgtcg attttttgtga tgctcgtcag gggggcggag cctatggaaa aacgccagca   3300
acgcggcctt tttacggttc ctggccttt gctggccttt tgctcacatg ttctttcctg   3360
cgttatcccc tgattctgtg ataaccgta ttaccgccat gcat              3404

<210> SEQ ID NO 3
<211> LENGTH: 4152
<212> TYPE: DNA
<213> ORGANISM: Artificial sequence
<220> FEATURE:
<223> OTHER INFORMATION: vector

<400> SEQUENCE: 3
ctcgagatct gtaatacgac tcactatagg gctgcaggaa acagctatga ccatgatatc    60
atagcggccg cagatctggc gattggggcg cgcgcgcctc cttcggtttg gggctaatta   120
taaagtggct ccagcagccg ttaagccccg ggacggcgag gcaggcgctc agagcccgc    180 agcctggccc gtgaccccgc agagacgctg aggaagctta tatgaaaaag cctgaactca   240
ccgcgacgtc tgtcgagaag tttctgatcg aaaagttcga cagcgtctcc gacctgatgc   300
agctctcgga gggcgaagaa tctcgtgctt tcagcttcga tgtaggaggg cgtggatatg   360
tcctgcgggt aaatagctgc gccgatggtt tctacaaaga tcgttatgtt tatcggcact   420
ttgcatcggc cgcgctcccg attccggaag tgcttgacat tggggaattc agcgagagcc   480
tgacctattg catctcccgc cgtgcacagg gtgtcacgtt gcaagacctg cctgaaaccg   540
aactgcccgc tgttctgcag ccggtcgcgg aggccatgga tgcgatcgct gcggccgatc   600
ttagccagac gagcgggttc ggcccattcg gaccgcaagg aatcggtcaa tacactacat   660
ggcgtgattt catatgcgcg attgctgatc cccatgtgta tcactggcaa actgtgatgg   720
acgacaccgt cagtgcgtcc gtcgcgcagg ctctcgatga gctgatgctt tgggccgagg   780
actgccccga agtccggcac ctcgtgcacg cggatttcgg ctccaacaat gtcctgacgg   840
acaatggccg cataacagcg gtcattgact ggagcgaggc gatgttcggg gattcccaat   900
acgaggtcgc caacatcttc ttctggaggc cgtggttggc ttgtatggag cagcagacgc   960
gctacttcga gcggaggcat ccggagcttg caggatcgcc gcggctccgg gcgtatatgc  1020
tccgcattgg tcttgaccaa ctctatcaga gcttggttga cggcaatttc gatgatgcag  1080
cttgggcgca gggtcgatgc gacgcaatcg tccgatccgg agccgggact gtcgggcgta  1140
cacaaatcgc ccgcagaagc gcggccgtct ggaccgatgg ctgtgtagaa gtactcgccg  1200
atagtggaaa ccgacgcccc agcactcgtg gggatcggga gatgggggag ctaactgaa   1260 acacggaagg agacaatacc ggaaggaacc cgcgctatga cggcaataaa aagacagaat  1320
aaaacgcacg gtgttgggt cgtttgttca taaacgcggg gttcggtccc agggctggca  1380
ctctgtcgat accccaccga gaccccattg gggccaatac gcccgcgttt cttccttttc  1440
```

-continued

```
cccaccccaa cccccaagtt cgggtgaagg cccagggctc gcagccaacg tcggtcgacg    1500
tcaggtggca cttttcgggg aaatgtgcgc ggaaccccta tttgtttatt tttctaaata    1560
cattcaaata tgtatccgct catgagacaa taaccctgat aaatgcttca ataatattga    1620
aaaaggaaga gtcctgaggc ggaaagaacc agctgtggaa tgtgtgtcag ttagggtgtg    1680
gaaagtcccc aggctcccca gcaggcagaa gtatgcaaag catgcatctc aattagtcag    1740
caaccaggtg tggaaagtcc ccaggctccc cagcaggcag aagtatgcaa agcatgcatc    1800
tcaattagtc agcaaccata gtcccgcccc taactccgcc catcccgccc ctaactccgc    1860
ccagttccgc ccattctccg ccccatggct gactaatttt ttttatttat gcagaggccg    1920
aggccgcctc ggcctctgag ctattccaga agtagtgagg aggcttttt  ggaggcctag    1980 gcttttgcaa agatcgatca agagacagga tgaggatcgt ttcgcatgat tgaacaagat    2040
ggattgcacg caggttctcc ggccgcttgg gtggagaggc tattcggcta tgactgggca    2100
caacagacaa tcggctgctc tgatgccgcc gtgttccggc tgtcagcgca ggggcgcccg    2160 gttcttttg  tcaagaccga cctgtccggt gccctgaatg aactgcaaga cgaggcagcg    2220
cggctatcgt ggctggccac gacgggcgtt ccttgcgcag ctgtgctcga cgttgtcact    2280
gaagcgggaa gggactggct gctattgggc gaagtgccgg ggcaggatct cctgtcatct    2340
caccttgctc ctgccgagaa agtatccatc atggctgatg caatgcggcg gctgcatacg    2400
cttgatccgg ctacctgccc attcgaccac caagcgaaac atcgcatcga gcgagcacgt    2460
actcggatgg aagccggtct tgtcgatcag gatgatctgg acgaagagca tcagggctc     2520 gcgccagccg aactgttcgc caggctcaag gcgagcatgc ccgacggcga ggatctcgtc    2580
gtgacccatg gcgatgcctg cttgccgaat atcatggtgg aaaatggccg cttttctgga    2640
ttcatcgact gtggccggct gggtgtggcg gaccgctatc aggacatagc gttggctacc    2700
cgtgatattg ctgaagagct tggcggcgaa tgggctgacc gcttcctcgt gctttacggt    2760
atcgccgctc ccgattcgca gcgcatcgcc ttctatcgcc ttcttgacga gttcttctga    2820
gcgggactct ggggttcgaa atgaccgacc aagcgacgcc caacctgcca tcacgagatt    2880
tcgattccac cgccgccttc tatgaaaggt tgggcttcgg aatcgttttc cgggacgccg    2940
gctggatgat cctccagcgc ggggatctca tgctggagtt cttcgcccac cctaggggga    3000
ggctaactga aacacggaag gagacaatac cggaaggaac ccgcgctatg acggcaataa    3060
aaagacagaa taaaacgcac ggtgttgggt cgtttgttca taaacgcggg gttcggtccc    3120
agggctggca ctctgtcgat accccaccga gaccccattg gggccaatac gcccgcgttt    3180
cttccttttc cccaccccac cccccaagtt cgggtgaagg cccagggctc gcagccaacg    3240
tcggggcggc aggccctgcc atagcctcag gatgctacgt tctagacgtc aggttactca    3300
tatatacttt agattgattt aaaacttcat ttttaattta aaaggatcta ggtgaagatc    3360 cttttttgata atctcatgac caaaatccct taacgtgagt tttcgttcca ctgagcgtca    3420
gaccccgtag aaaagatcaa aggatcttct tgagatcctt ttttctgcg  cgtaatctgc    3480 tgcttgcaaa caaaaaaacc accgctacca gcggtggttt gtttgccgga tcaagagcta    3540
ccaactcttt ttccgaaggt aactggcttc agcagagcgc agataccaaa tactgtcctt    3600
ctagtgtagc cgtagttagg ccaccacttc aagaactctg tagcaccgcc tacataccct    3660
gctctgctaa tcctgttacc agtggctgct gccagtggcg ataagtcgtg tcttaccggg    3720
ttggactcaa gacgatagtt accggataag gcgcagcggt cgggctgaac ggggggttcg    3780
tgcacacagc ccagcttgga gcgaacgacc tacaccgaac tgagatacct acagcgtgag    3840
```

```
ctatgagaaa gcgccacgct tcccgaaggg agaaaggcgg acaggtatcc ggtaagcggc    3900
agggtcggaa caggagagcg cacgaggagc ttccagggg gaaacgcctg gtatctttat    3960
agtcctgtcg ggtttcgcca cctctgactt gagcgtcgat ttttgtgatg ctcgtcaggg    4020
gggcggagcc tatggaaaaa cgccagcaac gcggccttt tacggttcct ggccttttgc    4080
tggccttttg ctcacatgtt ctttcctgcg ttatcccctg attctgtgga taaccgtatt    4140
accgccatgc at                                                        4152

<210> SEQ ID NO 4
<211> LENGTH: 6
<212> TYPE: DNA
<213> ORGANISM: Artificial sequence
<220> FEATURE:
<223> OTHER INFORMATION: SP1 site

<400> SEQUENCE: 4 gggcgg                                                                  6

<210> SEQ ID NO 5
<211> LENGTH: 7
<212> TYPE: DNA
<213> ORGANISM: Artificial sequence
<220> FEATURE:
<223> OTHER INFORMATION: TRE/AP-1 element

<400> SEQUENCE: 5 tgactca                                                                 7

<210> SEQ ID NO 6
<211> LENGTH: 6
<212> TYPE: DNA
<213> ORGANISM: Artificial sequence
<220> FEATURE:
<223> OTHER INFORMATION: erythroid cell GATA element

<400> SEQUENCE: 6 gataga                                                                  6

<210> SEQ ID NO 7
<211> LENGTH: 11
<212> TYPE: DNA
<213> ORGANISM: Artificial sequence
<220> FEATURE:
<223> OTHER INFORMATION: myeloid tumor element NF-kB binding site

<400> SEQUENCE: 7
gggaattccc c                                                           11

<210> SEQ ID NO 8
<211> LENGTH: 8
<212> TYPE: DNA
<213> ORGANISM: Artificial sequence
<220> FEATURE:
<223> OTHER INFORMATION: a cyclic AMP response element

<400> SEQUENCE: 8 tgacgtca                                                                8

<210> SEQ ID NO 9
<211> LENGTH: 8513
<212> TYPE: DNA
<213> ORGANISM: Artificial sequence
<220> FEATURE:
```

<223> OTHER INFORMATION: vector

<400> SEQUENCE: 9

| | | | | | |
|---|---|---|---|---|---|
| gaattctcat | gtttgacagc | ttatcatcga | ttagtccaat | ttgttaaaga | caggatatca | 60 |
| gtggtccagg | ctcagttttg | actcaacaat | atcaccagct | gaagcctata | gagtacgagc | 120 |
| catagataga | ataaaagatt | ttatttagtc | tccagaaaaa | gggggaatg | aaagacccca | 180 |
| cctgtaggtt | tggcaagcta | gaaatgtagt | cttatgcaat | acacttgtag | tcttgcaaca | 240 |
| tggtaacgat | gagttagcaa | catgccttac | aaggagagaa | aaagcaccgt | gcatgccgat | 300 |
| tggtggaagt | aaggtggtac | gatcgtgcct | tattaggaag | gcaacagaca | ggtctgacat | 360 |
| ggattggacg | aaccactcta | gagaaccatc | agatgtttcc | agggtgcccc | aaggacctga | 420 |
| aaatgaccct | gtgccttatt | tgaactaacc | aatcagttcg | cttctcgctt | ctgttcgcgc | 480 |
| gcttctgctc | cccgagctca | ataaaagagc | ccacaacccc | tcactcggcg | cgccagtcct | 540 |
| ccgattgact | gcgtcgcccg | ggtacccgta | ttcccaataa | agcctcttgc | tgtttgcatc | 600 |
| cgaatcgtgg | actcgctgat | ccttgggagg | gtctcctcag | attgattgac | tgcccacctc | 660 |
| ggggtctttc | atttggaggt | tccaccgaga | tttggagacc | ccagcccagg | gaccaccgac | 720 |
| ccccccgccg | ggaggtaagc | tggccagcgg | tcgtttcgtg | tctgtctctg | tctttgtgcg | 780 |
| tgtttgtgcc | ggcatctaat | gtttgcgcct | gcgtctgtac | tagttagcta | actagctctg | 840 |
| tatctggcgg | acccgtggtg | gaactgacga | gttctgaaca | cccggccgca | accctgggag | 900 |
| acgtcccagg | gactttgggg | gccgttttg | tggcccgacc | tgaggaaggg | agtcgatgtg | 960 |
| gaatccgacc | ccgtcaggat | atgtggttct | ggtaggagac | gagaacctaa | aacagttccc | 1020 |
| gcctccgtct | gaattttgc | tttcggtttg | gaaccgaagc | cgcgcgtctt | gtctgctgca | 1080 |
| gcatcgttct | gtgttgtctc | tgtctgactg | tgtttctgta | tttgtctgaa | aattagggcc | 1140 |
| agactgttac | cactcccta | agtttgacct | taggtcactg | gaaagatgtc | gagcggatcg | 1200 |
| ctcacaacca | gtcggtagat | gtcaagaaga | gacgttgggt | taccttctgc | tctgcagaat | 1260 |
| ggccaacctt | taacgtcgga | tggccgcgag | acggcaccttt | taaccgagac | ctcatcaccc | 1320 |
| aggttaagat | caaggtctttt | cacctggccc | gcatggacac | ccagaccagg | tcccctacat | 1380 |
| cgtgacctgg | gaagccttgg | cttttgaccc | ccctccctgg | gtcaagccct | ttgtacaccc | 1440 |
| taagccctccg | cctcctcttc | ctccatccgc | cccgtctctc | cccttgaac | ctcctcgttc | 1500 |
| gaccccgcct | cgatcctccc | tttatccagc | cctcactcct | tctctaggcg | ccggaattcg | 1560 |
| ttcatggtga | gcaagggcga | ggagctgttc | accggggtgg | tgcccatcct | ggtcgagctg | 1620 |
| gacggcgacg | taaacggcca | caagttcagc | gtgtccggcg | agggcgaggg | cgatgccacc | 1680 |
| tacggcaagc | tgaccctgaa | gttcatctgc | accaccggca | agctgcccgt | gccctggccc | 1740 |
| accctcgtga | ccaccctgac | ctacggcgtg | cagtgcttca | gccgctaccc | cgaccacatg | 1800 |
| aagcagcacg | acttcttcaa | gtccgccatg | cccgaaggct | acgtccagga | gcgcaccatc | 1860 |
| ttcttcaagg | acgacggcaa | ctacaagacc | cgcgccgagg | tgaagttcga | gggcgacacc | 1920 |
| ctggtgaacc | gcatcgagct | gaagggcatc | gacttcaagg | aggacggcaa | catcctgggg | 1980 |
| cacaagctgg | agtacaacta | caacagccac | aacgtctata | tcatggccga | caagcagaag | 2040 |
| aacggcatca | aggccaactt | caagacccgc | cacaacatcg | aggacggcgg | cgtgcagctc | 2100 |
| gccgaccact | accagcagaa | cacccccatc | ggcgacggcc | ccgtgctgct | gcccgacaac | 2160 |
| cactacctga | gcacccagtc | cgccctgagc | aaagacccca | acgagaagcg | cgatcacatg | 2220 |
| gtcctgctgg | agttcgtgac | cgccgccggg | atcactctcg | gcatggacga | gctgtacaag | 2280 |

```
taaagcggcc gcgactctag agtcgaggat cctctagagg aattcccgcc cctctccctc    2340
ccccccccct aacgttactg gccgaagccg cttggaataa ggccggtgtg cgtttgtcta    2400
tatgttattt tccaccatat tgccgtcttt tggcaatgtg agggcccgga aacctggccc    2460
tgtcttcttg acgagcattc ctaggggtct ttcccctctc gccaaaggaa tgcaaggtct    2520
gttgaatgtc gtgaaggaag cagttcctct ggaagcttct tgaagacaaa caacgtctgt    2580
agcgaccctt tgcaggcagc ggaacccccc acctggcgac aggtgcctct gcggccaaaa    2640
gccacgtgta taagatacac ctgcaaaggc ggcacaaccc cagtgccacg ttgtgagttg    2700
gatagttgtg gaaagagtca atggctctc ctcaagcgta ttcaacaagg gggctgaagg     2760
atgcccagaa ggtaccccat tgtatggat ctgatctggg gcctcggtgc acatgcttta     2820
catgtgttta gtcgaggtta aaaaaacgtc taggcccccc gaaccacggg gacgtggttt    2880
tcctttgaaa aacacgatga taagcttgcc acaaccatgt tgcaaactaa ggatctcatc    2940
tggactttgt ttttcctggg aactgcagtt tctctgcagg tggatattgt tcccagccag    3000
ggggagatca gcgttggaga gtccaaattc ttcttatgcc aagtggcagg agatgccaaa    3060
gataaagaca tctcctggtt ctcccccaat ggagaaaagc tcaccccaaa ccagcagcgg    3120
atctcagtgg tgtggaatga tgattcctcc tccaccctca ccatctataa cgccaacatc    3180
gacgacgccg gcatttacaa gtgtgtggtt acaggcgagt atggcagtga gtcagaggcc    3240
accgtcaacg tgaagatctt tcagaagctc atgttcaaga atgcgccaac cccacaggag    3300
ttccgggagg gggaagatgc cgtgattgtg tgtgatgtgg tcagctccct cccaccaacc    3360
atcatctgga acacaaagg ccgagatgtc atcctgaaaa agatgtccg attcatagtc      3420
ctgtccaaca actacctgca gatccggggc atcaagaaaa cagatgaggg cacttatcgc    3480
tgtgagggca gaatcctggc acggggggag atcaacttca aggacattca ggtcattgtg    3540
aatgtgccac ctaccatcca ggccaggcag aatattgtga atgccaccgc caacctcggc    3600
cagtccgtca ccctggtgtg cgatgccgaa ggcttcccag agcccaccat gagctggaca    3660
aaggatgggg aacagataga gcaagaggaa gacgatgaga agtacatctt cagcgacgat    3720
agttcccagc tgaccatcaa aaaggtggat aagaacgacg aggctgagta catctgcatt    3780
gctgagaaca aggctggcga gcaggatgcg accatccacc tcaaagtctt tgcaaaaccc    3840
aaaatcacat atgtagagaa ccagactgcc atggaattag aggagcaggt cactcttacc    3900
tgtgaagcct ccgagacccc cattccctcc atcacctgga ggacttctac ccggaacatc    3960
agcagcgaag aaaagactct ggatgggcac atggtggtgc gtagccatgc ccgtgtgtcg    4020
tcgctgacc tgaagagcat ccagtacact gatgccggag agtacatctg caccgccagc    4080
aacaccatcg gccaggactc ccagtccatg taccttgaag tgcaatatgc cccaaagcta    4140
cagggccctg tggctgtgta cacttgggag gggaaccagg tgaacatcac ctgcgaggta    4200
tttgcctatc ccagtgccac gatctcatgg tttcgggatg ccagctgct gccaagctcc    4260
aattacagca atatcaagat ctacaacacc ccctctgcca gctatctgga ggtgaccccca    4320
gactctgaga atgattttgg gaactacaac tgtactgcag tgaaccgcat tgggcaggag    4380
tccttggaat tcatccttgt tcaagcagac accccctctt caccatccat cgaccaggtg    4440
gagccatact ccagcacagc ccaggtgcag tttgatgaac cagaggccac aggtgggtgt    4500
cccatcctca aatacaaagc tgagtggaga gcagttggtg aagaagtatg gcattccaag    4560
tggtatgatg ccaaggaagc cagcatggag ggcatcgtca ccatcgtggg cctgaagccc    4620
```

```
gaaacaacgt acgccgtaag gctggcggcg ctcaatggca aagggctggg tgagatcagc    4680
gcggcctccg agttcaagac gcagccagtc cgggaaccca gtgcacctaa gctcgaaggg    4740
cagatgggag aggatggaaa ctctattaaa gtgaacctga tcaagcagga tgacggcggc    4800
tcccccatca gacactatct ggtcaggtac cgagcgctct cctccgagtg gaaaccagag    4860
atcaggctcc cgtctggcag tgaccacgtc atgctgaagt ccctggactg gaatgctgag    4920
tatgaggtct acgtggtggc tgagaaccag caaggaaaat ccaaggcggc tcattttgtg    4980
ttcaggacct cggcccagcc cacagccatc ccagccaacg gcagcccac ctcaggcctg     5040 agcaccgggg ccatcgtggg catcctcatc gtcatcttcg tcctgctcct ggtggttgtg    5100
gacatcacct gctacttcct gaacaagtgt ggcctgttca tgtgcattgc ggtcaacctg    5160
tgtggaaaag ccgggcccgg ggccaagggc aaggacatgg aggagggcaa ggccgccttc    5220
tcgaaagatg agtccaagga gcccatcgtg gaggttcgaa cggaggagga gaggaccccca   5280 aaccatgatg gagggaaaca cacagagccc aacgagacca cgccactgac ggagcccgag    5340 aagggcccg tagaagcaaa gccagagtgc caggagacag aaacgaagcc agcgccagcc     5400
gaagtcaaga cggtccccaa tgacgccaca cagacaaagg agaacgagag caaagcatga    5460
tgggatcgtc gacggtatcg ataaaataaa agattttatt tagtctccag aaaaagggggg   5520 gaatgaaaga cccccacctgt aggtttggca agctagacat gcatcgggat atcctagcta   5580
gcccgctcga gcgaacgcgt gaagatctga aggggggcta taaaagcgat ggatccgagc    5640
tcggccctca ttctggagac tctagaggcc ttgaattcgc ggccgcgcca gtcctccgat    5700
tgactgcgtc gcccgggtac cgtgtatcca ataaaccctc ttgcagttgc atccgacttg    5760
tggtctcgct gttccttggg agggtctcct ctgagtgatt gactacccgt cagcgggggt    5820 cttttcatttg ggggctcgtc cgggatcggg agaccctgc ccaggaccca ccgacccacc    5880
accgggaggt aagctggctg cctcgcgcgt ttcggtgatg acggtgaaaa cctctgacac    5940
atgcagctcc cggagacggt cacagcttgt ctgtaagcgg atgccgggag cagacaagcc    6000
cgtcagggcg cgtcagcggg tgttggcggg tgtcggggcg cagccatgac ccagtcacgt    6060
agcgatagcg gagtgtatac tggcttaact atgcggcatc agagcagatt gtactgagag    6120
tgcaccatat gtccgcccat cccgccccta actccgccca gttccgccca ttctccgccc    6180
catggctgac taatttttttt tatttatgca gaggccgagg ccgcctcggc ctctgagcta   6240
ttccagaagt agtgaggagg ctttttttgga ggcctaggct tttgcaacat atgtccgccc    6300
atcccgcccc taactccgcc cagttccgcc cattctccgc cccatggctg actaatttttt   6360 tttatttatg cagaggccga ggccgcctcg gcctctgagc tattccagaa gtagtgagga    6420
ggcttttttg gaggcctagg cttttgcaac atatgcggtg tgaaataccg cacagatgcg    6480
taaggagaaa ataccgcatc aggcgctctt ccgcttcctc gctcactgac tcgctgcgct    6540
cggtcgttcg gctgcggcga gcggtatcag ctcactcaaa ggcggtaata cggttatcca    6600
cagaatcagg ggataacgca ggaaagaaca tgtgagcaaa aggccagcaa aaggccagga    6660
accgtaaaaa ggccgcgttg ctggcgtttt tccataggct ccgccccccct gacgagcatc    6720 acaaaaatcg acgctcaagt cagaggtggc gaaacccgac aggactataa agataccagg    6780
cgtttccccc tggaagctcc ctcgtgcgct ctcctgttcc gaccctgccg cttaccggat    6840
acctgtccgc cttctcccct tcgggaagcg tggcgctttc tcatagctca cgctgtaggt    6900
atctcagttc ggtgtaggtc gttcgctcca agctgggctg tgtgcacgaa ccccccgttc    6960
agcccgaccg ctgcgcctta tccggtaact atcgtcttga gtccaacccg gtaagacacg    7020
```

```
acttatcgcc actggcagca gccactggta acaggattag cagagcgagg tatgtaggcg    7080
gtgctacaga gttcttgaag tggtggccta actacggcta cactagaagg acagtatttg    7140
gtatctgcgc tctgctgaag ccagttacct tcggaaaaag agttggtagc tcttgatccg    7200
gcaaacaaac caccgctggt agcggtggtt tttttgtttg caagcagcag attacgcgca    7260
gaaaaaaagg atctcaagaa gatcctttga tcttttctac ggggtctgac gctcagtgga    7320
acgaaaactc acgttaaggg attttggtca tgagattatc aaaaaggatc ttcacctaga    7380
tccttttaaa ttaaaaatga agttttaaat caatctaaag tatatatgag taaacttggt    7440
ctgacagtta ccaatgctta atcagtgagg cacctatctc agcgatctgt ctatttcgtt    7500
catccatagt tgcctgactc cccgtcgtgt agataactac gatacgggag ggcttaccat    7560
ctggccccag tgctgcaatg ataccgcgag acccacgctc accggctcca gatttatcag    7620
caataaacca gccagccgga agggccgagc gcagaagtgg tcctgcaact ttatccgcct    7680
ccatccagtc tattaattgt tgccgggaag ctagagtaag tagttcgcca gttaatagtt    7740
tgcgcaacgt tgttgccatt gctgcaggca tcgtggtgtc acgctcgtcg tttggtatgg    7800
cttcattcag ctccggttcc caacgatcaa ggcgagttac atgatccccc atgttgtgca    7860
aaaaagcggt tagctccttc ggtcctccga tcgttgtcag aagtaagttg gccgcagtgt    7920
tatcactcat ggttatggca gcactgcata attctcttac tgtcatgcca tccgtaagat    7980
gcttttctgt gactggtgag tactcaacca agtcattctg agaatagtgt atgcggcgac    8040
cgagttgctc ttgcccggcg tcaacacggg ataataccgc gccacatagc agaactttaa    8100
aagtgctcat cattggaaaa cgttcttcgg ggcgaaaact ctcaaggatc ttaccgctgt    8160
tgagatccag ttcgatgtaa cccactcgtg cacccaacta tcttcagca tcttttactt    8220 tcaccagcgt ttctgggtga gcaaaaacag gaaggcaaaa tgccgcaaaa aagggaataa    8280
gggcgacacg gaaatgttga atactcatac tcttcctttt tcaatattat tgaagcattt    8340
atcagggtta ttgtctcatg agcggataca tatttgaatg tatttagaaa aataaacaaa    8400 tagggggttcc gcgcacattt ccccgaaaag tgccacctga cgtctaagaa accattatta    8460
tcatgacatt aacctataaa aataggcgta tcacgaggcc ctttcgtctt caa           8513

<210> SEQ ID NO 10
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 10
cgctcgcccc ctcccgatcg cctttggatc acgcgtgatc caggggggaac gaatcaaagc    60 cgagcg                                                                66

<210> SEQ ID NO 11
<211> LENGTH: 30
<212> TYPE: DNA
<213> ORGANISM: Artificial sequence
<220> FEATURE:
<223> OTHER INFORMATION: transcriptional regulatory element

<400> SEQUENCE: 11
gatccagggc aagaaaagca ccagcgagcg                                      30

<210> SEQ ID NO 12
```

```
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 12
gatccaggag ggcaagggga ggggcgagcg acgcgtgatc cacgagcagc tggtgatgga      60
cgagcg                                                                 66

<210> SEQ ID NO 13
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 13
cgctcgccct atgtgcgctc aacctggatc acgcgtcgct cgccacccac tttttgccct      60
tggatc                                                                 66

<210> SEQ ID NO 14
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 14
cgctcgtcct gccgtcgacc tccctggatc acgcgtgatc cacacaggag tagaaaacat      60
cgagcg                                                                 66

<210> SEQ ID NO 15
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 15
cgctcggcac gcattagccc ctggtggatc acgcgtgatc cagggcagac gggagagaga      60
cgagcg                                                                 66

<210> SEQ ID NO 16
<211> LENGTH: 65
<212> TYPE: DNA
<213> ORGANISM: Artificial sequence
<220> FEATURE:
<223> OTHER INFORMATION: transcriptional regulatory element

<400> SEQUENCE: 16
cgctcgcttc ccgcccccccc ctatggatca cgcgtcgctc gtccttctgc gtaaccttt      60 ggatc                                                                  65

<210> SEQ ID NO 17
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 17
cgctcgaacc ctccctgttc tttttggatc acgcgtcgct cgccccctcc tccctctcgc      60
```

-continued

```
tggatc                                                                66

<210> SEQ ID NO 18
<211> LENGTH: 18
<212> TYPE: DNA
<213> ORGANISM: Artificial sequence
<220> FEATURE:
<223> OTHER INFORMATION: flanking sequence

<400> SEQUENCE: 18
ctactcacgc gtgatcca                                                   18

<210> SEQ ID NO 19
<211> LENGTH: 18
<212> TYPE: DNA
<213> ORGANISM: Artificial sequence
<220> FEATURE:
<223> OTHER INFORMATION: flanking sequence

<400> SEQUENCE: 19
cggcgaacgc gtgcaatg                                                   18

<210> SEQ ID NO 20
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 20
cgctcgcctg tccgccgcac ttgttggatc acgcgtgatc caccaggaag tgacgtatca     60
cgagcg                                                                66

<210> SEQ ID NO 21
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 21
cgctcgcaac tctttccccc ccctggacc acgcgtgatc caccaggaag tgacgtatca      60
cgagcg                                                                66

<210> SEQ ID NO 22
<211> LENGTH: 138
<212> TYPE: DNA
<213> ORGANISM: Artificial sequence
<220> FEATURE:
<223> OTHER INFORMATION: transcriptional regulatory element

<400> SEQUENCE: 22
gatccaggga ggggtagggt ctatcgagcg acgcgtcgct cgtctcctct acacccgctg     60
tggatcacgc gtcgctcgtt gccctcccct tcctcatgga tcacgcgtcg ctcgctgtcc   120
ccgccccact cctggatc                                                  138

<210> SEQ ID NO 23
<211> LENGTH: 105
<212> TYPE: DNA
<213> ORGANISM: Artificial sequence
<220> FEATURE:
<223> OTHER INFORMATION: transcriptional regulatory element
```

```
<400> SEQUENCE: 23
gatccaagag cgggcaggga ttggcgagcg acgcgtcgtc gctcgtcccg cccctctat      60 gcttggatca cgcgtcgctc gtcctcttct ttccttccct ggatc                    105

<210> SEQ ID NO 24
<211> LENGTH: 30
<212> TYPE: DNA
<213> ORGANISM: Artificial sequence
<220> FEATURE:
<223> OTHER INFORMATION: transcriptional regulatory element

<400> SEQUENCE: 24
cgctcggccc cgccctcttc cccctggatc                                      30

<210> SEQ ID NO 25
<211> LENGTH: 65
<212> TYPE: DNA
<213> ORGANISM: Artificial sequence
<220> FEATURE:
<223> OTHER INFORMATION: transcriptional regulatory element

<400> SEQUENCE: 25
cgctcgctct tgtgtacctc tccttggatc acgcgtcgct cgccatcttc tgtcgctgct     60
ggatc                                                                 65

<210> SEQ ID NO 26
<211> LENGTH: 30
<212> TYPE: DNA
<213> ORGANISM: Artificial sequence
<220> FEATURE:
<223> OTHER INFORMATION: transcriptional regulatory element

<400> SEQUENCE: 26
cgctcgtctc ttctcgcccc cccctggatc                                      30

<210> SEQ ID NO 27
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 27
cgctcgcccc tcccctaagc gcgttggatc acgcgtgatc caacgggcaa tgaaacgaat     60
cgagcg                                                                66

<210> SEQ ID NO 28
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 28
cgctcgctgg ccccgccctt agtttggatc acgcgtcgct cgaccccgcc tttcgtatct     60
tggatc                                                                66

<210> SEQ ID NO 29
<211> LENGTH: 66
<212> TYPE: DNA
<213> ORGANISM: Artificial sequence
<220> FEATURE:
<223> OTHER INFORMATION: transcriptional regulatory element
```

<400> SEQUENCE: 29
cgctcgtcgc ctgggttctg ctactggatc acgcgtgatc cagaagagcg gaaggaggga    60
cgagcg                                                              66

<210> SEQ ID NO 30
<211> LENGTH: 30
<212> TYPE: DNA
<213> ORGANISM: Artificial sequence
<220> FEATURE:
<223> OTHER INFORMATION: transcriptional regulatory element

<400> SEQUENCE: 30
cgctcgcctt cccttacttc acgctggatc                                    30

<210> SEQ ID NO 31
<211> LENGTH: 65
<212> TYPE: DNA
<213> ORGANISM: Artificial sequence
<220> FEATURE:
<223> OTHER INFORMATION: transcriptional regulatory element

<400> SEQUENCE: 31
cgctcgcctc acgcgaattc ccctggatc acgcgtgatc cagagaaggg aggggggac    60 gagcg                                                               65

<210> SEQ ID NO 32
<211> LENGTH: 30
<212> TYPE: DNA
<213> ORGANISM: Artificial sequence
<220> FEATURE:
<223> OTHER INFORMATION: transcriptional regulatory element

<400> SEQUENCE: 32
gatccagggg caaaaaggga ggggcgagcg                                    30

<210> SEQ ID NO 33
<211> LENGTH: 30
<212> TYPE: DNA
<213> ORGANISM: Artificial sequence
<220> FEATURE:
<223> OTHER INFORMATION: transcriptional regulatory element

<400> SEQUENCE: 33
gatccaggtg gggctagtga cgtgcgagcg                                    30

<210> SEQ ID NO 34
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 34
gatccagata gacgggagtg aaaacgagcg acgcgtgatc caagcggagg agggatgtga    60
cgagcg                                                              66

<210> SEQ ID NO 35
<211> LENGTH: 66
<212> TYPE: DNA
<213> ORGANISM: Artificial sequence
<220> FEATURE:
<223> OTHER INFORMATION: transcriptional regulatory element

```
<400> SEQUENCE: 35
gatccaatca aggaggaggg atagcgagcg acgcgtcgct cgtttccggt cttatgtttg    60
tggatc                                                               66

<210> SEQ ID NO 36
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 36
cgctcgcccc ccgccctctt tgcctggatc acgcgtgatc caggtggggc tagtgacgtg    60
cgacgc                                                               66

<210> SEQ ID NO 37
<211> LENGTH: 30
<212> TYPE: DNA
<213> ORGANISM: Artificial sequence
<220> FEATURE:
<223> OTHER INFORMATION: transcriptional regulatory element

<400> SEQUENCE: 37
gatccagaaa agtgagggga ggggcgagcg                                     30

<210> SEQ ID NO 38
<211> LENGTH: 66
<212> TYPE: DNA
<213> ORGANISM: Artificial sequence
<220> FEATURE:
<223> OTHER INFORMATION: transcriptional regulatory element

<400> SEQUENCE: 38
gatccaggga cagtgagggg gggacgagcg acgcgttgct cgtccatttc acgccccgc    60 tggatc                                                               66

<210> SEQ ID NO 39
<211> LENGTH: 30
<212> TYPE: DNA
<213> ORGANISM: Artificial sequence
<220> FEATURE:
<223> OTHER INFORMATION: transcriptional regulatory element

<400> SEQUENCE: 39
gatccaactg gagagtaacg ccctcgagcg                                     30

<210> SEQ ID NO 40
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 40
ggcattcatc gt                                                        12

<210> SEQ ID NO 41
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 41
```

```
gcattagtat ct                                                          12

<210> SEQ ID NO 42
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 42
tcggttattg tt                                                          12

<210> SEQ ID NO 43
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 43
tccaattggg aa                                                          12

<210> SEQ ID NO 44
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 44
atctattggc ca                                                          12

<210> SEQ ID NO 45
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 45
ttactgggtg tt                                                          12

<210> SEQ ID NO 46
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 46
agggtgaagg tc                                                          12

<210> SEQ ID NO 47
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 47
ggtgggtgtg tc                                                          12

<210> SEQ ID NO 48
<211> LENGTH: 12
<212> TYPE: DNA
```

```
<213> ORGANISM: Artificial sequence
<220> FEATURE:
<223> OTHER INFORMATION: transcriptional regulatory element

<400> SEQUENCE: 48
cgcttcaatg ct                                                          12

<210> SEQ ID NO 49
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 49
tgcttcaatg cc                                                          12

<210> SEQ ID NO 50
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 50
tgtgtctttg ca                                                          12

<210> SEQ ID NO 51
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 51
cacggggaca gc                                                          12

<210> SEQ ID NO 52
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 52
aagctgtaca tg                                                          12

<210> SEQ ID NO 53
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 53
gatgggggca ca                                                          12

<210> SEQ ID NO 54
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 54
atatgtgccc tt                                                          12
```

<210> SEQ ID NO 55
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 55
tccttctggg tc					12

<210> SEQ ID NO 56
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 56
ggtgggtgtg tc					12

<210> SEQ ID NO 57
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 57
gaatggatgg gg					12

<210> SEQ ID NO 58
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 58
catgtgatat tc					12

<210> SEQ ID NO 59
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 59
aggagggttt gt					12

<210> SEQ ID NO 60
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 60
tgggcgagtg gg					12

<210> SEQ ID NO 61
<211> LENGTH: 12
<212> TYPE: DNA
<213> ORGANISM: Artificial sequence
<220> FEATURE:

<223> OTHER INFORMATION: transcriptional regulatory element

<400> SEQUENCE: 61
cggctcacca gt                                                           12

<210> SEQ ID NO 62
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 62
ggtttctata ac                                                           12

<210> SEQ ID NO 63
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 63
ggtgggtgtg tc                                                           12

<210> SEQ ID NO 64
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 64
ttactgggtg tt                                                           12

<210> SEQ ID NO 65
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 65
aagtctttgg gt                                                           12

<210> SEQ ID NO 66
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 66
ggttgggtcc cc                                                           12

<210> SEQ ID NO 67
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 67
ttgggtcatt gt                                                           12

```
<210> SEQ ID NO 68
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 68
ttgggtcgtt gt                                                              12

<210> SEQ ID NO 69
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 69
tctgggtcgc gc                                                              12

<210> SEQ ID NO 70
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 70
tccttctggg tc                                                              12

<210> SEQ ID NO 71
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 71
cctttgtggg tc                                                              12

<210> SEQ ID NO 72
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 72
tcacttctgg gc                                                              12

<210> SEQ ID NO 73
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 73
ctagtgggag ct                                                              12

<210> SEQ ID NO 74
<211> LENGTH: 12
<212> TYPE: DNA
<213> ORGANISM: Artificial sequence
<220> FEATURE:
<223> OTHER INFORMATION: transcriptional regulatory element
```

<400> SEQUENCE: 74
tgggcgagtg gg                                                              12

<210> SEQ ID NO 75
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 75
tgcttcaatg cc                                                              12

<210> SEQ ID NO 76
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 76
cgcctcgatg cc                                                              12

<210> SEQ ID NO 77
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 77
agggtgaagg tc                                                              12

<210> SEQ ID NO 78
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 78
acccggggaa gg                                                              12

<210> SEQ ID NO 79
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 79
tgtgtctttg ca                                                              12

<210> SEQ ID NO 80
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 80
cgaactttgc aa                                                              12

<210> SEQ ID NO 81
<211> LENGTH: 12

```
<212> TYPE: DNA
<213> ORGANISM: Artificial sequence
<220> FEATURE:
<223> OTHER INFORMATION: transcriptional regulatory element

<400> SEQUENCE: 81
tgagtaagct at                                                      12

<210> SEQ ID NO 82
<211> LENGTH: 12
<212> TYPE: DNA
<213> ORGANISM: Artificial sequence
<220> FEATURE:
<223> OTHER INFORMATION: transcriptional regulatory element

<400> SEQUENCE: 82
tatgtaagaa cg                                                      12

<210> SEQ ID NO 83
<211> LENGTH: 6
<212> TYPE: DNA
<213> ORGANISM: Artificial sequence
<220> FEATURE:
<223> OTHER INFORMATION: core motif

<400> SEQUENCE: 83 ttgggt                                                              6

<210> SEQ ID NO 84
<211> LENGTH: 8
<212> TYPE: DNA
<213> ORGANISM: Artificial sequence
<220> FEATURE:
<223> OTHER INFORMATION: core motif

<400> SEQUENCE: 84 ctagtggg                                                            8

<210> SEQ ID NO 85
<211> LENGTH: 5
<212> TYPE: DNA
<213> ORGANISM: Artificial sequence
<220> FEATURE:
<223> OTHER INFORMATION: core motif

<400> SEQUENCE: 85 atgcc                                                               5

<210> SEQ ID NO 86
<211> LENGTH: 5
<212> TYPE: DNA
<213> ORGANISM: Artificial sequence
<220> FEATURE:
<223> OTHER INFORMATION: core motif

<400> SEQUENCE: 86 gaagg                                                               5

<210> SEQ ID NO 87
<211> LENGTH: 8
<212> TYPE: DNA
<213> ORGANISM: Artificial sequence
<220> FEATURE:
<223> OTHER INFORMATION: core motif

<400> SEQUENCE: 87
```

-continued

```
cttttgca                                                         8

<210> SEQ ID NO 88
<211> LENGTH: 163
<212> TYPE: DNA
<213> ORGANISM: Saccharomyces cerevisiae

<400> SEQUENCE: 88
accgattaag cacagtacct ttacgttata tataggattg gtgtttagct ttttttcctg    60
agcccctggt tgacttgtgc atgaacacga gccatttta gtttgtttaa gggaagtttt    120
ttgccaccca aaacgtttaa agaaggaaaa gttgtttctt aaa                     163

<210> SEQ ID NO 89
<211> LENGTH: 511
<212> TYPE: DNA
<213> ORGANISM: Saccharomyces cerevisiae

<400> SEQUENCE: 89
aatcattttt ttgaaaatta cattaataag gcttttttca atatctctgg aacaacagtt    60
tgtttctact tactaatagc tttaaggacc ctcttggaca tcatgatggc agacttccat    120
cgtagtggga tgatcatatg atgggcgcta tcctcatcgc gactcgataa cgacgtgaga    180
aacgattttt ttttttcttt ttcaccgtat ttttgtgcgt cctttttcaa ttatagcttt    240
tttttatttt tttttttttct cgtactgttt cactgacaaa agttttttt caagaaaaat    300 tttcgatgcc gcgttctctg tgtgcaacgg atggatggta gatggaattt caatatgttg    360
cttgaaattt taccaatctt gatattgtga taatttactt aattatgatt cttcctcttc    420
ccttcaattt cttaaagctt cttactttac tccttcttgc tcataaataa gcaaggtaag    480
aggacaactg taattaccta ttacaataat g                                  511

<210> SEQ ID NO 90
<211> LENGTH: 10
<212> TYPE: RNA
<213> ORGANISM: Saccharomyces cerevisiae

<400> SEQUENCE: 90
acgagccauu                                                        10

<210> SEQ ID NO 91
<211> LENGTH: 10
<212> TYPE: RNA
<213> ORGANISM: Saccharomyces cerevisiae

<400> SEQUENCE: 91
aauggcucau                                                        10

<210> SEQ ID NO 92
<211> LENGTH: 16
<212> TYPE: RNA
<213> ORGANISM: Saccharomyces cerevisiae

<400> SEQUENCE: 92
gaaauuugca aaaccc                                                 16

<210> SEQ ID NO 93
<211> LENGTH: 16
<212> TYPE: RNA
<213> ORGANISM: Saccharomyces cerevisiae

<400> SEQUENCE: 93
```

-continued cuuagaacgu ucuggg         16

<210> SEQ ID NO 94
<211> LENGTH: 13
<212> TYPE: RNA
<213> ORGANISM: Saccharomyces cerevisiae

<400> SEQUENCE: 94
cagacuucca ucg            13

<210> SEQ ID NO 95
<211> LENGTH: 13
<212> TYPE: RNA
<213> ORGANISM: Saccharomyces cerevisiae

<400> SEQUENCE: 95
cgauggaagu uug            13

<210> SEQ ID NO 96
<211> LENGTH: 19
<212> TYPE: RNA
<213> ORGANISM: Saccharomyces cerevisiae

<400> SEQUENCE: 96
gcgcuauccu caucgcgac      19

<210> SEQ ID NO 97
<211> LENGTH: 19
<212> TYPE: RNA
<213> ORGANISM: Saccharomyces cerevisiae

<400> SEQUENCE: 97
gucgugcugg ggauagagc      19

<210> SEQ ID NO 98
<211> LENGTH: 15
<212> TYPE: RNA
<213> ORGANISM: Saccharomyces cerevisiae

<400> SEQUENCE: 98
uuaugauucu uccuc          15

<210> SEQ ID NO 99
<211> LENGTH: 15
<212> TYPE: RNA
<213> ORGANISM: Saccharomyces cerevisiae

<400> SEQUENCE: 99
gcggaaggau cauua          15

<210> SEQ ID NO 100
<211> LENGTH: 25
<212> TYPE: RNA
<213> ORGANISM: Saccharomyces cerevisiae

<400> SEQUENCE: 100
cuucccuuca auucuuaaa gcuuc    25

<210> SEQ ID NO 101
<211> LENGTH: 25
<212> TYPE: RNA
<213> ORGANISM: Saccharomyces cerevisiae

```
<400> SEQUENCE: 101
gaaacuuaaa ggaauugacg gaagg                                          25

<210> SEQ ID NO 102
<211> LENGTH: 9
<212> TYPE: DNA
<213> ORGANISM: Mus musculus

<400> SEQUENCE: 102 ccggcgggt                                                             9

<210> SEQ ID NO 103
<211> LENGTH: 42
<212> TYPE: DNA
<213> ORGANISM: Artificial sequence
<220> FEATURE:
<223> OTHER INFORMATION: oligonucleotide containing 18 random
      nucleotide
<220> FEATURE:
<221> NAME/KEY: misc_feature
<222> LOCATION: (1)..(42)
<223> OTHER INFORMATION: n is either a, c, g, or t

<400> SEQUENCE: 103
acgcgtgatc cannnnnnnn nnnnnnnnnn cgagcgacgc gt                        42

<210> SEQ ID NO 104
<211> LENGTH: 135
<212> TYPE: DNA
<213> ORGANISM: Artificial sequence
<220> FEATURE:
<223> OTHER INFORMATION: oligonucleotide containing two segments of 9
      random nucleotides
<220> FEATURE:
<221> NAME/KEY: misc_feature
<222> LOCATION: (69)..(77)
<223> OTHER INFORMATION: n is either a, c, g, or t
<220> FEATURE:
<221> NAME/KEY: misc_feature
<222> LOCATION: (87)..(95)
<223> OTHER INFORMATION: n is either a, c, g, or t

<400> SEQUENCE: 104
ttaattaaga attcttctga cataaaaaaa aattctgaca taaaaaaaaa ttctgacata     60
aaaaaaaann nnnnnnnaaa aaaaaannnn nnnnaaaaa aaaagactca caaccccaga    120
aacagacata cgcgt                                                    135

<210> SEQ ID NO 105
<211> LENGTH: 30
<212> TYPE: RNA
<213> ORGANISM: Artificial sequence
<220> FEATURE:
<223> OTHER INFORMATION: ICS 1-23 a-b

<400> SEQUENCE: 105
gauccagagc aggaacagcg gaaacgagcg                                     30

<210> SEQ ID NO 106
<211> LENGTH: 15
<212> TYPE: RNA
<213> ORGANISM: Artificial sequence
<220> FEATURE:
<223> OTHER INFORMATION: ICS 1-23 b

<400> SEQUENCE: 106
cagcggaaac gagcg                                                     15
```

<210> SEQ ID NO 107
<211> LENGTH: 14
<212> TYPE: RNA
<213> ORGANISM: Saccharomyces cerevisiae

<400> SEQUENCE: 107
uucucgauuc cgug                                                            14

<210> SEQ ID NO 108
<211> LENGTH: 9
<212> TYPE: DNA
<213> ORGANISM: Artificial sequence
<220> FEATURE:
<223> OTHER INFORMATION: 9 nt segment designated as ICS2-17.2

<400> SEQUENCE: 108 tccggtcgt                                                                   9

<210> SEQ ID NO 109
<211> LENGTH: 6250
<212> TYPE: DNA
<213> ORGANISM: Artificial sequence
<220> FEATURE:
<223> OTHER INFORMATION: vector

<400> SEQUENCE: 109
gaattctcat gtttgacagc ttatcatcga ttagtccaat ttgttaaaga caggatatca     60
gtggtccagg ctcagttttg actcaacaat atcaccagct gaagcctata gagtacgagc    120
catagataga ataaaagatt ttatttagtc tccagaaaaa ggggggaatg aaagacccca    180
cctgtaggtt tggcaagcta aaatgtagt cttatgcaat acacttgtag tcttgcaaca    240
tggtaacgat gagttagcaa catgccttac aaggagagaa aaagcaccgt gcatgccgat    300
tggtggaagt aaggtggtac gatcgtgcct tattaggaag caacagaca ggtctgacat    360
ggattggacg aaccactcta gagaaccatc agatgtttcc agggtgcccc aaggacctga    420
aaatgaccct gtgccttatt tgaactaacc aatcagttcg cttctcgctt ctgttcgcgc    480
gcttctgctc cccgagctca ataaaagagc ccacaacccc tcactcggcg cgccagtcct    540
ccgattgact gcgtcgcccg gtacccgta ttcccaataa agcctcttgc tgtttgcatc    600
cgaatcgtgg actcgctgat ccttgggagg gtctcctcag attgattgac tgcccacctc    660
ggggtctttc atttggaggt tccaccgaga tttggagacc ccagcccagg gaccaccgac    720
cccccgccg ggaggtaagc tggccagcgg tcgtttcgtg tctgtctctg tctttgtgcg    780
tgtttgtgcc ggcatctaat gtttgcgcct gcgtctgtac tagttagcta actagctctg    840
tatctggcgg acccgtggtg gaactgacga gttctgaaca cccggccgca accctgggag    900
acgtcccagg gactttgggg gccgtttttg tggcccgacc tgaggaaggg agtcgatgtg    960
gaatccgacc ccgtcaggat atgtggttct ggtaggagac gagaacctaa aacagttccc   1020
gcctccgtct gaattttgc tttcggtttg gaaccgaagc cgcgcgtctt gtctgctgca   1080
gcatcgttct gtgttgtctc tgtctgactg tgtttctgta tttgtctgaa aattagggcc   1140
agactgttac cactccctta agtttgacct taggtcactg gaaagatgtc gagcggatcg   1200
ctcacaacca gtcggtagat gtcaagaaga gacgttgggt taccttctgc tctgcagaat   1260
ggccaacctt taacgtcgga tggccgcgag acggcaccttt aaccgagac ctcatcaccc   1320
aggttaagat caaggtcttt cacctggccc gcatggacac ccagaccagg tcccctacat   1380

```
cgtgacctgg gaagccttgg cttttgaccc ccctccctgg gtcaagccct ttgtacaccc    1440
taagcctccg cctcctcttc ctccatccgc cccgtctctc ccccttgaac ctcctcgttc    1500
gaccccgcct cgatcctccc tttatccagc cctcactcct tctctaggcg ccggaattcg    1560
ttcatggtga gcaagggcga ggagctgttc accggggtgg tgcccatcct ggtcgagctg    1620
gacggcgacg taaacggcca caagttcagc gtgtccggcg agggcgaggg cgatgccacc    1680
tacggcaagc tgaccctgaa gttcatctgc accaccggca agctgcccgt gccctggccc    1740
accctcgtga ccaccctgac ctacggcgtg cagtgcttca gccgctaccc cgaccacatg    1800
aagcagcacg acttcttcaa gtccgccatg cccgaaggct acgtccagga gcgcaccatc    1860
ttcttcaagg acgacggcaa ctacaagacc cgcgccgagg tgaagttcga gggcgacacc    1920
ctggtgaacc gcatcgagct gaagggcatc gacttcaagg aggacggcaa catcctgggg    1980
cacaagctgg agtacaacta caacagccac aacgtctata tcatggccga caagcagaag    2040
aacggcatca aggccaactt caagacccgc cacaacatcg aggacggcgg cgtgcagctc    2100
gccgaccact accagcagaa cacccccatc ggcgacggcc ccgtgctgct gcccgacaac    2160
cactacctga gcacccagtc cgccctgagc aaagacccca acgagaagcg cgatcacatg    2220
gtcctgctgg agttcgtgac cgccgccggg atcactctcg gcatggacga gctgtacaag    2280
taaagcggcc gcgactctag agtcgaggat ccgctagcta gttaattaat cgcgacgacg    2340
cgtcgccatg gtgagcaagg gcgaggagct gttcaccggg gtggtgccca tcctggtcga    2400
gctggacggc gacgtaaacg ccacaagtt cagcgtgtcc ggcgagggcg agggcgatgc    2460
cacctacggc aagctgaccc tgaagttcat ctgcaccacc ggcaagctgc ccgtgccctg    2520
gcccaccctc gtgaccaccc tgacctgggg cgtgcagtgc ttcagccgct accccgacca    2580
catgaagcag cacgacttct tcaagtccgc catgcccgaa ggctacgtcc aggagcgcac    2640
catcttcttc aaggacgacg gcaactacaa gacccgcgcc gaggtgaagt tcgagggcga    2700
caccctggtg aaccgcatcg agctgaaggg catcgacttc aaggaggacg gcaacatcct    2760
ggggcacaag ctggagtaca actacatcag ccacaacgtc tatatcaccg ccgacaagca    2820
gaagaacggc atcaaggcca acttcaagat ccgccacaac atcgaggacg gcagcgtgca    2880
gctcgccgac cactaccagc agaacacccc catcggcgac ggccccgtgc tgctgcccga    2940
caaccactac ctgagcaccc agtccgccct gagcaaagac cccaacgaga gcgcgatca    3000 catggtcctg ctggagttcg tgaccgccgc cgggatcact ctcggcatgg acgagctgta    3060
caagtaagtc gacggtatcg ataaaataaa agatttattt tagtctccag aaaagggggg    3120
gaatgaaaga ccccacctgt aggtttggca agctagaatg cataaatgta gtcttatgca    3180
atacacttgt agtcttgcaa catggtaacg atgagttagc aacatgcctt acaaggagag    3240
aaaaagcacc gtgcatgccg attggtggaa gtaaggtggt acgatcgtgc cttattagga    3300
aggcaacaga caggtctgac atggattgga cgaaccacta gatctgaagg ggggctataa    3360
aagcgatgga tccgagctcg gccctcattc tggagactct agaggccttg aattcgcggc    3420
cgcgccagtc ctccgattga ctgcgtcgcc cgggtaccgt gtatccaata aaccctcttg    3480
cagttgcatc cgacttgtgg tctcgctgtt ccttgggagg gtctcctctg agtgattgac    3540
tacccgtcag cggggtcttt catttgggg ctcgtccgg gatcgggaga ccctgccca    3600 gggaccaccg acccaccacc gggaggtaag ctggctgcct cgcgcgtttc ggtgatgacg    3660
gtgaaaacct ctgacacatg cagctcccgg agacggtcac agcttgtctg taagcggatg    3720
ccgggagcag acaagcccgt cagggcgcgt cagcgggtgt tggcgggtgt cggggcgcag    3780
```

```
ccatgaccca gtcacgtagc gatagcggag tgtatactgg cttaactatg cggcatcaga    3840
gcagattgta ctgagagtgc accatatgtc cgcccatccc gcccctaact ccgcccagtt    3900
ccgcccattc tccgcccat ggctgactaa ttttttttat ttatgcagag gccgaggccg     3960
cctcggcctc tgagctattc cagaagtagt gaggaggctt ttttggaggc ctaggctttt    4020
gcaacatatg tccgcccatc ccgcccctaa ctccgcccag ttccgcccat tctccgcccc    4080
atggctgact aattttttt atttatgcag aggccgaggc cgcctcggcc tctgagctat    4140
tccagaagta gtgaggaggc ttttttggag gcctaggctt ttgcaacata tgcggtgtga    4200
aataccgcac agatgcgtaa ggagaaaata ccgcatcagg cgctcttccg cttcctcgct    4260
cactgactcg ctgcgctcgg tcgttcggct gcggcgagcg gtatcagctc actcaaaggc    4320
ggtaatacgg ttatccacag aatcagggga taacgcagga agaacatgt gagcaaaagg    4380
ccagcaaaag gccaggaacc gtaaaaaggc cgcgttgctg gcgttttcc ataggctccg    4440
cccccctgac gagcatcaca aaaatcgacg ctcaagtcag aggtggcgaa acccgacagg    4500
actataaaga taccaggcgt ttccccctgg aagctccctc gtgcgctctc ctgttccgac    4560
cctgccgctt accggatacc tgtccgcctt tctcccttcg ggaagcgtgg cgctttctca    4620
tagctcacgc tgtaggtatc tcagttcggt gtaggtcgtt cgctccaagc tgggctgtgt    4680
gcacgaaccc cccgttcagc ccgaccgctg cgccttatcc ggtaactatc gtcttgagtc    4740
caacccggta agacacgact tatcgccact ggcagcagcc actggtaaca ggattagcag    4800
agcgaggtat gtaggcggtg ctacagagtt cttgaagtgg tggcctaact acggctacac    4860
tagaaggaca gtatttggta tctgcgctct gctgaagcca gttaccttcg gaaaaagagt    4920
tggtagctct tgatccggca aacaaaccac cgctggtagc ggtggttttt ttgtttgcaa    4980
gcagcagatt acgcgcagaa aaaaaggatc tcaagaagat cctttgatct tttctacggg    5040
gtctgacgct cagtggaacg aaaactcacg ttaagggatt ttggtcatga gattatcaaa    5100
aaggatcttc acctagatcc ttttaaatta aaaatgaagt tttaaatcaa tctaaagtat    5160
atatgagtaa acttggtctg acagttacca atgcttaatc agtgaggcac ctatctcagc    5220
gatctgtcta tttcgttcat ccatagttgc ctgactcccc gtcgtgtaga taactacgat    5280
acgggagggc ttaccatctg gccccagtgc tgcaatgata ccgcgagacc cacgctcacc    5340
ggctccagat ttatcagcaa taaaccagcc agccggaagg gccgagcgca gaagtggtcc    5400
tgcaacttta tccgcctcca tccagtctat taattgttgc cgggaagcta gagtaagtag    5460
ttcgccagtt aatagtttgc gcaacgttgt tgccattgct gcaggcatcg tggtgtcacg    5520
ctcgtcgttt ggtatggctt cattcagctc cggttcccaa cgatcaaggc gagttacatg    5580
atcccccatg ttgtgcaaaa aagcggttag ctccttcggt cctccgatcg ttgtcagaag    5640
taagttggcc gcagtgttat cactcatggt tatggcagca ctgcataatt ctcttactgt    5700
catgccatcc gtaagatgct tttctgtgac tggtgagtac tcaaccaagt cattctgaga    5760
atagtgtatg cggcgaccga gttgctcttg cccggcgtca acacgggata taccgcgcc    5820
acatagcaga actttaaaag tgctcatcat tggaaaacgt tcttcggggc gaaaactctc    5880
aaggatctta ccgctgttga gatccagttc gatgtaaccc actcgtgcac ccaactgatc    5940
ttcagcatct tttactttca ccagcgtttc tgggtgagca aaaacaggaa ggcaaaatgc    6000
cgcaaaaaag ggaataaggg cgacacggaa atgttgaata ctcatactct tcctttttca    6060
atattattga agcatttatc agggttattg tctcatgagc ggatacatat ttgaatgtat    6120
```

```
ttagaaaaat aaacaaatag gggttccgcg cacatttccc cgaaaagtgc caccctgacgt    6180 ctaagaaacc attattatca tgacattaac ctataaaaat aggcgtatca cgaggccctt    6240
tcgtcttcaa                                                           6250

<210> SEQ ID NO 110
<211> LENGTH: 1798
<212> TYPE: DNA
<213> ORGANISM: Saccharomyces cerevisiae

<400> SEQUENCE: 110
tatctggttg atcctgccag tagtcatatg cttgtctcaa agattaagcc atgcatgtct      60
aagtataagc aatttataca gtgaaactgc gaatggctca ttaaatcagt tatcgtttat     120
ttgatagttc ctttactaca tggtataacc gtggtaattc tagagctaat acatgcttaa     180
aatctcgacc ctttggaaga gatgtattta ttagataaaa aatcaatgtc ttcgcactct     240
ttgatgattc ataataactt ttcgaatcgc atggccttgt gctggcgatg gttcattcaa     300
atttctgccc tatcaacttt cgatggtagg atagtggcct accatggttt caacgggtaa     360
cggggaataa gggttcgatt ccggagaggg agcctgagaa acggctacca catccaagga     420
aggcagcagg cgcgcaaatt acccaatcct aattcaggga ggtagtgaca ataaataacg     480
atacagggcc cattcgggtc ttgtaattgg aatgagtaca atgtaaatac cttaacgagg     540
aacaattgga gggcaagtct ggtgccagca gccgcggtaa ttccagctcc aatagcgtat     600
attaaagttg ttgcagttaa aaagctcgta gttgaacttt gggcccggtt ggccggtccg     660
attttttcgt gtactggatt ccaacggggc cttttccttc tggctaacct tgagtccttg     720
tggctcttgg cgaaccagga cttttacttt gaaaaaatta gagtgttcaa agcaggcgta     780
ttgctcgaat atattagcat ggaataatag aataggacgt ttggttctat tttgttggtt     840
tctaggacca tcgtaatgat taataggac ggtcggggc atcggtattc aattgtcgag     900
gtgaaattct tggatttatt gaagactaac tactgcgaaa gcatttgcca aggacgtttt     960
cattaatcaa gaacgaaagt tagggggatcg aagatgatct ggtaccgtcg tagtcttaac    1020
cataaactat gccgactaga tcgggtggtg ttttttaat gacccactcg gtaccttacg    1080
agaaatcaaa gtctttgggt tctgggggga gtatggtcgc aaggctgaaa cttaaaggaa    1140
ttgacggaag ggcaccacta ggagtggagc ctgcggctaa tttgactcaa cacggggaaa    1200
ctcaccaggt ccagacacaa taaggattga cagattgaga gctctttctt gattttgtgg    1260
gtggtggtgc atggccgttt ctcagttggt ggagtgattt gtctgcttaa ttgcgataac    1320
gaacgagacc ttaacctact aaatagtggt gctagcattt gctggttatc cacttcttag    1380
agggactatc ggtttcaagc cgatggaagt ttgaggcaat acaggtctg tgatgccctt    1440 agaacgttct gggccgcacg cgcgctacac tgacggagcc agcgagtcta accttggccg    1500
agaggtcttg gtaatcttgt gaaactccgt cgtgctgggg atagagcatt gtaattattg    1560
ctcttcaacg aggaattcct agtaagcgca agtcatcagc ttgcgttgat tacgtccctg    1620
ccctttgtac acaccgcccg tcgctagtac cgattgaatg gcttagtgag gcctcaggat    1680
ctgcttagag aaggggggcaa ctccatctca gagcggagaa tttggacaaa cttggtcatt    1740
tagaggaact aaaagtcgta acaaggtttc cgtaggtgaa cctgcggaag gatcatta     1798

<210> SEQ ID NO 111
<211> LENGTH: 1869
<212> TYPE: DNA
<213> ORGANISM: Mus musculus
```

<400> SEQUENCE: 111

```
tacctggttg atcctgccag tagcatatgc ttgtctcaaa gattaagcca tgcatgtcta    60
agtacgcacg gccggtacag tgaaactgcg aatggctcat taaatcagtt atggttcctt   120
tggtcgctcg ctcctctcct acttggataa ctgtggtaat tctagagcta atacatgccg   180
acgggcgctg acccccttc ccggggggg atgcgtgca ttatcagatc aaaaccaacc     240
cggtgagctc cctcccggct ccggccgggg gtcgggcgcc ggcggcttgg tgactctaga   300
taacctcggg ccgatcgcac gccccccgtg cggcgacga cccattcgaa cgtctgccct    360
atcaactttc gatggtagtc gccgtgccta ccatggtgac cacgggtgac ggggaatcag   420
ggttcgattc cggagaggga gcctgagaaa cggctaccac atccaaggaa ggcagcaggc   480
gcgcaaatta cccactcccg acccggggag gtagtgacga aaataacaa tacaggactc    540
tttcgaggcc ctgtaattgg aatgagtcca ctttaaatcc tttaacgagg atccattgga   600
gggcaagtct ggtgccagca gccgcggtaa ttccagctcc aatagcgtat attaaagttg   660
ctgcagttaa aaagctcgta gttggatctt gggagcgggc gggcggtccg ccgcgaggcg   720
agtcaccgcc cgtccccgcc ccttgcctct cggcgccccc tcgatgctct tagctgagtg   780
tcccgcgggg cccgaagcgt ttactttgaa aaaattagag tgttcaaagc aggcccgagc   840
cgcctggata ccgcagctag gaataatgga ataggaccgc ggttctattt tgttggtttt   900
cggaactgag gccatgatta agagggacgg ccgggggcat tcgtattgcg ccgctagagg   960
tgaaattctt ggaccggcgc aagacggacc agagcgaaag catttgccaa gaatgttttc  1020
attaatcaag aacgaaagtc ggaggttcga agacgatcag ataccgtcgt agttccgacc  1080
ataaacgatg ccgactggcg atgcggcggc gttattccca tgacccgccg ggcagcttcc  1140
gggaaaccaa agtctttggg ttccgggggg agtatggttg caaagctgaa acttaaagga  1200
attgacggaa gggcaccacc aggagtgggc ctgcggctta atttgactca acacgggaaa  1260
cctcacccgg cccggacacg gacaggattg acagattgat agctctttct cgattccgtg  1320
ggtggtggtg catggccgtt cttagttggt ggagcgattt gtctggttaa ttccgataac  1380
gaacgagact ctggcatgct aactagttac gcgaccccg agcggtcggc gtccccaac   1440
ttcttagagg gacaagtggc gttcagccac ccgagattga gcaataacag gtctgtgatg  1500
cccttagatg tccggggctg cacgcgcgct acactgactg gctcagcgtg tgcctaccct  1560
gcgccggcag gcgcgggtaa cccgttgaac cccattcgtg atgggatcg gggattgcaa   1620
ttattcccca tgaacgagga attcccagta agtgcgggtc ataagcttgc gttgattaag  1680
tccctgccct ttgtacacac cgcccgtcgc tactaccgat tggatggttt agtgaggccc  1740
tcggatcggc cccgccgggg tcggcccacg gccctggcgg agcgctgaga agacggtcga  1800
acttgactat ctagaggaag taaaagtcgt aacaaggttt ccgtaggtga acctgcggaa  1860
ggatcatta                                                          1869
```

<210> SEQ ID NO 112
<211> LENGTH: 1869
<212> TYPE: DNA
<213> ORGANISM: Homo sapiens
<220> FEATURE:
<221> NAME/KEY: modified_base
<222> LOCATION: (27)..(27)
<223> OTHER INFORMATION: m2a--2'-o-methyladenosine (genebank # 36162)
<220> FEATURE:
<221> NAME/KEY: modified_base
<222> LOCATION: (99)..(99)

```
<223> OTHER INFORMATION: m2a--2'-o-methyladenosine
<220> FEATURE:
<221> NAME/KEY: modified_base
<222> LOCATION: (159)..(159)
<223> OTHER INFORMATION: m2a--2'-o-methyladenosine
<220> FEATURE:
<221> NAME/KEY: modified_base
<222> LOCATION: (166)..(166)
<223> OTHER INFORMATION: m2a--2'-o-methyladenosine
<220> FEATURE:
<221> NAME/KEY: modified_base
<222> LOCATION: (468)..(468)
<223> OTHER INFORMATION: m2a--2'-o-methyladenosine
<220> FEATURE:
<221> NAME/KEY: modified_base
<222> LOCATION: (484)..(484)
<223> OTHER INFORMATION: m2a--2'-o-methyladenosine
<220> FEATURE:
<221> NAME/KEY: modified_base
<222> LOCATION: (512)..(512)
<223> OTHER INFORMATION: m2a--2'-o-methyladenosine
<220> FEATURE:
<221> NAME/KEY: modified_base
<222> LOCATION: (576)..(576)
<223> OTHER INFORMATION: m2a--2'-o-methyladenosine
<220> FEATURE:
<221> NAME/KEY: modified_base
<222> LOCATION: (590)..(590)
<223> OTHER INFORMATION: m2a--2'-o-methyladenosine
<220> FEATURE:
<221> NAME/KEY: modified_base
<222> LOCATION: (668)..(668)
<223> OTHER INFORMATION: m2a--2'-o-methyladenosine
<220> FEATURE:
<221> NAME/KEY: modified_base
<222> LOCATION: (1031)..(1031)
<223> OTHER INFORMATION: m2a--2'-o-methyladenosine
<220> FEATURE:
<221> NAME/KEY: modified_base
<222> LOCATION: (1383)..(1383)
<223> OTHER INFORMATION: m2a--2'-o-methyladenosine
<220> FEATURE:
<221> NAME/KEY: modified_base
<222> LOCATION: (1678)..(1678)
<223> OTHER INFORMATION: m2a--2'-o-methyladenosine
<220> FEATURE:
<221> NAME/KEY: modified_base
<222> LOCATION: (1832)..(1832)
<223> OTHER INFORMATION: m2a--2'-o-methyladenosine
<220> FEATURE:
<221> NAME/KEY: modified_base
<222> LOCATION: (1850)..(1850)
<223> OTHER INFORMATION: m2a--2'-o-methyladenosine
<220> FEATURE:
<221> NAME/KEY: modified_base
<222> LOCATION: (116)..(116)
<223> OTHER INFORMATION: um
<220> FEATURE:
<221> NAME/KEY: modified_base
<222> LOCATION: (121)..(121)
<223> OTHER INFORMATION: um
<220> FEATURE:
<221> NAME/KEY: modified_base
<222> LOCATION: (172)..(172)
<223> OTHER INFORMATION: um
<220> FEATURE:
<221> NAME/KEY: modified_base
<222> LOCATION: (428)..(428)
<223> OTHER INFORMATION: um
<220> FEATURE:
<221> NAME/KEY: modified_base
<222> LOCATION: (627)..(627)
<223> OTHER INFORMATION: um
<220> FEATURE:
<221> NAME/KEY: modified_base
<222> LOCATION: (799)..(799)
<223> OTHER INFORMATION: um
<220> FEATURE:
<221> NAME/KEY: modified_base
```

-continued

```
<222> LOCATION: (1288)..(1288)
<223> OTHER INFORMATION: um
<220> FEATURE:
<221> NAME/KEY: modified_base
<222> LOCATION: (1326)..(1326)
<223> OTHER INFORMATION: um
<220> FEATURE:
<221> NAME/KEY: modified_base
<222> LOCATION: (1442)..(1442)
<223> OTHER INFORMATION: um
<220> FEATURE:
<221> NAME/KEY: modified_base
<222> LOCATION: (1668)..(1668)
<223> OTHER INFORMATION: um
<220> FEATURE:
<221> NAME/KEY: modified_base
<222> LOCATION: (1804)..(1804)
<223> OTHER INFORMATION: um
<220> FEATURE:
<221> NAME/KEY: modified_base
<222> LOCATION: (174)..(174)
<223> OTHER INFORMATION: cm 2'-o-cytidine
<220> FEATURE:
<221> NAME/KEY: modified_base
<222> LOCATION: (462)..(462)
<223> OTHER INFORMATION: cm
<220> FEATURE:
<221> NAME/KEY: modified_base
<222> LOCATION: (517)..(517)
<223> OTHER INFORMATION: cm
<220> FEATURE:
<221> NAME/KEY: modified_base
<222> LOCATION: (797)..(797)
<223> OTHER INFORMATION: cm
<220> FEATURE:
<221> NAME/KEY: modified_base
<222> LOCATION: (1391)..(1391)
<223> OTHER INFORMATION: cm
<220> FEATURE:
<221> NAME/KEY: modified_base
<222> LOCATION: (1703)..(1703)
<223> OTHER INFORMATION: cm
<220> FEATURE:
<221> NAME/KEY: modified_base
<222> LOCATION: (436)..(436)
<223> OTHER INFORMATION: gm
<220> FEATURE:
<221> NAME/KEY: modified_base
<222> LOCATION: (509)..(509)
<223> OTHER INFORMATION: gm
<220> FEATURE:
<221> NAME/KEY: modified_base
<222> LOCATION: (601)..(601)
<223> OTHER INFORMATION: gm
<220> FEATURE:
<221> NAME/KEY: modified_base
<222> LOCATION: (644)..(644)
<223> OTHER INFORMATION: gm
<220> FEATURE:
<221> NAME/KEY: modified_base
<222> LOCATION: (683)..(683)
<223> OTHER INFORMATION: gm
<220> FEATURE:
<221> NAME/KEY: modified_base
<222> LOCATION: (867)..(867)
<223> OTHER INFORMATION: gm
<220> FEATURE:
<221> NAME/KEY: modified_base
<222> LOCATION: (1328)..(1328)
<223> OTHER INFORMATION: gm
<220> FEATURE:
<221> NAME/KEY: modified_base
<222> LOCATION: (1447)..(1447)
<223> OTHER INFORMATION: gm
<220> FEATURE:
<221> NAME/KEY: modified_base
<222> LOCATION: (1490)..(1490)
<223> OTHER INFORMATION: gm
<220> FEATURE:
```

```
<221> NAME/KEY: modified_base
<222> LOCATION: (1639)..(1639)
<223> OTHER INFORMATION: gm
<220> FEATURE:
<221> NAME/KEY: modified_base
<222> LOCATION: (1248)..(1248)
<223> OTHER INFORMATION: x 3-(3-amino-3-carboxypropyl)
      -1-methylpseudouridine

<400> SEQUENCE: 112
tacctggttg atcctgccag tagcatatgc ttgtctcaaa gattaagcca tgcatgtcta      60
agtacgcacg gccggtacag tgaaactgcg aatggctcat taaatcagtt atggttcctt    120
tggtcgctcg ctcctctccc acttggataa ctgtggtaat tctagagcta atacatgccg    180
acgggcgctg accccttcg cggggggat gcgtgcattt atcagatcaa aaccaacccg      240
gtcagcccct ctccggcccc ggccgggggg cgggcgccgg cggctttggt gactctagat    300
aacctcgggc cgatcgcacg ccccccgtgg cggcgacgac ccattcgaac gtctgcccta    360
tcaactttcg atggtagtcg ccgtgcctac catggtgacc acgggtgacg gggaatcagg    420
gttcgattcc ggagagggag cctgagaaac ggctaccaca tccaaggaag gcagcaggcg    480
cgcaaattac ccactcccga cccggggagg tagtgacgaa aaataacaat acaggactct    540
ttcgaggccc tgtaattgga atgagtccac tttaaatcct ttaacgagga tccattggag    600
ggcaagtctg gtgccagcag ccgcggtaat tccagctcca atagcgtata ttaaagttgc    660
tgcagttaaa aagctcgtag ttggatcttg ggagcgggcg ggcggtccgc cgcgaggcga    720
gccaccgccc gtccccgccc cttgcctctc ggcgcccct cgatgctctt agctgagtgt    780
cccgcgggc ccgaagcgtt tactttgaaa aaattagagt gttcaaagca gcccgagcc     840
gcctggatac cgcagctagg aataatggaa taggaccgcg gttctatttt gttggttttc    900
ggaactgagg ccatgattaa gagggacggc cggggcatt cgtattgcgc cgctagaggt    960
gaaattcttg gaccggcgca agacggacca gagcgaaagc atttgccaag aatgttttca   1020
ttaatcaaga acgaaagtcg gaggttcgaa gacgatcaga taccgtcgta gttccgacca   1080
taaacgatgc cgaccggcga tgcggcggcg ttattcccat gacccgccgg gcagcttccg   1140
ggaaaccaaa gtctttgggt tccgggggga gtatggttgc aaagctgaaa cttaaaggaa   1200
ttgacggaag ggcaccacca ggagtggagc ctgcggctta atttgactca acacgggaaa   1260
cctcacccgg cccggacacg gacaggattg acagattgat agctctttct cgattccgtg   1320
ggtggtggtg catggccgtt cttagttggt ggagcgattt gtctggttaa ttccgataac   1380
gaacgagact ctggcatgct aactagttac gcgaccccg agcggtcggc gtccccaac     1440
ttcttagagg gacaagtggc gttcagccac ccgagattga gcaataacag gtctgtgatg   1500
ccccttagatg tccggggctg cacgcgcgct acactgactg gctcagcgtg tgcctaccct   1560
acgccggcag gcgcgggtaa cccgttgaac cccattcgtg atggggatcg gggattgcaa   1620
ttattcccca tgaacgagga attcccagta agtgcgggtc ataagcttgc gttgattaag   1680
tccctgccct ttgtacacac cgcccgtcgc tactaccgat tggatggttt agtgaggccc   1740
tcggatcggc cccgccgggg tcggcccacg gccctggcgg agcgctgaga agacggtcga   1800
acttgactat ctagaggaag taaaagtcgt aacaaggttt ccgtaggtga acctgcggaa   1860
ggatcatta                                                           1869
```

METHODS OF IDENTIFYING SYNTHETIC TRANSCRIPTIONAL AND TRANSLATIONAL REGULATORY ELEMENTS, AND COMPOSITIONS RELATING TO SAME

CROSS REFERENCE TO RELATED APPLICATIONS

Under 35 USC § 120, this application is a continuation application of U.S. application Ser. No. 10/182,329 filed Dec. 9, 2002, now U.S. Pat. No. 7,183,395; which is a 35 USC § 371 National Stage Application of PCT Application No. PCT/US01/02733 filed Jan. 26, 2001; which claims the benefit under 35 USC § 119(e) to U.S. Application Ser. No. 60/261,312 filed Jan. 12, 2001, U.S. application Ser. No. 60/230,956 filed Sep. 7, 2000, U.S. application Ser. No. 60/230,852 filed Sep. 7, 2000, U.S. application Ser. No. 60/207,804 filed May 30, 2000, U.S. application Ser. No. 60/186,496 filed Mar. 2, 2000 and U.S. application Ser. No. 60/178,816 filed Jan. 28, 2000, now abandoned. The disclosure of each of the prior applications is considered part of and is incorporated by reference in the disclosure of this application.

GRANT INFORMATION

This invention was made in part with government support under Grant No. MCB9982574 awarded by the National Science Foundation. The government has certain rights in this invention.

BACKGROUND OF THE INVENTION

1. Field of the Invention

This invention relates to methods for producing nucleotide sequences having regulatory functions using cellular selection of random nucleotide sequences, and to the sequences so produced.

2. Background Information

Every eukaryotic gene has a core promoter that resides at the extreme 5' end of its transcription unit. Most core promoters contain common recognition sequences such as the TATA box and GC-rich motifs, which allow binding of RNA polymerase, the enzyme required for the synthesis of messenger RNA on DNA templates. The core promoter is essential for initiation of transcription. However, it alone usually does not contain all the information necessary for the modulated expression of a gene in different contexts in the developing or behaving organism. This contextual information is frequently provided by other regulatory elements such as enhancers and silencers, which reside in the gene at locations that are proximal to the core promoter either upstream or downstream from an initiation site of RNA transcription, and can be several kilobases away from the core promoter. In addition, the mRNA molecules transcribed from gene sequences contain translational regulatory elements, which regulate production of a polypeptide from the mRNA. For example, the mRNA can contain an internal ribosome entry site (IRES) sequence, which effects the manner in which ribosomes bind to an mRNA and initiate translation, and does not require interaction of the ribosome with the 5' end of an mRNA transcript. Thus, an IRES element can confer an additional level of regulation on gene expression.

It is not completely understood how combinations of regulatory elements interact with the core promoter to achieve the remarkable contextual diversity of gene expression that exists during animal development and tissue regeneration, as well as the mis-regulation associated with pathological conditions such as neoplastic disorders. Understanding how this diversity comes about is a major goal of modern biology, and achievement of this goal would accelerate progress in a number of areas in cell biology, development, and medicine. For instance, synthetic promoters or IRESes that function in a tissue specific manner, and that are selected as markers of either healthy or diseased tissues, can be useful in diagnostic or therapeutic procedures, and in drug development. Such applications for these promoters also can extend our understanding of a variety of diseases, thus providing a means to develop therapeutic interventions.

Eukaryotic promoters are complex and frequently contain combinations of several transcriptional regulatory elements. These DNA motifs are recognized by specific proteins (transcription factors) that bind to the element and regulate transcription of a particular gene. Hundreds of DNA segments that participate in the regulation of transcription of genes in eukaryotic systems have been characterized. However, these elements and their corresponding transcription factors generally have been analyzed only as individual units, for example, as to how an element and its associated transcription factors regulate the expression of a particular gene in a specific context. However, the rules by which regulatory elements function either by themselves or in combination with other elements in the many genes in which these elements are found are not well understood.

An example of this complexity is provided by the specific interaction of activator protein 1 (AP-1) with the TPA responsive gene regulatory element (TRE), which is present in the promoter and enhancer regions of many eukaryotic genes. The TRE is bound by members of the fos and jun families of transcriptional regulatory proteins, which are recruited in a number of regulatory situations in gene expression, particularly under conditions involving the integration of growth factor signals. A TRE can be present in a regulatory region of a gene that is expressed only in the kidney during its differentiation or, alternatively, in a gene that is expressed constitutively by neural cell precursors. It is not known, however, how the element is selected to function in a very specific context in each of these different environments or, for example, whether other elements are involved in modulating the function of a TRE such as the ability to repress (or potentiate) activity from the TRE.

Compared to transcriptional control sequences, little is known about translational control sequences. Some IRESes have been identified in viruses, and more recently cellular mRNA sequences having IRES activity have been identified. Unlike transcriptional regulatory elements, however, small modular elements having translational regulatory activity, including IRES activity, have not been identified.

Currently, there is no general systematic framework for analyzing the anatomy of promoters, enhancers, IRESes and other transcriptional and translational regulatory elements, and it is unknown how the combination of several common transcriptional and translational motifs present in many of these regulatory elements function cooperatively to create unique patterns of gene expression. For example, particular variations of nucleotides within a regulatory element may be able to function well in the context of a specific companion element, while other variants of the motif may be able to override the influences of neighboring elements. Thus, a need exists for methods to identify functional transcriptional and translation regulatory elements. The present invention satisfies this need and provides additional advantages.

SUMMARY OF THE INVENTION

The present invention relates to methods to create, select and assemble transcriptional or translational regulatory elements, including, for example, promoter, enhancer and IRES elements, and methods to examine the ability of such regulatory elements to modulate transcription or translation in eukaryotic cells. A method of the invention can utilize, for example, an expression vector construct, which allows the insertion of relatively small nucleotide sequences (oligonucleotides) to be examined for regulatory activity, and for the systematic testing and isolation of such a regulatory element.

A method of the invention provides an analytic tool and an engine of discovery for transcriptional and translational regulatory sequences, and can provide a basis for diagnostic applications. As such, the present invention also provides regulatory oligonucleotides that can be used in expression vectors for controlling gene expression in diagnostic and therapeutic applications, and provides vectors useful for identifying such transcriptional and translational regulatory elements.

The present invention relates to a method of identifying an oligonucleotide having transcriptional or translational regulatory activity in a eukaryotic cell. Such a method can be performed, for example, by integrating an oligonucleotide to be examined for transcriptional or translational regulatory activity into a eukaryotic cell genome, wherein the oligonucleotide is operatively linked to an expressible polynucleotide, and detecting a change in the level of expression of the expressible polynucleotide in the presence of the oligonucleotide as compared to the absence of the oligonucleotide. The expressible polynucleotide generally contains a cloning site such that the oligonucleotide can be operatively linked to the expressible polynucleotide by insertion into the cloning site, and also can contain a transcription initiator sequence. The expressible polynucleotide generally is a reporter polypeptide, which can be a fluorescent polypeptide, an antibiotic resistance polypeptide, a cell surface protein marker, an enzyme, or a peptide tag.

In one embodiment, the invention provides a method to identify an oligonucleotide having transcriptional regulatory activity, for example, promoter activity, enhancer activity, or silencer activity. The expressible polynucleotide generally is operatively linked minimal promoter, for example, a TATA box, a minimal enkephalin promoter, or a minimal SV40 early promoter. The expressible polypeptide can comprise a monocistronic reporter cassette, which encodes a single reporter polypeptide, or can be a dicistronic reporter cassette, which includes, in operative linkage, a regulatory cassette comprising a minimal promoter and a cloning site, a nucleotide sequence encoding a first reporter polypeptide, a spacer sequence comprising an internal ribosome entry site (IRES), and a nucleotide sequence encoding a second reporter polypeptide, whereby an oligonucleotide to be examined for transcriptional regulatory activity is operatively linked to the dicistronic reporter cassette by insertion into the cloning site. The expressible polynucleotide can be contained in a vector, which can be a plasmid based vector such as the vectors exemplified by SEQ ID NO: 2 and SEQ ID NO: 3, or can be contained in a retroviral vector such as the vectors exemplified by SEQ ID NO: 1 and SEQ ID NO: 9.

The oligonucleotide to be examined for transcriptional activity can be a synthetic oligonucleotide, for example, a random oligonucleotide sequence such an oligonucleotide in a library of randomized oligonucleotides, or a variegated oligonucleotide that is based on, but different from a known oligonucleotide such as a known transcriptional regulatory element. The oligonucleotide to be examined for transcriptional activity also can be a portion of an oligonucleotide fragment of genomic DNA.

In another embodiment, the invention provides a method to identify an oligonucleotide having translational regulatory activity, for example, a translational enhancer or inhibitor or an IRES element. In such a method, the expressible polynucleotide includes a promoter, which generally is a strong promoter such as an RSV promoter or CMV promoter or the like. The expressible polynucleotide can include a monocistronic reporter cassette or dicistronic reporter cassette. Preferably, where the oligonucleotide is to be examined for IRES activity, the expressible polynucleotide includes a dicistronic reporter cassette, which contains, in operative linkage, a regulatory cassette comprising a promoter, a nucleotide sequence encoding a first reporter polypeptide, a spacer sequence comprising a cloning site, and a nucleotide sequence encoding a second reporter polypeptide, whereby an oligonucleotide to be examined for IRES activity is operatively linked to the nucleotide sequence encoding the second reporter polypeptide by insertion into the cloning site. The expressible polynucleotide can be contained in a vector, for example, a retroviral vector such as that exemplified by SEQ ID NO: 109.

The oligonucleotide to be examined for translational activity can be a synthetic oligonucleotide, for example, a random oligonucleotide sequence such an oligonucleotide in a library of randomized oligonucleotides, or a variegated oligonucleotide that is based on, but different from a known oligonucleotide such as a known translational regulatory element. The oligonucleotide to be examined for translational activity also can be a portion of a cDNA encoding a 5' untranslated region of an mRNA, or can be an oligonucleotide fragment of genomic DNA. In addition, the oligonucleotide to be examined for translational regulatory activity can be based on a sequence complementary to an oligonucleotide sequence of rRNA, preferably an un-base paired oligonucleotide sequence of rRNA, including, for example, a variegated population of oligonucleotide sequences derived from an oligonucleotide sequence complementary to an un-base paired region of a rRNA.

In one embodiment, a method of the invention is performed such that the oligonucleotide to be examined for transcriptional or translational regulatory activity is operatively linked to the expressible polynucleotide prior to integrating into the eukaryotic cell genome. In another embodiment, the expressible polynucleotide is an endogenous polynucleotide in the eukaryotic cell genome, and the oligonucleotide to be examined for regulatory activity is introduced into a cell containing the expressible polynucleotide and operatively linked to the endogenous polynucleotide, for example, by homologous recombination.

In yet another embodiment, the eukaryotic cell is a cell of a transgenic non-human eukaryote, wherein the cell contains a transgene. The transgene can be, for example, a recombinase recognition site that is positioned with respect to an endogenous expressible polynucleotide such that an oligonucleotide inserted into the site is operatively linked to the polynucleotide. The transgene also can be a heterologous expressible polynucleotide, which is stably maintained in the eukaryotic cell genome, and can contain a cloning site for insertion of the oligonucleotide to be examined. In one embodiment, the oligonucleotide is an oligonucleotide to be examined for transcriptional regulatory activity, and the transgene is a dicistronic reporter cassette comprising, in operative linkage, a regulatory cassette comprising a minimal promoter and a cloning site, a first reporter cassette, a spacer sequence comprising an internal ribosome entry site (IRES), and a second reporter cassette, whereby the oligonucleotide is operatively linked to the dicistronic reporter cassette by insertion into the cloning site. In another embodiment, the oligonucleotide is an oligonucleotide to be examined for translational regulatory activity, and the transgene is a dicistronic reporter cassette comprising, in operative linkage, a regulatory cassette comprising a promoter, a first reporter cassette, a spacer sequence comprising a cloning site, and a second reporter cassette, whereby the oligonucleotide is operatively linked to the second cistron by insertion into the cloning site.

A method of the invention also can be performed by cloning a library of oligonucleotides to be examined for transcriptional or translation regulatory activity into multiple copies of an expression vector comprising an expressible polynucleotide, whereby the oligonucleotides are operatively linked to the expressible polynucleotide, thereby obtaining a library of vectors; contacting the library of vectors with eukaryotic cells under conditions such that the vectors are introduced into the cell and integrate into a chromosome in the cells; and detecting expression of an expressible polynucleotide operatively linked to an oligonucleotide at a level other than a level of expression of the expressible polynucleotide in the absence of the oligonucleotide. The eukaryotic cells can be any eukaryotic cells, including insect, yeast, amphibian, reptilian, avian or mammalian cells. Preferably, the cells are mammalian cells, including, for example, neuronal cells, fibroblasts, hepatic cells, bone marrow cells, bone marrow derived cells, muscle cells and epithelial cells. The library of oligonucleotides can be, for example, a library of randomized oligonucleotides, a library of variegated oligonucleotides based on a selected oligonucleotide sequence, or a library of genomic DNA fragments.

In one embodiment, the oligonucleotide is an oligonucleotide to be examined for transcriptional regulatory activity, and the expressible polynucleotide comprises, in operative linkage, a regulatory cassette comprising a minimal promoter and a cloning site, and a reporter cassette, whereby the oligonucleotide is operatively linked to the expressible polynucleotide by insertion into the cloning site. In another embodiment, the oligonucleotide is an oligonucleotide to be examined for transcriptional regulatory activity, and the expressible polynucleotide comprises a dicistronic reporter cassette comprising, in operative linkage, a regulatory cassette comprising a minimal promoter and a cloning site, a nucleotide sequence encoding a first reporter polypeptide, a spacer sequence comprising an internal ribosome entry site (IRES), and a nucleotide sequence encoding a second reporter polypeptide, whereby the oligonucleotide is operatively linked to the dicistronic reporter cassette by insertion into the cloning site. The expressible polynucleotide can be contained in a vector, for example, a plasmid vector as exemplified by SEQ ID NO: 2 and SEQ ID NO: 3 or a retroviral vector as exemplified by SEQ ID NO: 1 and SEQ ID NO: 9.

A method of identifying an oligonucleotide having transcriptional regulatory activity can further include selecting a population of cells expressing the expressible polynucleotide operatively linked to an oligonucleotide at a level other than a level of expression of the expressible polynucleotide in the absence of the oligonucleotide. Furthermore, the method can further include isolating the operatively linked oligonucleotide. As such, the present invention provides an isolated synthetic transcriptional regulatory element obtained by the disclosed method, and further provides a recombinant nucleic acid molecule comprising a plurality of operatively linked isolated transcriptional regulatory elements, which can be the same or different.

In still another embodiment, the oligonucleotide is an oligonucleotide to be examined for translational regulatory activity, and the expressible polynucleotide is a dicistronic reporter cassette comprising, in operative linkage, a regulatory cassette comprising a promoter, a nucleotide sequence encoding a first reporter polypeptide, a spacer sequence comprising a cloning site, and a nucleotide sequence encoding a second reporter polypeptide, whereby the oligonucleotide is operatively linked to the second cistron by insertion into the cloning site. The expressible polynucleotide can be contained in a vector, for example, a plasmid vector or a retroviral vector as exemplified by SEQ ID NO: 109. The method can include further selecting a population of cells expressing the expressible polynucleotide operatively linked to an oligonucleotide at a level other than a level of expression of the expressible polynucleotide in the absence of the oligonucleotide, and can include a step of isolating the operatively linked oligonucleotide. As such, the invention provides an isolated synthetic translational regulatory element, for example, an IRES element, which is obtained using the disclosed method, as well as a recombinant nucleic acid molecule comprising a plurality of operatively linked isolated translational regulatory elements, which can be the same or different.

The present invention also relates to an integrating expression vector useful for identifying an oligonucleotide having transcriptional or translational regulatory activity. An integrating expression vector for identifying a transcriptional regulatory element can contain, for example, in operative linkage in a 5' to 3' orientation, a long terminal repeat (LTR) containing a immediate early gene promoter, an R region, a U5 region, a truncated gag gene comprising sequences required for retrovirus packaging, a dicistronic reporter cassette including a nucleotide sequence encoding a first reporter polypeptide, a spacer sequence containing an IRES, a nucleotide sequence encoding a second reporter polypeptide, and a regulatory cassette containing a cloning site and a minimal promoter, and an LTR. The first and second polypeptides independently can be selected from a fluorescent polypeptide such as green fluorescent protein, cyan fluorescent protein, red fluorescent protein, or an enhanced form thereof, an antibiotic resistance polypeptide such as puromycin N-acetyltransferase, hygromycin B phosphotransferase, neomycin (aminoglycoside) phosphotransferase, and the Sh ble gene product, a cell surface protein marker such as the cell surface protein marker is neural cell adhesion molecule (N-CAM), an enzyme such as β-galactosidase, chloramphenicol acetyltransferase, luciferase, and alkaline phosphatase, or a peptide tag such as a c-myc peptide, a polyhistidine, or the like. For example, the first reporter polypeptide can be puromycin N-acetyltransferase and the second reporter polypeptide can enhanced green fluorescent protein; or the first reporter polypeptide can be puromycin N-acetyltransferase and the second reporter polypeptide can be N-CAM.

The cloning site can be any sequence that facilitates insertion of an oligonucleotide in operative linkage to the expressible polynucleotide, for example, a restriction endonuclease recognition site or a multiple cloning site containing a plurality of such sites, or recombinase recognition site such as a lox sequence or an att sequence. The minimal promoter can be any minimal promoter, for example, a TATA box, a minimal enkephalin promoter, or a minimal SV40 early promoter. Examples of integrating expression vectors of the invention are set forth as SEQ ID NO: 1 and SEQ ID NO: 9, and additional expression vectors, which can integrate into a cell genome, are exemplified by SEQ ID NO: 2 and SEQ ID NO: 3.

An integrating expression vector for identifying an oligonucleotide having translational regulatory activity, particularly IRES activity, can contain, for example, in operative linkage in a 5' to 3' orientation, a long terminal repeat (LTR) containing a immediate early gene promoter, an R region, a U5 region, a truncated gag gene comprising sequences required for retrovirus packaging, a dicistronic reporter cassette including a nucleotide sequence encoding a first reporter polypeptide, a spacer sequence comprising a cloning site, a nucleotide sequence encoding a second reporter polypeptide, and a regulatory cassette comprising a promoter, and an LTR. The first and second reporter polypeptide independently can be any reporter polypeptide as disclosed herein or otherwise known in the art. For example, the first reporter polypeptide can be enhanced green fluorescent protein and the second reporter polypeptide can enhanced cyan fluorescent protein. An example of an integrating expression vector is provided by SEQ ID NO: 109.

A method of the invention provides a means to identify a transcriptional regulatory element. According to one embodiment, oligonucleotides in a library of synthetic DNA sequence elements are positioned next to a minimal (core) promoter and screened for activity in mammalian cells using a high throughput selection strategy. The selection process can identify a variety of individual transcriptional regulatory oligonucleotide sequences that can enhance gene expression from the minimal eukaryotic promoter. In another embodiment, a selected transcriptionally active element or an oligonucleotide to be examined for transcriptional regulatory activity and a known regulatory motif is combined to produce promoter/enhancer element cassettes. By varying the order, number and spacing of elements in these cassettes and subsequently selecting for promoter activity, transcriptional regulatory elements having desirable characteristics can be isolated and the rules that govern functional interactions between elements can be determined.

A method of the invention also provides a means to identify an oligonucleotide that confers a transcriptional regulatory function on an operatively linked polynucleotide in a eukaryotic cell. The method can be performed, for example, by operatively linking an oligonucleotide to be examined for transcriptional regulatory activity to an expressible polynucleotide, the expression of which can be driven by a minimal promoter, and detecting an increased or decreased level of transcription of the polynucleotide due to the presence of the oligonucleotide. The transcriptional activity due to the oligonucleotide can be examined in vitro or in vivo in a cell in culture or in an organism. In one embodiment, the transcriptional activity is examined in a cell in vivo following integration of the construct comprising the oligonucleotide and expressible polynucleotide into a chromosome in the cell. Such a method provides a means to identify a regulatory element that can act by inducing a local change in the DNA or chromatin conformation, for example, DNA bending, which can increase access of the transcription machinery to the sequence to be transcribed. Such regulatory elements cannot be detected using methods that rely exclusively on identifying a protein/DNA interaction as a means to identify a regulatory element.

A method of identifying an oligonucleotide that confers transcriptional regulatory activity also can be performed by providing an expression vector, which contains a reporter cassette comprising a nucleotide sequence encoding a reporter molecule, wherein the reporter cassette is operatively linked to a regulatory cassette comprising a minimal promoter element; cloning a library of randomized oligonucleotides into multiple copies of the expression vector, wherein an oligonucleotide of the library is operatively linked to a minimal promoter element, and wherein the randomized oligonucleotide can potentially function as a transcriptional regulatory sequence, to form a library of vectors that differ in the potential regulatory sequences; transfecting eukaryotic cells with the library of different vectors to form transfected eukaryotic host cells; culturing the transfected eukaryotic cells under conditions suitable for integration of the vector into the host cell and expression of the reporter molecule; selecting a population of transfected eukaryotic cells that express the reporter molecule; and obtaining from the selected population of cells, transcriptional regulatory sequences, which can be a library of transcriptional regulatory sequences.

Optionally, a reporter cassette useful for identifying a transcriptional regulatory element according to a method of the invention is a dicistronic construct that includes the nucleotide sequence encoding the first reporter molecule, and also includes a second nucleotide sequence encoding a second selectable marker, which is different from the first reporter molecule. Preferably, the dicistronic construct includes an IRES element in the intercistronic sequence. Such a construct facilitates the identification and isolation of transcriptional regulatory oligonucleotides.

A method of the invention also provides a means to identify a translational regulatory element, including a translational enhancer, an IRES element, and the like. According to one embodiment, a complex library of synthetic DNA sequence elements is positioned in an intervening sequence between first and second nucleotide sequences that encode first and second reporter molecules in a dicistronic reporter cassette, and screened for translational regulatory activity in a eukaryotic cell, for example, a mammalian cell, optionally using a high throughput selection strategy. Using such a method, a variety of regulatory oligonucleotide sequences that initiate cap-independent translation of the second reporter molecule and, therefore, function as IRES sequences have been identified. In another embodiment, a selected translational regulatory element is combined with a known regulatory motif such that, by varying the order, number and spacing of elements in a reporter cassette and subsequently selecting for expression, translational regulatory elements having desirable characteristics can be isolated and the rules that govern functional interactions between elements can be determined.

A method of the invention provides a means to identify an oligonucleotide that confers a translational regulatory function on an operatively linked polynucleotide in a eukaryotic cell. Such a method can be performed, for example, by operatively Unking an oligonucleotide to be examined for translational regulatory activity to an expressible polynucleotide, which includes or encodes the elements generally required for translation such as start and stop codons (i.e., a cistron), and detecting an increased or decreased level of translation of the polynucleotide due to the presence of the oligonucleotide. The translational activity due to the oligonucleotide can be examined in vitro or in vivo in a cell in culture or in an organism. In one embodiment, the translational activity is examined in a cell in vivo following integration of the construct comprising the oligonucleotide and expressible polynucleotide into a chromosome in the cell.

A method of identifying an oligonucleotide having translational regulatory activity also can be practiced by providing an expression vector comprising a dicistronic reporter cassette, which includes a first nucleotide sequence encoding a first reporter protein and a second nucleotide sequence encoding a second reporter protein, which is different from the first reporter protein, wherein the dicistronic reporter cassette is operatively linked to a regulatory cassette comprising a promoter element, and wherein the reporter cassette contains an intercistronic spacer nucleotide sequence between the first and second encoding nucleotide sequences such that an oligonucleotide to be examined for translational regulatory activity can be introduced into the spacer sequence and is operatively linked to the second nucleotide sequence; cloning the oligonucleotides of a library of randomized oligonucleotides into multiple copies of said expression vector, wherein an oligonucleotide is introduced into the spacer nucleotide sequence, and wherein the randomized oligonucleotide potentially functions as a translational regulatory sequence, to form a library of vectors differing in said potential regulatory sequences; transfecting eukaryotic cells with the library of different vectors to form transfected eukaryotic host cells; culturing the transfected eukaryotic cells under conditions suitable for integration of the vector into the host cell and expression of said first and second reporter proteins; selecting a population of transfected eukaryotic cells that express said second reporter protein; and obtaining from the selected population of cells oligonucleotides that function as translational regulatory sequences. A reporter protein (and encoding nucleotide sequence) useful in a method or composition of the invention can be any reporter protein, as disclosed herein, including a fluorescent, luminescent or chemiluminescent protein, an enzyme, a receptor (or ligand), a protein can confers resistance to an antibiotic or other toxic agent, and the like. The reporter molecule can be selected, for example, based on its cost, convenience, availability or other such factor, and generally provides a means to identify and, if desired, isolate a cell expressing the reporter molecule.

The present invention also provides isolated synthetic transcriptional or translational regulatory oligonucleotides, which can be identified and isolated using a method as disclosed herein. Such synthetic regulatory oligonucleotides can be useful for regulating the expression of an operatively linked polynucleotide, and can be particularly useful for conferring tissue specific, developmental stage specific, or the like expression of the polynucleotide, including constitutive or inducible expression. A synthetic regulatory oligonucleotide of the invention also can be a component of an expression vector or of a recombinant nucleic acid molecule comprising the regulatory oligonucleotide operatively linked to an expressible polynucleotide.

Accordingly, the present invention provides compositions comprising an oligonucleotide of the invention. In one embodiment, the composition is a vector, which generally is an expression vector and can be an integrating expression vector that, upon being introduced into a cell, can integrate into the genome of the cell, particularly a eukaryotic cell. As such, the invention also provides a host cell containing a synthetic transcriptional or translational regulatory oligonucleotide of the invention, which can be operatively linked to a heterologous polynucleotide. Also provided is a recombinant nucleic acid molecule, which contains a transcriptional or translational regulatory element of the invention operatively linked to an expressible polynucleotide, which is heterologous to the regulatory element.

The present invention also provides systems, which can be in kit form and are useful for practicing aspects of the present invention. The kit generally contains an oligonucleotide of the invention or contains a reagent for identifying a transcriptional or translational regulatory element according to a method of the invention. In one embodiment, the kit contains a synthetic regulatory oligonucleotide, which can be an isolated form or can be a component of a vector or a recombinant nucleic acid molecule. The kit also can contain a plurality of synthetic transcriptional or translational regulatory oligonucleotides or combinations thereof, which, optionally, contain additional sequences that facilitate linking the regulatory oligonucleotide to a second nucleotide sequence, which can be a vector, for example. Such a plurality of synthetic regulatory elements in kit form provides a convenient means to select a regulatory element having desired characteristics, for example, tissue specific expression or a low level of constitutive expression or other characteristic. In another embodiment, the kit contains a vector for identifying a transcriptional or translational regulatory element, for example, an integrating expression vector.

BRIEF DESCRIPTION OF THE DRAWINGS

FIGS. 2 A to 2C illustrate maps of various expression vectors useful for identifying an oligonucleotide regulatory element.

FIG. 5 shows the complementary sequence matches between YAP1 or p150 leader sequences and 18S rRNA. SEQ ID NOS: are indicated. Vertical lines indicate base pairing and open circles represent GU base pairing. The longest uninterrupted stretches of complementarity for each match are indicated by the shaded nucleotides.

FIG. 6A provides a linear representation of the 18S rRNA, the vertical lines below the linear representation are sites at which selected IRES modules share 8 or 9 nucleotides of complementarity with the to 18S rRNA sequence.

FIG. 6B shows a secondary structure of the 18S rRNA, and the dark bars indicate the positions of the complementary sequence matches to selected IRES modules of the invention.

DETAILED DESCRIPTION OF THE INVENTION

Figure 1:
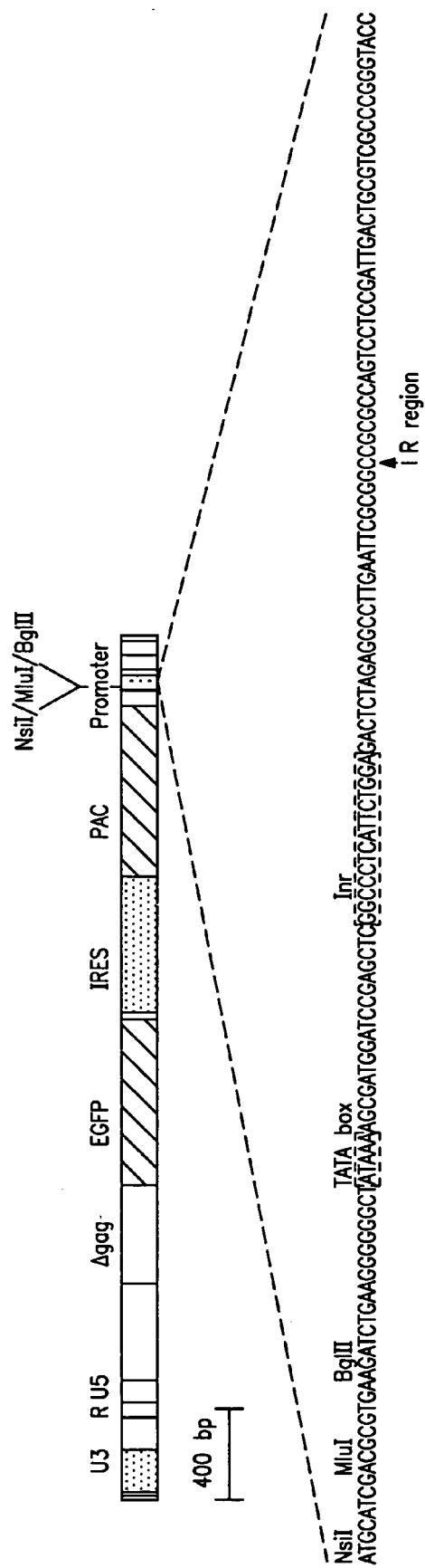
FIG. 1 illustrates a portion of the MESVR/EGFP*/IRESpacPro(ori) vector (nucleotides 3592 to 3726 of SEQ ID NO: 1), including the upstream long terminal repeat (LTR) U3 region, which contains the RSV immediate early gene promoter (R) to drive high levels of viral RNA genome production and the U5 sequence. Δgag indicates region of truncation of the group specific antigen gene; EGFP indicates enhanced green fluorescent protein; IRES indicates internal ribosome entry site; PAC indicates puromycin N-acetyltransferase coding sequence. Dotted lines indicate an expanded view of the synthetic promoter (Promoter) located in the downstream LTR U3 region. This promoter contains a multiple cloning site (Nsi I-Bgl II), TATA box and consensus initiator (Inr) sequences. The position at which the synthetic promoter fuses into the downstream R region is indicated.

The present invention provides methods for identifying synthetic transcriptional and translational regulatory elements, vectors useful for identifying such regulatory elements, and isolated regulatory elements, which comprise oligonucleotide sequences that, when present in a gene expression context in a eukaryotic cell, can confer a regulatory function onto the gene or a polynucleotide encoded by the gene. The gene segment or other expressible polynucleotide can be in any expression construct engineered for expression in a eukaryotic cell, particularly in the form of a chromosome-associated polynucleotide, which is subject to the nuances of complexity associated with gene expression in a chromosome as compared, for example, an episomal (extrachromosomal) element. A chromosomal context often is a consequence of a gene therapy procedure, wherein the transgene integrates into the chromosome.

A method of identifying a transcriptional regulatory element can be performed in various ways, as disclosed herein (see, also, Edelman et al., *Proc. Natl. Acad. Sci. USA*, 97:3038-3043, 2000, which is incorporated herein by reference). In one embodiment, an oligonucleotide to be examined for transcriptional regulatory activity is operatively linked to an expressible polynucleotide, which is or can be operatively linked to a minimal promoter, and a change in the level of expression of the polynucleotide identifies the oligonucleotide as a transcriptional regulatory oligonucleotide. As used herein, the term "transcriptional regulatory oligonucleotide" or "transcriptional regulatory element" or the like refers to a nucleotide sequence that can effect the level of transcription of an operatively linked polynucleotide. Thus, the term encompasses oligonucleotide sequences that increase the level of transcription of a polynucleotide, for example, a promoter element or an enhancer element, or that decrease the level of transcription of a polynucleotide, for example, a silencer element. As disclosed herein, a transcriptional regulatory element can be constitutively active or inducible, which can be inducible from an inactive state or from a basal state, and can be tissue specific or developmental stage specific, or the like.

As disclosed herein, the present methods provide a means for identifying and isolating a translational regulatory element that confers tissue specific or inducible translation on an operatively linked expressible polynucleotide. As used herein, the term "tissue specific," when used in reference to a translational regulatory element, means a nucleotide sequence that effects translation of an operatively linked expressible polynucleotide in only one or a few cell types. As used herein, the term "inducible," when used in response to a translational regulatory element, means a nucleotide sequence that, when present in a cell exposed to an inducing agent, effects an increased level of translation of an operatively linked expressible polynucleotide as compared to the level of translation, if any, in the absence of an inducing agent.

The term "inducing agent" is used to refer to a chemical, biological or physical agent that effects translation from an inducible translational regulatory element. In response to exposure to an inducing agent, translation from the element generally is initiated de novo or is increased above a basal or constitutive level of expression. Such induction can be identified using the methods disclosed herein, including detecting an increased level of a reporter polypeptide encoded by the expressible polynucleotide that is operatively linked to the translational regulatory element. An inducing agent can be, for example, a stress condition to which a cell is exposed, for example, a heat or cold shock, a toxic agent such as a heavy metal ion, or a lack of a nutrient, hormone, growth factor, or the like; or can be exposure to a molecule that affects the growth or differentiation state of a cell such as a hormone or a growth factor. As disclosed herein, the translational regulatory activity of an oligonucleotide can be examined in cells that are exposed to particular conditions or agents, or in cells of a particular cell type, and oligonucleotide that have translational regulatory activity in response to and only under the specified conditions or in a specific cell type can be identified.

As used herein, the term "expressible polynucleotide" is used broadly herein to refer to a nucleotide sequence that can be transcribed or translated. Generally, an expressible polynucleotide is a polydeoxyribonucleotide, which can be transcribed in whole or in part into a polyribonucleotide, or is a polyribonucleotide that can be translated in whole or in part into a polypeptide. The expressible polynucleotide can include, in addition to a transcribed or translated sequence, additional sequences required for transcription such as a promoter element, a transcription start site, a polyadenylation signal, and the like; or for translation such as a start codon, a stop codon and the like; or can be operatively linked to such sequences, which can be contained, for example, in a vector into which the polynucleotide is inserted. As such, the term "cistron" also is used herein to refer to an expressible polynucleotide that includes all or substantially all of the elements required for expression of an encoded polypeptide. Examples of expressible polynucleotides include nucleotide sequences encoding a reporter polypeptide or other selectable marker, or a nucleotide sequence encoding a polypeptide of interest, for example, a polypeptide that is to be expressed in a cell as a means to produce the polypeptide in a convenient and commercially useful manner, or as part of a gene therapy treatment.

An oligonucleotide to be examined for transcriptional (or translational) activity can be operatively linked to an expressible polynucleotide, which, for example, can encode a reporter molecule. As used herein, the term "operatively linked" or "functionally adjacent" means that a regulatory element, which can be a synthetic regulatory oligonucleotide of the invention or an oligonucleotide to be examined for such activity, is positioned with respect to a transcribable or translatable nucleotide sequence such that the regulatory element can effect its regulatory activity. An oligonucleotide having transcriptional enhancer activity, for example, can be located at any distance, including adjacent to or up to thousands of nucleotides away from, and upstream or downstream from the promoter, which can be a minimal promoter element, and nucleotide sequence to be transcribed, and still exert a detectable effect on the level of expression of an encoded reporter molecule. In comparison, a translational regulatory element generally is positioned within about 1 to 500 nucleotides, particularly within about 1 to 100 nucleotides of a translation start site. For a variety of considerations such as convenience of manipulations, and subsequent use of discrete promoter/enhancer constructs identified by the present invention, an oligonucleotide to be examined for transcriptional enhancer activity generally is positioned relatively close to the minimal promoter element, for example, within about 1 to 100 nucleotides, preferably within about 3 to 50 nucleotides of the promoter.

The term "operatively linked" also is used herein with respect to a first and second polypeptide (or peptide) to refer to encoding sequences that are linked in frame such that a fusion polypeptide can be produced. Similarly, the term is used to refer to two or more cistrons of an expressible polynucleotide that are transcribed as a single RNA molecule, which can contain, for example, an IRES element of the invention in an intercistronic position.

A method of identifying a transcriptional regulatory element can be performed using an expression vector, which contains a reporter cassette comprising a nucleotide sequence encoding at least a first reporter molecule, wherein the reporter cassette is operatively linked to a regulatory cassette comprising a minimal promoter element, is used. The reporter cassette functions to indicate (report) that the reporter molecule has been expressed by means of expression of the detectable reporter molecule. The reporter cassette is expressed under the control of (operatively linked to) the regulatory cassette, which also contains cloning sites for the introduction of an oligonucleotide to be examined for transcriptional regulatory activity, and further contains a minimal promoter element such that, upon introduction of a regulatory oligonucleotide, expression of the reporter cassette is altered.

A library of randomized oligonucleotides to be examined for transcriptional regulatory activity can be provided, and one or more individual members of the library can be cloned into multiple copies of the regulatory cassette of the expression vector. The oligonucleotide to be examined for transcriptional regulatory activity is introduced such that it is operatively linked to the minimal promoter element in the regulatory cassette and, therefore, has the potential to function as a transcriptional regulatory element. In this way, a library of different constructs, which can be contained in a vector, is formed, each construct differing in the introduced potential regulatory oligonucleotide sequence.

The oligonucleotide sequences to be examined for transcriptional (or translational) regulatory activity also can be sequences isolated from genomic DNA (or mRNA) of a cell. For example, oligonucleotides to be examined for transcriptional regulatory activity can be obtained using an antibody that is specific for a particular transcription factor such as an anti-TATA box binding protein antibody such that nucleotide sequences bound to the TATA box binding protein are isolated. The isolated sequences then can be amplified and examined for transcriptional regulatory activity using a method as disclosed herein. Similarly, transcriptionally active regions of genomic DNA can be obtained using an antibody that specifically binds acetylated histone H4, which is associated with unwound regions of chromosomal DNA. Since such chromosomal regions are associated with transcriptional activity, this method provides a means to enrich for oligonucleotide sequences that are involved in transcriptional regulation. Methods and reagents for isolating transcriptionally active regions of chromosomal DNA are well known (see, for example, Orlando and Paro, *Cell* 75:1187-1198, 1993; and Holmes and Tjian, *Science*, 288:867-870, 2000, each of which is incorporated herein by reference) and commercially available (for example, anti-acetyl histone H4 antibody, Upstate Biotechnology; anti-TFIID (TATA binding protein) antibody, Santa Cruz Biotechnology).

Oligonucleotide to be examined for translational regulatory activity also can be, for example, cDNA sequences encoding 5' UTRs of cellular mRNAs, including a library of such cDNA molecules. Furthermore, as disclosed herein, translational regulatory elements identified according to a method of the invention, including synthetic IRES elements, have been found to be complementary to oligonucleotide sequences of ribosomal RNA (rRNA; see FIG. 6), particularly to un-base paired oligonucleotide sequences of rRNA, which are interspersed among double stranded regions that form due to hybridization of self-complementary sequences within rRNA (see FIG. 7B). Accordingly, oligonucleotides to be examined for translational regulatory activity, including IRES activity, can be designed based on their being complementary to an oligonucleotide sequence of rRNA, particularly to an un-base paired oligonucleotide sequence of rRNA such as a yeast, mouse or human rRNA (SEQ ID NOS: 110, 111 or 112, respectively; see, also, GenBank Accession Nos. V01335, X00686, X03205, respectively, each of which is incorporated herein by reference). In addition, oligonucleotides to be examined for translational regulatory activity can be a library of variegated oligonucleotide sequences (see, for example, U.S. Pat. No. 5,837,500), which can be based, for example, on a translational regulatory element as disclosed herein or identified using a method of the invention, or on an oligonucleotide sequence complementary to an un-base paired region of a rRNA.

The effect of an introduced oligonucleotide on transcription of the reporter molecule can be examined in vitro or in vivo, including in a cell in culture or in a cell in an organism. Generally, the expression of the reporter molecule from the minimal promoter is determined, then the effect of an introduced oligonucleotide on the level of expression is determined. Expression from the minimal promoter can be determined prior to introducing the element or can be determined in a parallel study. For example, an in vitro transcription reaction can be used to determine the level of expression of the reporter in the presence or absence of the oligonucleotide, wherein a difference in the levels of expression indicates that the oligonucleotide has transcriptional regulatory activity. In one embodiment, the in vitro transcription reactions are performed in a high throughput format, for example, in the wells of a plate or in discrete identifiable positions in a microarray, for example, on a silicon wafer or glass slide or the like.

In another embodiment, the oligonucleotide is examined in a cell, particularly a eukaryotic cell, which can be a cell in culture or a cell in an organism, for example, a transgenic non-human eukaryotic organism. The construct comprising the oligonucleotide to be examined operatively linked to the reporter cassette and regulatory cassette is introduced into the cell by any of various transfection methods. Preferably, the construct is contained in a vector, which generally is an expression vector, although the elements required for expression also can be part of the construct. Eukaryotic cells are transfected with a library of different vectors to form transfected eukaryotic host cells. Transfection can be performed using methods as disclosed herein or otherwise known in the art. In a particular embodiment, the construct comprising the reporter and regulatory cassettes is contained in a viral vector such as a retroviral vector, which is introduced into a target cell by viral infection. The transfected cells then can be cultured under conditions suitable for the vector to integrate into the host cell, and for the reporter molecule to be expressed if the oligonucleotide has transcriptional regulatory activity. A selection step then can be performed such that cells expressing the reporter molecule are identifiable, and the regulatory sequence in the selected cells can be isolated.

A method of identifying a translational regulatory element, including a synthetic translational enhancer or a synthetic IRES sequence, can be performed similarly. As disclosed herein, a method of the invention provides a means to identify a translational regulatory element that can enhance the level of translation or can reduce or inhibit the level of translation of an operatively linked expressible polynucleotide. A translational enhancer or inhibitor can be identified, for example, by operatively linking the oligonucleotide to be examined for translational regulatory activity to an expressible polynucleotide, which can, in turn, be operatively linked to a strong promoter, wherein an increase or decrease in the level of translation in the presence of the oligonucleotide as compared to its absence identifies the oligonucleotide as a translational regulatory element. The construct comprising the oligonucleotide to be examined and the regulatory and reporter cassettes, which can be in a vector such as an expression vector, can include a dicistronic reporter cassette, which is operatively linked to a regulatory cassette comprising a strong promoter element. The dicistronic reporter cassette contains a first nucleotide sequence encoding a first reporter molecule and a second nucleotide sequence, which is operatively linked to the first nucleotide sequence and encodes a second reporter protein, which is different from the first reporter protein. The reporter cassette functions to indicate (report) that the first or second reporter protein or both have been expressed, by means of transcription and translation of the nucleotide sequences encoding the first and second reporter proteins.

The first and second nucleotide sequence in the dicistronic reporter cassette are separated by an intercistronic sequence, which facilitates the introduction and operative linkage of an oligonucleotide sequence to be examined for IRES or other translational regulatory activity. The intercistronic spacer nucleotide sequence generally contains a site for cloning the oligonucleotide sequence to be examined for translational regulatory activity, particularly IRES activity, in a position to effect translation of the second cistron. Upon introduction of a nucleotide sequence that functions as an IRES, the second nucleotide sequence (cistron) is translated to produce an expressed second reporter protein.

Following the rules for transcription of mRNA and translation of protein, the second nucleotide sequence of the dicistronic reporter cassette is located 3' (downstream) from the termination codon for the first encoded protein, and 5' (upstream) from the transcription termination and polyadenylation signals of the mRNA transcript. The result is a dicistronic construct which, upon transcription, forms an mRNA transcript that encodes two polypeptides, the first and second reporter molecules.

Currently, no general methodology exists for synthesizing, selecting, and varying the content of transcriptional or translational regulatory elements in the context of a eukaryotic chromosome. Moreover, there is relatively little information as to whether either natural or synthetic promoters, when coupled to a fluorescent marker, can be used to sort cells that may be characteristic of a particular phenotype. However, methods have been reported that are either related to the disclosed regulatory element selection technique or represent attempts at making synthetic promoters. For example, Li et al. (*Nature Biotechnol.* 17:241-245, 1999) describe building synthetic promoters that function in muscle cells. These myogenic promoters were made one at a time by multimerizing known elements such as the E-box, the serum response element (SRE), and the binding site for MEF-1 (a muscle-specific transcription factor) into arrays. Various combinations of these sites were then cloned upstream of a minimal promoter and luciferase gene cassette, and transfected individually into cell lines derived from muscle in order to score their relative promoter activity. Eventually, after screening several of these luciferase constructs, a panel of "super-promoters", which work better than the promoters from known muscle-specific genes, was assembled. However, Li et al do not describe an EGFP/FACS sorting technique. As such, an advantage of the present invention is that one can screen over a million candidates prior to confirming their activity in a luciferase system, whereas the promoter technique described by Li et al. merely makes and analyzes promoter activity one at a time.

Asoh et al. (*Troc. Natl. Acad. Sci. USA* 91:6982-6986, 1994) described a technique for cloning random fragments of genomic DNA in a polyoma virus in order to up-regulate the expression of the large T antigen. This assay for enhancer activity was based on the ability of the virus to replicate more efficiently, and the activity of putative enhancer elements was scored by increased neomycin resistance. The rationale of this method is that an active enhancer sequence would increase the ability of an enhancerless polyoma virus to replicate, and this would be scored as a neomycin resistant cell. However, the selection system of Asoh et al. differs from the present invention in that increased viral replication is selected for rather than enhanced transcription. Furthermore, there is no testing of these sequences for promoter activity in an independent system.

Others have described using the DNA binding properties of promoter elements to develop techniques that isolate elements using nuclear extracts from cells. Such techniques select motifs based on their ability to bind proteins. These techniques allow for pre-selecting sequences that have binding activity as a basis for further testing of such selected sequences for promoter activity. Previous work describes such an enrichment of DNA binding elements, including the CAST method (Funk et al., *Proc. Acad. Natl. Sci., USA* 89:9484-9488, 1992) (Gruffat et al., *Nucl. Acids Res.* 22:1172-1178, 1994), the MuST method (Nallur et al., *Proc. Acad. Natl. Sci., USA* 93:1184-1189, 1996) and the FROGS method (Mead et al., *Proc. Acad. Natl. Sci., USA* 95:11251-11256, 1998). The CAST technique was one of the first methods used to isolate DNA binding sites from a pool of random DNA sequences using the gel mobility shift assay. The MuST technique is a multiplex selection approach, in which a library of potential DNA binding elements that may function in gene transcription, is subjected to one or more rounds of protein binding using nuclear extracts from different mammalian cell types. This assay gives a profile of all the elements that are capable of binding nuclear factors and represents an extremely useful "up-front" procedure that would complement our selection approach.

The CAST and MuST techniques, however, fall short of the presently disclosed methods in that CAST and MuST do not provide an activity assay to demonstrate whether the elements that are selected in such DNA binding procedures function to regulate transcription in the cells from which the nuclear extracts are prepared. The FROGS technique is similar to CAST and MuST, exploiting the advantage of selecting only those elements that bind to proteins. As such, these methods do not test the selected elements for regulatory activity, and bias against finding elements that can function as regulatory elements, but do not actually bind to proteins.

Another method, NOMAD, (Rebatchouk et al., *Proc. Acad. Natl. Sci., USA* 93:10891-10896, 1996), involves the design of a modular reporter vector system that is applied to the enterprise of shuffling promoter elements in order to determine the effects of ordering, spacing, and inversions of such elements on promoter activity. The goal of the NOMAD procedure is to provide extreme flexibility in the ability to clone DNA in a directional fashion and also to easily modify and rearrange these sequences. Thus, the NOMAD vector system provides an alternative to the disclosed successive element ligation procedure used to ligate promoter elements in a defined order and polarity.

Dirks et al., U.S. Pat. No. 6,060,273, describe methods and compositions for identifying IRES elements. Although Dirks et al., describe IRES nucleotide sequences of viral, cellular or synthetic origin, they appear to refer only to synthesized nucleotide sequences as compared to those isolated from a biological source, but do not disclose screening synthetic oligonucleotides such as a library of random oligonucleotides as disclosed herein. Singer et al. (*Genes Devel.* 4:636-645, 1990) describe a method for selecting a basal promoter in yeast, but do not describe identifying cis enhancer elements or the use of the use of a method such as FACS sorting. Bell et al. (*Yeast* 15:1747-1759, 1999) describe selection for yeast promoter using EGFP and FACS sorting, but do not describe screening random sequences for promoter activity.

A method of the invention can be useful for quickly and conveniently screening a large number of oligonucleotides to identify those having transcriptional or translational regulatory activity. For example, a library of randomized oligonucleotides can be cloned into multiple vectors comprising the dicistronic reporter cassette such that the oligonucleotides are operatively linked by insertion into the spacer sequence in a position to function as an IRES and initiate translation of the second reporter protein. Eukaryotic cells can be transfected with the library of different vectors to form transfected eukaryotic host cells, in which the vector can integrate into the host cell genome and in which an oligonucleotide having IRES activity, for example, can effect the level of expression of the second reporter molecule. Transfected cells expressing the reporter molecules then can be selected based on expression of the reporter molecule and the identified IRES oligonucleotide sequence can be isolated.

The oligonucleotides identified herein as having transcriptional or translational regulatory activity provide modules that can be used alone or combined with each other to produce desired activities. For example, concatemers of the identified IRES elements can vastly increase polypeptide expression from an associated cistron, including concatemers of 2, 5, 10, 20, 35, 50 or 75 copies of an IRES element, which independently can be multiple copies of the same or different IRES elements, and which can be operatively linked adjacent to each other or separated by spacer nucleotide sequences that can vary from 1 to about 100 nucleotides in length. The capacity to drive high levels of protein expression has many applications for large scale protein production as, for example, in bulk manufacturing of drugs such as those produced in the biotechnology industry, nutritional proteins, industrial enzymes, and the like. Furthermore, when present in polycistronic constructs, IRES elements can be used to co-express proteins in a cell. For example, a dicistronic construct can contain a first cistron that encodes a polypeptide of interest such as a polypeptide drug or the like and a second cistron encoding a reporter polypeptide, which is expressed from an IRES element. Such a construct provides a means to select cells that contain the first cistron, which encodes the polypeptide of interest, thus minimizing the presence of contaminating cells that do not express the polypeptide and facilitating isolation of the polypeptide.

The disclosed elements also can bind to cellular factors, for example, an IRES element can bind ribosomes in a cell, thus modifying or inhibiting its translational activity. As such, the elements can be used to modulate (or inhibit) transcription or translation of a gene product, for example, during an industrial process or as part of a therapeutic procedure. In particular, the elements can be used as a genetic "toxin" to inhibit specific transcription or translation in a target cell. As disclosed herein, introduction of a translational regulatory element identified according to a method of the invention as having translational enhancing activity can reduce the level of translation when introduced into a cell. While no mechanism for this action is proposed herein or, in fact, relevant to using such an element to effect translational activity in a cell, one possibility is that the element can bind to and sequester trans-acting translational regulatory factors such as eukaryotic initiation factors or the like, similar to effects seen with transcriptional regulatory elements when introduced into cells, or can bind to rRNA such that the rRNA is unavailable to effect translation. Thus, by introducing a translational regulatory element having translational enhancing activity or IRES activity into a eukaryotic cell, the translational activity in the eukaryotic cell can be reduced or inhibited. Conversely, by introducing a translational regulatory element having translational inhibitory activity into a eukaryotic cell, translational activity in the cell is increased due, for example, to the sequestering of a trans-acting factor that otherwise binds to an endogenous translational inhibitory sequence in the cell to inhibit translation.

A dicistronic reporter cassette can be used for identifying a transcriptional or translational regulatory element, depending on the particular configuration as disclosed herein. For example, for identifying a transcriptional regulatory element according to a method of the invention, the dicistronic reporter cassette can contain a defined IRES element in the intercistronic spacer sequence, and the dicistronic reporter cassette is operatively linked, generally, to a minimal promoter element such that, upon introduction of a nucleotide sequence having transcriptional regulatory activity, transcription of the dicistronic cassette occurs. As compared to the level of transcription of the dicistronic reporter cassette in the absence of an oligonucleotide to be examined for transcriptional regulatory activity, the level of transcription can increase due to the oligonucleotide or can decrease due to the oligonucleotide. Since the promoter for the dicistronic reporter cassette is a minimal promoter, it can be difficult to identify a decrease in transcriptional activity due to the oligonucleotide. However, the ability of the oligonucleotide to decrease transcriptional activity, for example, to act as a silencer, can be confirmed by examining the effect of the oligonucleotide on a corresponding construct having a strong promoter, for example, an RSV promoter, in place of the minimal promoter.

In comparison, for identifying an IRES element according to a method of the invention, the dicistronic reporter cassette is operatively linked, generally, to a strong promoter, and the oligonucleotide sequence to be examined for IRES activity is introduced into the spacer sequence between the first and second cistron. The use of a dicistronic reporter cassette allows for the sequential selection of cells expressing the first reporter molecule, followed by selection of cells expressing the second reporter molecule provides an additional level of confirmation that regulation of expression arises due to the contribution of the regulatory oligonucleotide and not, for example, due to an artifact, such as rearrangement of the vector sequences during transfection to produce a functional promoter or functional IRES, or other event that can lead to expression of the reporter molecule outside the control of the introduced regulatory oligonucleotide and the promoter element of the vector.

A dicistronic reporter cassette for identifying a transcriptional regulatory element, for example, can allow for antibiotic selection (puromycin) as a first (or second) reporter selection, followed (or preceded) by fluorescence-activated cell sorting (FACS) selection using a fluorescent reporter such as enhanced green fluorescent protein (EGFP). A dicistronic reporter cassette for identifying an IRES element, for example, can allow for FACS with EGFP as a first reporter selection, followed by a second FACS selection using enhanced cyan fluorescent protein (ECFP) as the second reporter selection. Other combinations of reporter molecules are disclosed herein or can otherwise be selected by the skilled artisan depending, for example, on cost, convenience or availability of the reporter molecule or the means for identifying (detecting) its expression.

A synthetic transcriptional or translational regulatory element can be identified by screening, for example, a library of oligonucleotides containing a large number of different nucleotide sequences. The oligonucleotides can be variegated oligonucleotide sequences, which are based on but different from a known transcriptional or translational regulatory element, for example, an oligonucleotide complementary to an un-base paired sequence of a rRNA, or can be a random oligonucleotide library. The use of randomized oligonucleotides provides the advantage that no prior knowledge is required of the nucleotide sequence, and provides the additional advantage that completely new regulatory elements can be identified. Methods for making a combinatorial library of nucleotide sequences or a variegated population of nucleotide sequences or the like are well known in the art (see, for example, U.S. Pat. No. 5,837,500; U.S. Pat. No. 5,622,699; U.S. Pat. No. 5,206,347; Scott and Smith, *Science* 249:386-390, 1992; Markland et al., *Gene* 109:13-19, 1991; O'Connell et al., *Proc. Natl. Acad. Sci., USA* 93:5883-5887, 1996; Tuerk and Gold, *Science* 249:505-510, 1990; Gold et al., *Ann. Rev. Biochem.* 64:763-797, 1995; each of which is incorporated herein by reference).

A regulatory element can be of various lengths from a few nucleotides to several hundred nucleotides. Thus, the length of an oligonucleotide in a library of oligonucleotides to be screened can be any length, including oligonucleotides as short as about 6 nucleotides or as long as about 100 nucleotides or more. Generally, the oligonucleotides to be examined are about 6, 12, 18, 30 nucleotides or the like in length. The complexity of the library, i.e., the number of unique members, also can vary, although preferably the library has a high complexity so as to increase the likelihood that regulatory sequences are present. Libraries can be made using any method known in the art, including, for example, using a oligonucleotide synthesizer and standard oligonucleotide synthetic chemistry. Where the oligonucleotides are to be incorporated into a vector, the library complexity depends in part on the size of the expression vector population being used to clone the random library and transfect cells. Thus, a theoretical limitation for the complexity of the library also relates to utilization of the library content by the recipient expression vector and by th£ transfected cells, as well as by the complexity that can be obtained using a particular method of oligonucleotide synthesis.

A reporter cassette useful for identifying a transcriptional or translational regulatory element is a module that includes one or more nucleotide sequences encoding one or more reporter molecules, respectively. The reporter cassette is operatively linked to an adjacent regulatory cassette such that expression of the reporter cassette is under the control of the regulatory cassette. The term "cassette" is used herein to refer to a nucleotide sequence that can be easily and conveniently manipulated by recombinant DNA methods such that it can be linked, including operatively linked, to one or more other nucleotide sequences or can be inserted into or removed from a vector. For example, a cassette can include restriction endonuclease recognition and cleavage sites or recombinase recognition and cleavage sites, which provide a means for conveniently manipulating the cassette, for example, by insertion into a vector.

As used herein, the term "reporter cassette" refers to a nucleotide sequence that includes the signals for encoding a complete reporter gene product, including the signals for initiation of translation, nucleotides encoding the structural protein, translation termination codons, and 3' sequence information to ensure a functional mRNA transcript can be produced following activation of transcription of a mRNA. As disclosed herein, a reporter cassette can be monocistronic, wherein it encodes a single reporter molecule, can be dicistronic, wherein it encodes two reporter molecules, or polycistronic, wherein it contains more than two cistrons.

For the isolation of synthetic transcriptional regulatory elements, the reporter cassette generally is monocistronic or dicistronic and, when dicistronic, contains an IRES element in the intercistronic spacer sequence between the cistrons encoding the reporter molecules. For the isolation of synthetic IRES sequences, the reporter cassette generally is a dicistronic reporter cassette, wherein the oligonucleotide to be examined for IRES activity is introduced into the intercistronic spacer sequence, which otherwise lacks an IRES element. In a dicistronic reporter cassette, the second nucleotide sequence encoding a second reporter protein is operatively linked to the first nucleotide sequence encoding the first reporter protein. The first and second coding sequences are separated by an intercistronic spacer nucleotide sequence, into which an oligonucleotide sequence to be examined for IRES activity can be introduced in operative linkage to the second coding sequence.

An oligonucleotide to be examined for transcriptional or translational regulatory element can be operatively linked, as appropriate, using any recombinant DNA methodology for combining nucleotide sequences. The method can vary depending upon the particular nucleotide sequences, including whether the cassettes are contained within a vector. Particularly useful methods for inserting an oligonucleotide in operative linkage include the use of restriction endonucleases, for example, by including a restriction endonuclease recognition site or multiple cloning site in appropriate proximity to the regulatory or reporter cassette of interest and flanking the oligonucleotide to be introduced therein, or by including a site specific recombinase recognition site such as a topoisomerase recognition site, a lox site, or an att site at the appropriate location. By contacting the nucleotide sequences in the presence of the appropriate enzyme, i.e. a restriction endonuclease, topoisomerase, Cre recombinase, Int recombinase, or the like, the oligonucleotide can be operatively linked with respect to the regulatory and reporter cassettes.

The reporter molecules generally are polypeptides that can be expressed under the conditions of the assay being utilized and the expression of which is detectable. Where a method of the invention is performed in a cell, for example, the reporter molecule can confer a detectable or selectable phenotype on cells expressing the molecule. In a method utilizing a dicistronic reporter cassette, the encoded first and second reporter proteins generally are different from each other, thus providing independent selection criteria. Reporter molecules, also referred to as selectable markers, are well known in the art and include, a fluorescent protein such as green fluorescent protein (GFP) and enhanced and modified forms of GFP; an enzyme such P-galactosidase, chloramphenicol acetyltransferase, luciferase, or alkaline phosphatase; an antibiotic resistance protein such as puromycin N-acetyltransferase, hygromycin B phosphotransferase, neomycin (aminoglycoside) phosphotransferase, or the Zeocin$^R$ gene product (Stratagene); a cell surface protein marker such as N-CAM or a polypeptide that is expressed on a cell surface and has been modified to contain a tag peptide such as a polyhistidine sequence (e.g., hexahistidine), a V5 epitope, a c-myc epitope; a hemagglutinin A epitope, a FLAG epitope, or the like.

Expression of the reporter molecule can be detected using the appropriate reagent, for example, by detecting light emission upon addition of luciferin to a luciferase reporter molecule, or by detecting binding of nickel ion to a polypeptide containing a polyhistidine tag. Furthermore, the reporter molecule can provide a means of isolating the expressed reporter molecule or a cell expressing the reporter molecule. For example, where the reporter molecule is a polypeptide that is expressed on a cell surface and that contains a c-myc epitope, an anti-c-myc epitope antibody can be immobilized on a solid matrix and cells, some of which express the tagged polypeptide, can be contacted with the matrix under conditions that allow selective binding of the antibody to the epitope. Unbound cells can be removed by washing the matrix, and bound cells, which express the reporter molecule, can be eluted and collected. Methods for detecting such reporter molecules and for isolating the molecules, or cells expressing the molecules, are well known to those in the art (see, for example, Hopp et al., *BioTechnology* 6:1204, 1988; U.S. Pat. No. 5,011,912; each of which is incorporated herein by reference).

Fluorescent reporter markers are particularly convenient for use in the compositions and methods of the invention because they allow the selection of cells containing the expressed reporter protein by fluorescence activated cell sorting (FACS). Similarly, proteins that confer antibiotic resistance are particularly useful as selectable markers because only cells expressing the antibiotic resistance protein can survive exposure to the particular antibiotic. Cell surface protein markers, which are expressed on the surface of a eukaryotic cell, represent a large class of proteins suitable for use as reporter proteins in the present invention. The surface marker can be selected, for example, using an antibody specific for the protein, or using a ligand (or receptor) that specifically interacts with and binds to the cognate cell surface receptor (or ligand). Cells expressing a cell surface marker can be isolated, for example, by a panning method, which utilizes immobilized antibodies (or ligands or receptors) that selectively bind to the cell surface marker, or by a FACS method, in which case the antibody or ligand is fluorescently labeled and, therefore, labels the cell expressing the cell surface marker by specifically binding to the marker. The cell adhesion molecule, N-CAM, is an example of a cell surface marker useful according to the present invention.

As disclosed herein, a reporter cassette can be operatively linked to a regulatory cassette, thereby providing a construct useful for identifying a transcriptional or translational regulatory element according to a method of the invention. Generally, the term "regulatory cassette" refers to a nucleotide sequence required for transcription of a reporter cassette. Thus, a regulatory cassette generally includes a promoter element, which can be a minimal promoter or strong promoter depending on the purpose for which a construct comprising the regulatory cassette is to be used, and can contain additional transcriptional regulatory elements, provided that the elements of the regulatory cassette do not interfere with the use of a construct comprising the regulatory cassette to identify a regulatory element according to a method of the invention.

A regulatory cassette useful in a method of identifying a transcriptional regulatory element, for example, is a nucleotide sequence comprising a minimal promoter element. In addition, the regulatory cassette can contain a sequence that facilitates introduction of an oligonucleotide to be examined for transcriptional activity into the regulatory cassette in an operatively linked manner. Such a sequence can be a restriction endonuclease recognition site, recombinase recognition site, and the like. A minimal promoter is a nucleotide sequence that allows initiation of transcription by RNA polymerase II, and can be up-regulated by operative linkage of a regulatory element, particularly an oligonucleotide transcriptional regulatory element according to the present invention. The regulatory cassette and operatively linked reporter cassette can be in an isolated form, or can be contained in a vector.

A regulatory cassette useful in a method of identifying an IRES element is a nucleotide sequence comprising a promoter element. Generally, but not necessarily, the promoter in such a regulatory element is a strong promoter, and preferably the construct comprising the regulatory cassette and operatively linked reporter cassette is contained in a vector. Since an oligonucleotide to be examined for translational regulatory activity must be transcribed, a site for introducing the oligonucleotide into the regulatory cassette/reporter cassette construct is positioned downstream of the transcription start site and, in one embodiment, is positioned in an intercistronic spacer sequence of a dicistronic reporter cassette.

An oligonucleotide having IRES activity generally is positioned in an intercistronic position, from which it can exert its translational activity, and, as disclosed herein, can be at various distances from the translation start site of the second cistron. An oligonucleotide to be examined for IRES activity can be many hundreds of nucleotides from the transcriptional promoter, which generally is positioned upstream (5') of the first cistron of a dicistronic reporter cassette. As such, it should be recognized that such an oligonucleotide to be examined for translational regulatory activity is operatively linked to the second cistron such that an oligonucleotide having IRES activity can be identified by its effecting translation of the second cistron.

A promoter element generally acts as a substrate for RNA polymerase II, in combination with additional protein factors, to initiate transcription. A variety of promoter sequences are known in the art. Thus, promoters useful in a regulatory cassette as disclosed herein include the adenovirus promoter TATA box, an SP1 site (GGGCGG; SEQ ID NO: 4), a minimal enkephalin gene promoter (MEK), an SV40 early minimal promoter, a TRE/AP-1 element (TGACTCA; SEQ ID NO: 5), an erythroid cell GATA element (GATAGA; SEQ ID NO: 6), a myeloid tumor element NF-κB binding site (GGGAATTCCCC; SEQ ID NO: 7), a cyclic AMP response element (TGACGTCA; SEQ ID NO: 8), and the like. Because an active transcriptional promoter can comprise a variety of elements, the present invention can involve the use of a regulatory cassette with additional features so as to preferentially select regulatory oligonucleotides having an activity that depends upon the included feature. For example, the regulatory cassette can include a consensus transcription initiator sequence, or can include a transcription initiator sequence derived from a tissue specific gene, thereby increasing the tissue specificity of the selected regulatory oligonucleotide.

As disclosed herein, a construct comprising a regulatory cassette operatively linked to a reporter cassette is useful for identifying transcriptional and translational regulatory elements. In one embodiment, the construct is contained in a vector, which generally is an expression vector that contains certain components, but otherwise can vary widely in sequence and in functional element content. In general, the vector contains a reporter cassette, which can be a dicistronic reporter cassette, operatively linked to a regulatory cassette, which contains a minimal promoter element or a strong promoter element, depending on the specific type of regulatory element that is to be identified. The vector also can contain sequences that facilitate recombinant DNA manipulations, including, for example, elements that allow propagation of the vector in a particular host cell (e.g., a bacterial cell, insect cell or mammalian cell), selection of cells containing the vector (e.g., antibiotic resistance genes for selection in bacterial or mammalian cells), and cloning sites for introduction of reporter genes or the elements to be examined (e.g., restriction endonuclease sites or recombinase recognition sites).

Preferably, the regulatory cassette and operatively linked reporter cassette, which can be monocistronic or dicistronic, are contained in an expression vector that is characterized, in part, in that it can integrate into a eukaryotic chromosome. Such a construct provides the advantage that the activity of an oligonucleotide can be examined in the context or milieu of the whole eukaryotic chromosome. A chromosome offers unique and complex regulatory features with respect to the control of gene expression, including translation. As such, it is advantageous to have a system and method for obtaining regulatory oligonucleotides that function in the context of a chromosome. Thus, a method of the invention can be practiced such that integration of the expression vector into the eukaryotic host cell chromosome occurs, forming a stable construct prior to selection for an expressed reporter molecule. Such a system provides a means to identify a regulatory element that effects its activity due, for example, to a conformational change in a chromosome such as a nucleosome unwinding or DNA bending event.

A construct comprising a regulatory cassette operatively linked to a reporter cassette, which can be contained in a vector, can be integrated into a chromosome by a variety of methods and under a variety of conditions. Thus, the present invention should not be construed as limited to the exemplified methods, for example, the use of an integrating retroviral vector. Shotgun transfection, for example, can result in stable integration if selection pressure is maintained upon the transfected cell through several generations of cell division, during which time the transfected nucleic acid construct becomes stably integrated into the cell genome. Directional vectors, which can integrate into a host cell chromosome and form a stable integrant, also can be used. These vectors can be based on targeted homologous recombination, which restricts the site of integration to regions of the chromosome having the homology, and can be based on viral vectors, which can randomly associate with the chromosome and form a stable integrant, or can utilize site specific recombination methods and reagents such as a lox-Cre system and the like.

Shotgun transfections can be accomplished by a variety of well known methods, including, for example, electroporation, calcium phosphate mediated transfection, DEAE dextran mediated transfection, a biolistic method, a lipofectin method, and the like. For random shotgun transfections, the culture conditions are maintained for several generations of cell division to ensure that a stable integration has resulted and, generally, a selective pressure also is applied. A viral vector based integration method also can be used and provides the advantage that the method is more rapid and establishes a stable integration by the first generation of cell division. A viral vector based integration also provides the advantage that the transfection (infection) can be performed at a low vectorxell ratio, which increases the probability of single copy transfection of the cell. A single copy expression vector in the cell during selection increases the reliability that an observed regulatory activity is due to a particular oligonucleotide, and facilitates isolation of such an oligonucleotides.

A type C retrovirus viral vector is particularly useful for practicing a method of the invention. There are a variety of retroviral systems for infecting cells with genes. The production of recombinant retrovirus particles suitable for the introducing the expression vectors described herein are well known, and exemplary methods are described by Pear et al., *Proc. Natl. Acad. Sci., USA.* 90:8392-8396, 1993; Owens et al., *Cancer Res.,* 58:2020-2028, 1998; and Gerstmayer et al., *J. Virol. Meth.,* 81:71-75, 1999, each of which is incorporated herein by reference. Additional viral vectors suitable for use in the present invention include the lentivirus vector described by Chang et al., *Gene Ther.,* 6:715-728 (1999); the spleen necrosis virus-derived vector described by Jiang et al., *J. Virol.,* 72:10148-10156 (1998); and adenovirus-based vectors such as is described by Wang et al., *Proc. Natl. Acad. Sci. USA,* 93:3932-3926 (1996).

The invention also provides an isolated synthetic regulatory oligonucleotide having transcriptional or translational regulatory activity. Such an oligonucleotide can be used in a variety of gene expression configurations for regulating control of expression. A synthetic transcriptional regulatory oligonucleotide, which can be obtained by a method of the invention, can increase (enhance) or decrease (silence) the level of expression of a recombinant expression construct when operatively linked to a regulatory cassette comprising a minimal or other promoter element. Preferably, the regulatory oligonucleotide selectively regulates expression in a context specific manner, including, for example, in a cell or tissue specific manner, or with respect to a particular promoter or other effector sequences associated with a promoter.

A synthetic translational regulatory oligonucleotide, which can be obtained using a method of the invention, can increase or decrease the level of translation of an mRNA containing the oligonucleotide, and can have IRES activity, thereby allowing cap-independent translation of the mRNA. In particular, a translational regulatory oligonucleotide can selectively regulate translation in a context specific manner, depending, for example, on the cell type for expression, the nature of the IRES sequence, or the presence of other effector sequences in the expression construct.

Accordingly, the present invention provides an isolated synthetic transcriptional or translational regulatory oligonucleotide, which can be identified using the methods disclosed herein. As used herein, the term "isolated," when used in reference to a regulatory oligonucleotide, indicates that the nucleotide sequence is in a form other than the form in which it is found in nature. Thus, an isolated regulatory oligonucleotide is separated, for example, from a gene in which it normally can be found in nature, and particularly from a chromosome in a cell. It should be recognized, however, that the regulatory oligonucleotide can comprise additional nucleotide or other sequences, yet still be considered "isolated" provided the construct comprising the regulatory oligonucleotide is not in a form that is found in nature. Thus, the oligonucleotide can be contained within a cloning vector or and expression vector, or can be operatively linked to a second nucleotide sequence, for example, another regulatory element or an expressible polynucleotide.

A regulatory oligonucleotide as disclosed herein also is referred to generally as a synthetic regulatory oligonucleotide, for example, a synthetic IRES. As used herein, the term "synthetic" indicates that oligonucleotides that can be screened using the disclosed methods can be produced using routine chemical or biochemical methods of nucleic acid synthesis. It should be recognized, however, that screening of synthetic randomized oligonucleotide libraries can identify regulatory elements that correspond to portions of nucleotide sequences found in genes in nature. Nevertheless, such oligonucleotides generally are present in an isolated form and, therefore, cannot be construed to be products of nature. As disclosed herein, the methods of the invention can identify previously known regulatory element, including, for example, binding sites for the transcription factors SP1, API, NF-κB, CREB, zeste and glucocorticoid receptor (see Tables 1 and 2). It should be recognized that such previously known regulatory elements are not considered to be within the scope of compositions encompassed within the present invention.

The term "oligonucleotide", "polynucleotide" or "nucleotide sequence" is used broadly herein to mean a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence or polyribonucleic acid sequence, or the like, and can be single stranded or double stranded, as well as a DNA/RNA hybrid. Furthermore, the terms "oligonucleotide", "polynucleotide" and "nucleotide sequence" include naturally occurring nucleic acid molecules, which can be isolated from a cell, as well as synthetic molecules, which can be prepared, for example, by methods of chemical synthesis or by enzymatic methods such as by the polymerase chain reaction (PCR).

Synthetic methods for preparing a nucleotide sequence include, for example, the phosphotriester and phosphodiester methods (see Narang et al., *Meth. Enzymol.* 68:90, (1979); U.S. Pat. No. 4,356,270, U.S. Pat. No. 4,458,066, U.S. Pat. No. 4,416,988, U.S. Pat. No. 4,293,652; and Brown et al., *Meth. Enzymol.* 68:109, (1979), each of which is incorporated herein by reference). In various embodiments, an oligonucleotide of the invention or a polynucleotide useful in a method of the invention can contain nucleoside or nucleotide analogs, or a backbone bond other than a phosphodiester bond.

For convenience of discussion, the term "oligonucleotide" generally is used to refer to a nucleotide sequence that is being examined for transcriptional or translational regulatory activity, whereas the term "polynucleotide" or "nucleotide sequence" generally refers to a sequence that encodes a peptide or polypeptide, acts as or encodes a desired regulatory element, provides a spacer sequence or cloning site, or the like. It should be recognized, however, that such a use only is for convenience and is not intended to suggest any particular length or other physical, chemical, or biological characteristic of the nucleic acid molecule.

The nucleotides comprising an oligonucleotide (polynucleotide) generally are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234 (1994); Jellinek et al., *Biochemistry* 34:11363-11372 (1995); Pagratis et al., *Nature Biotechnol.* 15:68-73 (1997), each of which is incorporated herein by reference).

The covalent bond linking the nucleotides of an oligonucleotide or polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tarn et al., *Nucl. Acids Res.* 22:977-986 (1994); Ecker and Crooke, *BioTechnology* 13:351360 (1995), each of which is incorporated herein by reference). The incorporation of non-naturally occurring nucleotide analogs or bonds linking the nucleotides or analogs can be particularly useful where the nucleotide sequence is to be exposed to an environment that can contain a nucleolytic activity, including, for example, a tissue culture medium or upon administration to a living subject, since the modified nucleotide sequences can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

The present invention also provides an expression vector, which is useful for identifying a transcriptional or translational regulatory oligonucleotide according to the present invention. A vector useful for identifying a transcriptional regulatory oligonucleotide generally contains a reporter cassette, which includes a nucleotide sequence encoding at least one reporter molecule, and a regulatory cassette, which is operatively linked to the reporter cassette and comprises a minimal promoter element. The construct comprising the regulatory and reporter cassettes also generally contains a site for introducing an oligonucleotide to be examined for transcriptional or translational regulatory activity into the construct in an operatively linked manner. The reporter cassette generally does not contain a promoter for regulating transcription of the reporter gene, and the regulatory cassette generally is operatively linked to the reporter cassette such that expression of the reporter gene is regulated by the regulatory cassette. As such, various regulatory cassettes and reporter cassettes conveniently can be substituted into the vector, as desired. In one embodiment, the reporter cassette comprises a dicistronic construct, which includes first and second cistrons, which encode two different reporter molecules. Preferably, the nucleotide sequences encoding the first and second reporter molecules are operatively linked by a spacer nucleotide sequence that contains an IRES, or contains a site that facilitates insertion of an oligonucleotide to be examined for IRES activity in an operatively linked manner.

A vector useful for identifying an oligonucleotide having IRES activity generally contains a dicistronic reporter cassette, which includes first and second nucleotide sequences that encode respective first and second reporter proteins, and a regulatory cassette operatively linked to the dicistronic reporter cassette. The dicistronic reporter cassette further contains an intervening (intercistronic) spacer nucleotide sequence between the first and second encoding nucleotide sequences; the spacer nucleotide sequence generally contains a sequence that facilitates insertion of an oligonucleotide to be examined for IRES activity, for example, a cloning site, generally a multiple cloning site comprising one or more unique restriction enzyme recognition sites or a recombinase recognition site to facilitate insertion of the oligonucleotide sequence. Such a vector is useful for identifying an IRES by detecting a change in the level of expression of the second reporter. As disclosed herein, an IRES also can have translational enhancing activity or translation inhibitory activity, which can be conveniently detected using a monocistronic reporter cassette and detecting an increased or decreased level of translation, respectively, due to the oligonucleotide comprising the IRES.

In one embodiment, the expression vector is an integrating expression vector, which comprises nucleotide sequences that provide a means for stable integration of the regulatory and reporter cassettes into a chromosome of a eukaryotic host cell. Sequence elements that facilitate stable integration are disclosed herein or otherwise known in the art. Stable integration is conveniently effected using a retroviral based expression vector having the elements to facilitate packaging into an infectious retroviral particle and the elements to facilitate stable integration. These components can vary widely but, generally, the packaging elements comprise a truncated gag gene comprising sequences required for retrovirus packaging located within the expression vector nucleotide sequence, and the integration elements which comprise and upstream long terminal repeat (LTR) and downstream LTR elements positioned at the respective upstream and downstream flank of the packaging element and the regulatory/reporter cassette elements. The upstream LTR preferably comprises an immediate early gene promoter, an R region, and a U5 region, as are well known in the retroviral and expression vector arts.

An integrating expression vector useful for identifying a transcriptional regulatory oligonucleotide generally contains an immediate early gene promoter that is derived from Rous sarcoma virus or cytomegalovirus, and the downstream LTR generally comprises a consensus transcription initiator sequence. Integrating expression vectors such as MESVR/EGFP*/IRESpacPro(ori) (SEQ ID NO: 1) and MESVR/EGFP*/IRESNCAMPro(ori) (SEQ ID NO: 9) as disclosed herein provide examples of integrating expression vectors useful for identifying a transcriptional regulatory oligonucleotide. However, as will be readily apparent, the various cassettes in the exemplified vectors can be substituted with other cassettes encoding, for example, reporter molecules having a desired characteristic, or comprising a desired promoter, enhancer, silencer or other regulatory element; or can be modified to contain a desirable cloning site, for example, by substituting a restriction endonuclease recognition site or multiple cloning site with a recombinase recognition site.

An integrating expression vector useful for identifying an oligonucleotide having IRES activity also generally contains an immediate early gene promoter that is derived from Rous sarcoma virus or cytomegalovirus, and the downstream LTR generally comprises a consensus transcription initiator sequence. An integrating expression vector such as MESVR/EGFP/ECFP/RSVPro (SEQ ID NO: 109) provides an example of an integrating expression vector useful for identifying an oligonucleotide having IRES activity. As above, however, various modifications and substitutions to the exemplified vector readily can be made using routine methods and commercially available reagents.

The present invention also provides a recombinant nucleic acid molecule comprising a transcriptional or translational regulatory element of the invention linked to a second heterologous polynucleotide. The term "second" is used herein in reference to a nucleotide sequence only to distinguish it from the nucleotide sequence comprising the regulatory oligonucleotide. The term "heterologous" is used herein in a relative sense to indicate that the second nucleotide sequence is not normally associated with the oligonucleotide comprising regulatory element in nature (where the synthetic regulatory element corresponds to a regulatory element that exists in nature) or, if it is associated with the regulatory element in nature, is linked to the regulatory element such that the recombinant nucleic acid molecule is different from the corresponding sequence that exists in nature.

The second heterologous polynucleotide can be an expressible polynucleotide, which can encode an RNA of interest such as an antisense RNA molecule or a ribosome, or can encode a polypeptide of interest, for example, a polypeptide to be expressed pursuant to a gene therapy procedure. Where the heterologous polynucleotide is an expressible polynucleotide, it generally is operatively linked to the synthetic regulatory oligonucleotide such that the oligonucleotide can effect its regulatory activity. The second heterologous polynucleotide also can comprise or encode one or more additional regulatory element, which can be known promoter, enhancer, silencer or translational regulatory elements, including such elements that have been identified according to a method of the invention. A recombinant nucleic acid molecule comprising such a combination of regulatory elements can be useful for selectively expressing an RNA or polypeptide in a cell, which can be only one or a few different types of cell or any cell, and can be constitutively or inducibly expressed at a desired level.

The second heterologous polynucleotide also can be a vector, which can be a plasmid vector, viral vector or the like. Accordingly, the present invention also provides a vector comprising a regulatory oligonucleotide of the invention. Insofar as a regulatory oligonucleotide of the invention can be utilized in a variety of configurations for regulating gene expression or protein translation, the general structure of a vector of the invention requires only that it contain a regulatory oligonucleotide as disclosed herein. However, the vector also can contain nucleotides sequences that facilitate the introduction of an expressible polynucleotide or other nucleotide sequence into the vector, particularly such that it is operatively linked to the regulatory oligonucleotide. The vector also can contain other elements commonly contained in a vector, for example, an bacterial origin or replication, an antibiotic resistance gene for selection in bacteria, or corresponding elements for growing and selecting the vector in a eukaryotic cell.

The synthetic regulatory element in a vector can be designed such that it can readily be removed from the vector, for example, by treatment with a restriction endonuclease. Such a characteristic provides a means for developing a system comprising a vector and a plurality of synthetic regulatory oligonucleotides of the invention, any of which alone or in combination can be inserted into the vector. Accordingly, the present invention also provides a system, which can be in kit form, that provides one or more regulatory oligonucleotide sequences of the invention.

A kit of the invention can contain a packaging material, for example, a container having a regulatory oligonucleotide according to the invention and a label that indicates uses of the oligonucleotide for regulating transcription or translation of a polynucleotide in an expression vector or other expression construct. In one embodiment, the system, preferably in kit form, provides an integrating expression vector for use in selecting a regulatory oligonucleotide using a method as disclosed herein. Such a kit can contain a packaging material, which comprises a container having an integrating expression vector and a label that indicates uses of the vector for selecting oligonucleotide sequences capable of regulatory function.

Instructions for use of the packaged components also can be included in a kit of the invention. Such instructions for use generally include a tangible expression describing the components, for example, a regulatory oligonucleotide, including its concentration and sequence characteristics, and can include a method parameter such as the manner by which the reagent can by utilized for its intended purpose. The reagents, including the oligonucleotide, which can be contained in a vector or operably linked to an expressible polynucleotide, can be provided in solution, as a liquid dispersion, or as a substantially dry power, for example, in a lyophilized form. The packaging materials can be any materials customarily utilized in kits or systems, for example, materials that facilitate manipulation of the regulatory oligonucleotides and, if present, of the vector, which can be an expression vector. The package can be any type of package, including a solid matrix or material such as glass, plastic (e.g., polyethylene, polypropylene and polycarbonate), paper, foil, or the like, which can hold within fixed limits a reagent such as a regulatory oligonucleotide or vector. Thus, for example, a package can be a bottle, vial, plastic and plastic-foil laminated envelope, or the like container used to contain a contemplated reagent. The package also can comprise one or more containers for holding different components of the kit.

The following examples are intended to illustrate but not limit the invention.

EXAMPLE 1

Selection of Synthetic Transcriptional Regulatory Elements

This example describes the preparation of a vector useful for selecting transcriptional regulatory elements and the identification and characterization of synthetic transcriptional regulatory elements.

A promoter element proviral vector library was constructed using the retroviral-mediated EGFP/FACS selection strategy for synthetic promoter elements according to the disclosed methods. A library of promoter elements (random 18 mers; Ran18) was constructed in the proviral selection vector, which was packaged into retroviral particles in COS1 cells. The retroviral particles were harvested and used to infect target cells, which were then treated for 3 days with puromycin to kill uninfected or poorly expressing cells. The surviving cells were subjected to FACS analysis and the most highly fluorescent cells collected. Genomic DNA was prepared from these cells and the regulatory oligonucleotides were recovered by PCR and direct sequencing. The elements then were religated into the proviral vector for a second round of selection. Finally the elements were ligated into the pLuc luciferase reporter vector and the activities of the elements was quantitated by luciferase assay.

Such a method involves the generation of several million enhancer/promoter cassettes, and testing their transcriptional activity in mammalian cell culture. A library of element cassettes was ligated immediately upstream of a minimal promoter unit that contains a TATA box and an initiator sequence in a selection vector (see below; see, also, FIG. 1). In order to deliver the promoter element library into cells as efficiently as possible, a selection vector was designed based on a retrovirus. The use of a retroviral delivery system has three advantages over a plasmid based system: 1) the introduction of the constructs into cells by retroviral infection is extremely efficient; 2) on average each cell receives only one promoter construct; and 3) the introduced construct is stably integrated into the cellular genome.

Production of retroviruses from a proviral vector (packaging) was achieved by transfecting the proviral vector into cells together with helper plasmids that encode the packaging functions. In the present method, the promoter element library that was constructed in a proviral vector was packaged into retroviruses by transfection into COS1 cells. These viruses were then used to infect the target cells. Each synthetic promoter element cassette in the proviral promoter element library was linked to a reporter cassette that reports on its activity after integration into the genome of the target cell. The reporter cassette contained nucleotide sequences encoding enhanced green fluorescent protein (EGFP) and puromycinN-acetyltransferase (pac), arranged in a dicistronic construct that allows two separate gene products to be expressed from a single mRNA that is driven by a single promoter. This arrangement enabled selection of synthetic promoters using fluorescent activated cell sorting (FACS) and resistance to puromycin.

After infection of cells with the retroviral promoter element library and integration into the genome, each promoter was scored for its transcriptional activity by examining the activity of the reporter gene EGFP. Using the retroviral delivery system, each cell generally received only one promoter cassette. After 2 to 3 days of infection by the retroviruses, uninfected cells were removed by treatment them with puromycin, then the surviving cells were subjected to FACS analysis and cells having the most active promoters were selected. The level of EGFP expression in each cell reflects the strength of an individual synthetic promoter element cassette, such that highly fluorescent cells are likely to contain highly active promoter elements.

After multiple rounds of selection using the EGFP/FACS analysis, the promoters were amplified from the cellular genome using the polymerase chain reaction (PCR) and subjected to automated DNA sequencing to determine the identity of each of the synthetic promoter elements. The activity of the regulatory cassette was confirmed using a luciferase reporter system that is more amenable to quantitation of promoter activity levels. To perform this quantitation of promoter activity, each synthetic promoter/luciferase plasmid was independently transfected into the cell line in which the initial selection was performed (e.g. Neuro2A neuroblastoma cells) and luciferase activity was measured using standard methods.

A. Synthetic Promoter Methodology

A library of synthetic DNA sequences to be tested for transcriptional regulatory activity was generated and screened as described below. The pool (library) of promoter elements containing random sequences or combinations of known motifs was ligated into a proviral selection vector generating a proviral promoter element library.

Any of at least three different types of libraries of oligonucleotides can be prepared and examined according to the disclosed methods. One type of library consists of random sequences of a given length, for example, 18-mers, which are tested for their ability to enhance the activity of a minimal promoter such as a TATA motif and a site for the initiation of transcription. Such a library, which was examined as disclosed herein, has the potential to identify novel cis regulatory elements and transcription factors that bind to these elements.

A second type of library combines a random oligonucleotide sequence and a known regulatory motif, for example, a TPA responsive element (TRE; API binding site). By varying the nature, polarity, number, order and spacing of known regulatory elements and random oligonucleotide sequences, such a library also can be used to identify novel cis regulatory elements and transcription factors that bind to these elements (as above), and further can identify novel promoter elements that modulate the function of known regulatory elements.

A third type of library combines transcription factor binding sites already known to function in particular contexts of eukaryotic gene regulation, for example, the binding sites for Krox, paired domain (Pax) and AP-1 (TRE), which are present in naturally occurring neuronally-expressed genes. Such a library can be used to establish rules and constraints that govern functional interactions between elements and their associated transcription factors. Construction of the library involves linking several elements together such that the order, number, and spacing of the elements are controlled, for example, the successive element ligation procedure as disclosed herein (see Example 1F).

A key feature of the synthetic transcriptional regulatory element methodology of the invention is the strategy for the selection of functional promoter elements. A screening procedure strategy was devised that allows testing of random elements or combinations of elements for transcriptional modulating activity in mammalian cells. Several key requirements necessary for successful selection of synthetic transcriptional regulatory elements in mammalian cells are 1) each cell should receive a single unique cassette to avoid selection of inactive elements that happen to be present in the same cell as an active element; 2) the synthetic elements should be shielded from the effects of genomic sequences that may activate or repress transcription; 3) the delivery system should be efficient so that a complex library can be readily screened; and 4) the selection process should be stringent and should be based on a reporter gene assay that is highly sensitive and that faithfully reports the activity of the promoter elements.

A library of single stranded oligonucleotides containing eighteen randomized positions (A, C, G or T at each position) was synthesized on an Applied Biosystems DNA synthesizer. This portion of the oligonucleotide was designated Ran18. Flanking the Ran18 cassette were short regions of defined sequence, including recognition sequences for the restriction enzyme Mlu I, which allowed the cassette to be inserted into the MESV/IRES/EGFP/pacPro(ori) proviral vector (SEQ ID NO: 1; see, also, FIG. 1).

To prepare the double stranded Ran18 oligonucleotides, an additional primer that was complementary to the right flanking portion of the single stranded oligonucleotide was synthesized and annealed to the Ran18 oligonucleotide. Annealing was performed with equimolar amounts of the flanking primer and the Ran18 oligonucleotide in a solution containing Tris-HCl (pH 7.5) and 1 mm $MgCl_2$ at 100° C. for 5 minutes, followed by slow cooling to room temperature. The second strand was generated by primer extension using the Klenow fragment of DNA polymerase I and 50 mM of dNTPs at 30° C. The double stranded oligonucleotide was purified and digested with Mlu I at 37° C. for 12 hr, and was purified by extraction from an 8% polyacrylamide gel.

After digestion, the library of Ran18 cassettes was ligated into the proviral vector at a 1:1 molar ratio of oligonucleotide to vector. Typically 0.5 to 2 μg of vector was used in each ligation in a volume of 100 ml. DNA was purified using QiaQuick PCR purification columns (Qiagen) and the ligation mixture was used to transform frozen electrocompetent XL 1-Blue E. coli cells (Stratagene) by electroporation. The transformation mix was plated onto 150 mm LB plate containing Ampicillin. Smaller aliquots of the transformation mix were plated onto 100 mm plates and colonies were counted to determine the number of transformants per microgram of vector. Plasmid DNA from the library was prepared via standard procedures (Qiagen Maxi-plasmid Prep) and the DNA was transfected into eukaryotic cells for retroviral packaging.

B. Retroviral Vector Construction

Retroviruses are extremely useful tools to deliver genes into eukaryotic cells both in culture and in whole animals. Currently, however, most retroviral vectors are not tailored for tissue specific or developmental stage specific delivery of genes. Thus, a benefit of screening a retroviral library for functional synthetic regulatory elements as disclosed herein is the potential to create novel retroviruses with exquisite target specificity. Such vectors can be extremely useful for generating cell lines or transgenic animals for diagnostic screening procedures and drug development. In addition, such vectors can be useful for gene therapy in humans.

A retrovirus is a single stranded RNA virus that infects a cell and integrates into the genome of a cell by copying itself into a double stranded DNA molecule by reverse transcription. The integrated retrovirus genome is referred to as a provirus. Retroviruses have a two stage life cycle, existing both an RNA and DNA form. The RNA form of the virus is packaged into an infectious particle that is coated with a glycoprotein that is recognized by receptors on the host cell. This interaction promotes a receptor mediated internalization event, resulting in exceptionally efficient delivery of the viral genome into the cell. After transport to the cell nucleus and uncoating, the RNA genome is reverse transcribed into a DNA form (a provirus). During the reverse transcription process, the provirus integrates into the host cell genome. Retroviruses do not integrate in a completely random fashion, but instead have a distinct preference for integration into regions of the genome that are transcriptionally competent. This characteristic reduces the likelihood that the provirus will be silenced by integration into a transcriptionally repressive domain.

In a recombinant retrovirus, the entire coding region of the virus is removed and replaced with a transgene. This replacement is done by standard molecular biological techniques using a proviral version of the virus that is propagated as a bacterial plasmid (a pro-retroviral vector). However, other sequences in the retrovirus genome are required for the functions of viral transcription and packaging: these genes encode the viral gag and pol proteins, and the viral glycoprotein coat. While such sequences can be removed from the pro-retroviral plasmid, in order to obtain a fully functional recombinant virus, they must be provided in trans, for example, on other plasmids that are introduced into the host cell via cellular transfection. Alternatively, these helper functions can be designed to already be integrated into the cellular genome of the viral packaging line.

Retroviruses have two viral promoters called long terminal repeats (LTRs), one located at each end of the viral genome. The upstream LTR is responsible for promoting transcription of the DNA provirus into the RNA form. The downstream LTR is not used for transcription during the RNA phase of the life cycle. However, during reverse transcription of the RNA into the DNA provirus, the downstream LTR provides a template for the replication of the upstream LTR. Thus, native retroviruses contain identical sequences in their upstream and downstream LTRs.

Nucleotide sequences that encode enhanced green fluorescent protein (EGFP) and puromycin N-acetyltransferase (pac) were inserted into a retroviral vector (see below). The two reporter genes are expressed as a single transcript, and are linked by an internal ribosome entry sequence (IRES). Expression of both reporter genes is controlled by the same promoter. The upstream LTR was modified to contain a strong promoter from the Rous sarcoma virus (RSV), thus ensuring efficient transcription of the RNA viral genome and a high viral titer. The downstream LTR was modified to contain a minimal synthetic promoter and a multiple cloning site for insertion of the Ran18 elements. The downstream LTR is not used for transcription during the RNA phase of the lifecycle.

However, during reverse transcription of the RNA into the DNA provirus, the downstream LTR provides a template for the replication of the upstream LTR. From this position, the Ran18/minimal promoter cassette can drive expression of the reporter genes in the integrated form of the virus.

The MESVR/EGFP*/IRESpacPro(ori) (SEQ ID NO: 1) was based on MESV/IRESneo (Owens et al., supra, 1998), which, in turn, was based on the Murine Embryonic Stem cell Virus (MESV) retrovirus (Mooslehner et al., *J. Virol.*, 64:3056-3058, 1990; Rohdewohld et al., *J. Virol.*, 61:336-343, 1987, each of which is incorporated herein by reference). MESV is a C-type retrovirus that was modified to remove sequences that are necessary for independent replication. Consequently, the virus can only replicate with the assistance of helper genes that encode the proteins required for viral genome packaging and insertion into the host genome.

Five different insertions were made to produce the final MESVR/EGFP*/IRESpacPro(ori) vector, which contains 6357 base pairs (SEQ ID NO: 1). First, a cassette containing a polylinker for the insertion of Ran18 elements, the adenovirus major late promoter, and the initiator (Inr) from the mouse terminal deoxynucleotidyl transferase gene and a complete R region were inserted at the downstream U3 region (Lagrange et al., *Genes Devel.* 12:34-44, 1998; Colgan et al., *Proc. Acad. Natl. Sci., USA* 92:1955-1959, 1995, each of which is incorporated herein by reference). Second, the U3 region enhancer elements from RSV were inserted at the upstream LTR. The source of the RSV enhancer elements was the pRc/RSV plasmid (Invitrogen Corp., La Jolla Calif.). Third, mutations to produce a green fluorescent protein (GFP) having enhanced expression (EGFP) were introduced (Zernicka-Goetz et al., *Development* 124:1133-1137, 1997, which is incorporated herein by reference). Fourth, a copy of the puromycin N-acetyltransferase (pac) was inserted downstream of the IRES after excising the neomycin resistance gene. The source of the pac gene was the pPUR plasmid (Clontech, Palo Alto Calif.). Fifth, an SV40 origin of replication was inserted into the plasmid. The source of the SV40 origin was the plasmid pcDNA3.1 (Invitrogen Corp.). Many of the fragments were generated as PCR products from vectors from commercial sources.

The relevant portion of the retroviral vector MESVR/EGFP*/TRESpacPro(ori) (SEQ ID NO: 1) is shown in FIG. 1. As indicated above, it contains a strong enhancer from RSV in the position of the upstream LTR that drives expression of the RNA viral genome, and contains a minimal synthetic promoter in the position of the downstream LTR (FIG. 1). The multiple cloning site upstream of this minimal promoter permits the insertion of oligonucleotides such as the Ran18 elements to generate a library of proviruses, each containing a unique promoter cassette in the downstream LTR. The proviral vector library was transfected into mammalian cells together with helper plasmids required for viral production including a plasmid that encodes the group antigen (gag) and the integrase enzyme (pol) that is packaged with the RNA genome as well as a plasmid that encodes the glycoprotein coat (VSV-G).

Retroviruses exist as RNA and DNA forms. The DNA form is referred to as the provirus and must be transcribed to generate the RNA form that is packaged into an infectious viral particle. The viral particle is coated with a glycoprotein that is recognized by receptors on the host cell leading to receptor-mediated internalization. After entry into the cell nucleus, the RNA genome is reverse transcribed into the DNA form which is stably integrated into the host cell genome.

The viral packaging protocol involved a triple transfection into Cos-1 cells of a library containing pro-retroviral vectors that harbor the putative promoter elements together with the two separate plasmids that encode the gag/pol and VSV-G proteins, respectively. Cellular transcription machinery is used to generate the viral RNA strands that are packaged into viral particles and subsequently bud from the cell membrane. These viral particles can infect a naive cell as described above. After reverse transcription and integration, the strong promoter located in the upstream LTR is lost and is replaced by the Ran18/minimal promoter cassette from the downstream LTR. Thus, the viral library is fully representative of the original vector library because all viral RNAs were transcribed from the same strong promoter. In contrast, each integrated DNA version of the virus contains a different Ran18 cassette in the upstream LTR, which now drives expression of the selectable markers, EGFP and pac, selection for which indicates the strength of activity of the promoter cassette.

Packaging of the pro viral vector library was achieved by cotransfection of the proviral DNA into COS1 cells together with the packaging genes, which are contained on two separate helper plasmids, pCMV-GP(sal) and pMD.G. The pCMV-GP(sal) plasmid has a cytomegalovirus promoter (PCMV) driving the genes that encode the group antigen (gag) and reverse transcriptase enzyme (pol) from the Moloney murine leukemia virus (MMLV). The pMD.G plasmid encodes the vesicular stomatitis virus G glycoprotein (Naldini et al., *Science* 272(5259):263-267, 1996, which is incorporated herein by reference). These two plasmids were cotransfected into COS1 cells along with the library of recombinant retroviral vectors containing putative promoter elements in order to generate a library of retroviruses.

COS1 cells were seeded into 100 mm dishes at $8 \times 10^5$ cells/dish and transfected 24 hr later with 4 jig of proviral library DNA and 4 μg of the pCMV/gag-pol and pCMV/VSV-G plasmids using Fugene transfection reagent (Roche). The cellular transcription machinery generates viral RNA strands that are packaged into viral particles and subsequently bud from the cell membrane into the culture medium. The medium was collected, diluted with an equal volume of media, filtered to remove cellular debris, and combined with polybrene to a final concentration of 2.5 mg/ml of viral supernatant. This mixture was used to infect Neuro2A cells in monolayer culture. The ratio of viral particles to cells was optimized so as to ensure a high probability of single infection/integration events, and generally resulted in infection of 25-40% of the Neuro2A cells.

C. Characterization of the Selection Method

In order to demonstrate the feasibility and efficacy of the retroviral delivery and FACS selection of synthetic regulatory elements, an initial set of experiments was performed in which proviral plasmids were prepared containing the minimal promoter, Pmin, alone; a minimal promoter containing three copies of the TRE/AP-1 element (3×TRE); or a full strength RSV promoter. The latter two regulatory elements were expected to drive expression of the EGFP gene at a high level, whereas the minimal promoter represents the baseline activity.

Actively infecting retroviruses were prepared for each of these three promoter constructs by carrying out a triple transfection of a monolayer of actively dividing COS-1 cells with two helper plasmids encoding genes that are essential for the propagation of active virus. The culture media containing fully active viral particles corresponding to each of the three promoters was collected and used to infect the target neuroblastoma cell line, Neuro2A. These cells were selected for this study because they grow quickly, are relatively nonadherent, have a high transfection efficiency, and are efficiently infected using the retroviral vector.

To establish the maximal and minimal values of promoter activity obtainable using this EGFP/FACS selection procedure, several control experiments were performed using the very strong (RSV), moderately strong (3×TRE), and minimal (Pmin) promoters. These experiments were performed in order to determine the optimal gating of cells so that only highly active Ran18 elements would be assayed. Neuro2A cells infected with the retrovirus in which the EGFP reporter was driven by the strong RSV promoter showed a high level of EGFP fluorescence, and the cells infected with the 3×TRE retrovirus showed an intermediate level of fluorescence. For each of the RSV and TRE-containing retroviruses, the number of highly fluorescent cells was considered to be equivalent to the number of infected cells. Thus, approximately 30% of the cells were infected by the retroviruses. In addition to the positive controls, a second negative control population of cells was infected with a retrovirus containing only the minimal promoter (TATA box). The Pmin-containing retrovirus showed only background levels of autofluorescence, thus providing a baseline for the level of EGFP expression that is produced by the minimal promoter in the absence of an enhancer. These results demonstrate that Neuro2A cells can be efficiently infected with the promoter-containing retroviruses and that the EGFP fluorescence is sufficiently strong in order to select active promoters from inactive or weak promoters.

D. Selection of Synthetic Transcriptional Regulatory Elements

A library of synthetic oligonucleotides, each containing a random sequence of eighteen base pairs (Ran18) to be examined for transcriptional regulatory activity was ligated into the Mlu I restriction site immediately upstream of the minimal promoter in the pro viral selection vector, generating a library of greater than $5 \times 10^7$ individual members. This Ran18 promoter element library was packaged into retroviral particles, which were used to infect the neuroblastoma cell line Neuro2A. After 24 hours, 1 mg/ml puromycin was added to the infected cells, and treatment with puromycin was continued for 3 days to kill uninfected cells. Surviving cells were sorted using a FACSTAR fluorescence activated cell sorter (Becton Dickinson). Control cells were infected with a reporter retrovirus containing either the minimal promoter (Pmin) or a strong promoter (RSV) to drive expression of the EGFP reporter gene. The Pmin control provides a baseline for the level of EGFP expression that is produced by the minimal promoter in the absence of an enhancer. The RSV control provides a measure of infection efficiency.

The fluorescence profile of cells infected with the Ran18 library was compared with that of the Pmin promoter control to determine the fluorescence threshold for promoter element selection. Approximately 1% of the cells showed greater fluorescence than that observed for the minimal promoter alone. Given a viral infectivity of about 33% based on expression for the RSV promoter, about 3% of the elements in the Ran18 promoter element library enhanced the activity of the minimal promoter.

The most highly fluorescent cells were collected and genomic DNA was extracted using the QiaAmp Tissue Kit (Qiagen). The Ran18 cassettes were recovered from the genomic DNA by PCR amplification using primers that flank the Ran18 promoter cassette. The amplified promoters were digested with Nsi I and Bgl II to liberate the Ran18 element cassettes, which then were religated into the proviral selection vector to produce a second generation library, and the EGFP/FACS selection procedure was repeated.

Following the second round of EGFP/FACS mediated selection, Ran18 promoter element cassettes were again recovered by genomic PCR. The amplified promoter cassettes were digested with Nsi I and Eco RI to generate a fragment that includes the Ran18 cassette and the minimal promoter, and the liberated fragments were ligated into a promoter-less luciferase reporter vector (pLuc) to generate Ran18/promoter/pLuc plasmids. The pLuc plasmid was made by introducing a polylinker containing restriction endonuclease sites for Nsi I, Stu I and Eco RI into the Kpn I/Hind III site of the luciferase reporter plasmid PGL3basic (Promega). Following bacterial transformation, individual subclones were isolated, 300 ng was subjected to automated DNA sequencing using an automated DNA sequencer (Perkin-Elmer Applied Biosystems 373 sequencer) to determine the identity of each functional Ran18 promoter element, then the sequences were compared to databases of known regulatory motifs (Transfac and TFD databases).

Two salient features were noted in the sequences of the Ran18 elements selected after two rounds of EGFP/FACS selection. First, as a result of the non-directional cloning strategy, most of the elements contained multiple copies (generally two) of the Ran18 sequences. Comparison of the selected elements with a set of Ran18 elements that were ligated into the same Mlu I restriction site in the proviral vector, but not subjected to EGFP/FACS based selection, indicated that the proportion of multimerized elements was significantly increased in the selected set (70% in the selected set compared to 24% in the unselected set). Second, a large number of the selected Ran18 sequences contained binding sites for known transcription factors, including c-Ets-2, glucocorticoid receptor (GR), E2F-1, Sp1, API, kY factor, CP1, TFIID, PTF-1β, DTF-1, AP2, PEA3, TBP, NF-1, UCRF-L, F-ACT1, CTF, ETF, GATA-1, c-Myc, E2F-1, C/EBPα, 1k2, GATA, and ΔEF1. However, several of the selected Ran18 elements contained no known binding motifs and appear to be novel transcriptional regulatory sequences (SEQ ID NOS: 10, 11 and 13 to 15).

The transcriptional activity of individual Ran18 promoter elements was quantified by luciferase assays after transient transfection of the Ran18/pLuc subclones into Neuro2A cells. Each Ran18/pLuc reporter vector was co-transfected with the control plasmid CMVβgal, which encodes β-galactosidase, to normalize for transfection efficiency. A pLuc reporter vector containing only the minimal promoter unit was used to provide a baseline for the activity of the minimal promoter. Two hundred Ran18/pLuc subclones containing selected Ran18 elements were analyzed by transient transfection and luciferase assay. Approximately 25% of these plasmids produced luciferase activity that was greater than 4-fold above that produced by the minimal promoter, with the highest level of activity being 17-fold above that of the minimal promoter. In contrast, only about 1% of the elements of a comparable set of unselected Ran18 elements had activity greater than 4-fold above that the minimal promoter.

E. Characterization and Uses of Synthetic Transcriptional Regulatory Elements

The selected transcriptional regulatory elements can be examined in a variety of ways, including 1) the level of transcriptional activity produced by each element can be determined using luciferase assays, 2) novel sequences within the element can be multimerized and used as bait in either yeast one-hybrid screening assay or a southwestern screening procedure to isolate potentially novel transcription factors to which the elements bind, 3) activity of the elements can be compared in different cell types or cellular environments such as in the presence of growth factor treatment to identify elements that function in one context but not the other and, therefore, can be useful as a fingerprint for a particular cell type or cellular state, and 4) functional elements can be recombined to examine the rules and constraints governing functional interactions between cis-acting regulatory sequences. In addition, recombination of the elements can produce new elements that combine the benefits of particular individual elements such as strength or cell-type specificity.

A database was created containing the functional Ran18 elements obtained in the above selection procedure, and elements were categorized into those that contained sequences that bind to known transcription factors and those that contained completely novel sequences. In addition, these functional elements were compared to each other to determine the frequency of particular sequence motifs, which reflects the relative abundance of specific transcription factors present in the cells used in the selection process. This promoter element database can be compared to lists of elements that are selected in different cell lines, or in the same cell population that is treated with a different growth factor or drug (see below), thus extending the disclosed selection process to identify Ran18 elements or other regulatory oligonucleotides that function in different cellular environments, for example, in different cell types or in proliferating versus differentiating cells, to determine differences and similarities in the sets of transcriptional regulatory elements that function during these processes.

Active oligonucleotide regulatory elements such as the exemplified Ran18 elements also can be selected for combinatorial analysis by ligating them together using a method such as the selective element ligation procedure (see Example 1F). Once combinations of functional elements are prepared, the synthetic promoter selection procedure is performed on this combinatorial element library. The identified functional promoter elements then are used in DNA/protein binding studies to characterize the transcriptional regulatory proteins to which these elements bind and to identify novel transcription factors. The southwestern screening procedure (Vinson et al., *Genes Devel.*, 2:801 1988; Singh et al., *Cell*, 52:415-423, 1988) or the yeast one hybrid technique (Wang et al, *Nature*, 364:121-126, 1993; Li et al, *Science*, 262:1870-1874, 1993; Dowell et al., *Science*, 265:1243-1246, 1994) can be used for these studies. In addition, characterization of the binding properties of selected elements can be carried out using an electrophoretic mobility shift assay (EMSA).

The ability of cellular proteins to specifically interact with three selected Ran18 elements, S131 (SEQ ID NO: 16), which contains API, SP1, CP1, ETF and c-Ets-2 binding motifs; S133 (SEQ ID NO: 12), which contain an SP1 binding motif; and S146 (SEQ ID NO: 17), which contains C/EBPα, GR, and PR binding motifs, was examined. The Ran18 elements were radiolabeled and combined with nuclear extracts from the Neuro2A neuroblastoma cells or from 3T3 fibroblasts, then the resulting DNA-protein complexes were examined by EMSA. Both cell type-specific and ubiquitous complexes were observed. The S131 and S133 elements both contained Sp1 binding sites, and an Sp1 competitor oligonucleotide, which corresponds to the sequence of an Sp1 binding site, competed for some or all of the complexes formed with these probes. Similarly, element S146, which contains a glucocorticoid response element, formed one complex that was disrupted by incubation with a specific GR competitor, as well as additional complexes that were not disrupted by the GR competitor. These results demonstrate that the selected Ran18 elements can specifically interact with nuclear proteins, including with nuclear proteins only expressed in Neuro2A cells.

The promoter selection techniques disclosed herein can be readily applied for use in disease diagnostic procedures by identifying regulatory elements that are highly active only in specific cell types or cellular contexts. A library of random promoter elements is screened for transcriptional activity in cell lines derived from several different tissue types or from cells that are subjected to a particular treatment, for example, treatment with a growth and differentiation factor such as the TGF-β family growth factor, bone morphogenic factor-4, with signaling molecules or with antiproliferative agents. Regulatory elements that are highly active in these different contexts are sequenced and used to create a "transcriptional element profile" for the cell type or cellular response.

The synthetic promoters also can be used as markers for disease. Many disease states are characterized by aberrant regulation of transcription, often affecting multiple genes. The synthetic promoter selection strategy is used to rapidly identify promoters that show elevated levels of expression in a specific disease state. These promoters are then linked to a reporter gene such as EGFP and integrated into cultured mammalian cells to create a battery of cell lines that model the aberrant transcriptional regulation associated with the disease. Candidate drug treatments can be tested for the ability to alter the activities of these promoters. In a simple model, a panel of drugs can be screened and a drug can be identified that reduces the activity, for example, of 10 out of 12 synthetic promoters whose activity is correlated with the disease. As such, the drug is identified as likely to be targeting a common factor or pathway involved in the activation of each of these promoters. The reporter constructs also can be integrated into transgenic mice such that the expression of EGFP provides a dynamic reporter system that allows the effectiveness of therapeutic agents to be monitored over the course of treatment.

Synthetic promoters that regulate cell specific expression can be used for cell specific expression of a therapeutic gene product in patients using a retroviral mediated gene therapy procedure. For example, a pro-apoptotic agent such as the Bax gene product can be expressed under the control of a synthetic promoter that was selected based on its ability to function only in glioma cells, but not in normal cells, such that expression of the Bax gene only occurs in the glioma cells and selectively kills the glioma cells.

Thus, by selecting elements in different cellular environments, such as those representing normal and diseased states, a set of synthetic promoters can be identified that are responsive (i.e., have transcriptional competence in a particular cellular context), thereby providing a means to diagnose a disease state. A population of such elements can be used, for example, as an array to fingerprint a particular disease phenotype. For instance, the growth patterns and responsiveness of specific tumor cells to various hormones, cytokines, and synthetic agonists or antagonists of these molecules can be probed by determining the regulatory elements and associated transcriptional proteins that are utilized in particular tumor cells. In addition to the potential utility of the promoter selection procedure for disease diagnostics, the method can be useful for constructing synthetic promoters for tissue specific or cellular state specific delivery of transgenes, for example, for gene therapy in humans, or for developmental and gene replacement studies in animals.

F. Successive Element Ligation Procedure

The successive element ligation procedure provides a method for producing multimers of individual regulatory elements into larger cassettes, thus providing a means to generate combinations of particular regulatory elements that lead to a desired pattern or level of expression of an operatively linked polynucleotide. The procedure generally provides a means to randomly link individual transcriptional or translational regulatory elements into cassettes using successive unidirectional ligation to a DNA adaptor immobilized on a solid support, for example, paramagnetic particles coated with streptavidin.

Individual regulatory elements are designed to contain CTCT and GAGA overhangs (or other selected anti-complementary sequences) on the "top" and "bottom" strands, respectively. An adaptor oligonucleotide, containing a biotin group at its 5' end is annealed to a bottom strand oligonucleotide, which contains the 5' overhang sequence, GAGA. The resulting duplex adaptor contains an Nsi I restriction site, which allows cleavage of the multimerized cassette at the end of the procedure. A biotin tagged adaptor is then attached to streptavidin beads and phosphorylated, thereby enabling the ligation of the first regulatory element to the immobilized adaptor complex; the first element contains a donor 5' overhang sequence, CTCT, that is compatible with the recipient GAGA of the adaptor. After ligation of the first element to the immobilized adaptor, the phosphorylation reaction is repeated and the first element is now ready to accept ligation of a second element. This procedure is reiterated to generate a growing chain of regulatory elements. Once a cassette of a given length is synthesized, a capping adaptor oligonucleotide containing an Mlu I restriction site is ligated, terminating the synthesis of elements. The cassettes produced by this procedure are then amplified by PCR, digested with Nsi I and Bgl II to remove the capping adaptors and biotin, and cloned into the Nsi I and Bgl II sites of the proviral promoter selection vector. The combinatorial proviral promoter library is screened to select effective regulatory element combinations as described above.

For the ligation procedure, streptavidin MagneSphere Paramagnetic Particles (Promega, Madison Wis.) are washed three times with 0.5×SSC, capturing the beads using a magnetic stand each time between washes. The beads are then resuspended in 100 µl of 0.5×SSC and 200 pmol of an adaptor oligonucleotide, which contains a biotin group on the 5' end, is attached to the beads through the streptavidin-biotin interaction. The adaptor also contains an Nsi I restriction enzyme cleavage site to clone the cassette following its synthesis. The bound adaptor then is phosphorylated using 300 pmol of ATP and 100 units of polynucleotide kinase in preparation for ligation with individual elements. Pools of elements in equimolar amounts (3 mM each, 30 mM total) are ligated onto the adaptor using 5 units of T4 DNA ligase. The oligonucleotides encoding these elements all contain compatible overhangs of GAGA on the 5' end and CTCT on the 3' end to facilitate assembly. Between enzymatic manipulations, the beads are washed 3 times with 0.5×SSC and once with the reaction buffer of the next step. This step is reiterated to generate the desired cassette length. Finally, a capping oligonucleotide, which contains a Bgl II site, is ligated onto the assembled element cassette. This oligonucleotide in combination with the adaptor is used to facilitate cassette amplification via PCR. The amplified products are then digested with Nsi I and Bgl II and cloned into the proviral selection vector, and combinations of regulatory elements having desirable characteristics can be selected.

EXAMPLE 2

Validation of Synthetic Regulatory Element Selection Method

This example demonstrates the disclosed synthetic regulatory element selection method can be used routinely to screen libraries of oligonucleotides and can consistently identify synthetic transcriptional regulatory elements.

The retrovirus vector MESVR/EGFP*/IRES/pacPro(ori) (SEQ ID NO: 1; see Example 1B) was used to screen a second library of Ran18 sequences using the synthetic promoter construction method (SPCM). More than 100 DNA sequences that showed increased promoter activity (4 to 50-fold) in the neuroblastoma cell line Neuro2A were identified. The DNA sequences of selected synthetic promoters were determined and database search using the RIGHT software package, which allowed simultaneous comparison of a database of active Ran18 elements to existing databases such as TransFac. The search revealed a predominance of eight motifs—AP2, CEBP, GRE, Ebox, ETS, CREB, API, and SP1/MAZ; about 5 to 10% of the active DNA sequences were not represented in known transcription factor databases and appeared to be novel. The most active of the selected synthetic promoters contained composites of pairs, triples, or quadruples of these motifs. Assays of DNA binding and promoter activity of three exemplary motifs (ETS, CREB, and SP1/MAZ) confirmed the effectiveness of SPCM in identifying functional transcriptional regulatory elements.

Methods and reagents were essentially as described in Example 1. Ran18 oligonucleotides were constructed using a PE Biosystems DNA synthesizer. Ran18 elements were flanked by two different sequences (left—ctactcacgcgtgatcca, SEQ ID NO: 18; and right—cggcgaacgcgtgcaatg, SEQ ID NO: 19) containing the Mlu I restriction site that allowed cloning into the selection vector. Double stranded Ran18 sequences were generated by primer extension, digested with Mlu I, and purified by extraction from an 8% polyacrylamide gel. The library of Ran18 sequences was ligated into the MESVR/EGFP*/IRES/pacPro(ori) (SEQ ID NO: 1) retroviral vector and transformed into XL1-Blue E. coli (Stratagene, San Diego, Calif.). Plasmid DNA was prepared using Maxi-Prep columns (Qiagen, Valencia, Calif.). Packaging was achieved by co-transfection of the proviral DNA library into COS1 cells together with the helper plasmids, pCMV-GP(sal) and pMD.G (see Example 1).

Three 100 mm dishes of COS 1 cells ($8 \times 10^5$ cells/dish) were transfected with 4 µg of proviral library DNA, 4 ug of the pCMV/gag-pol plasmid and 2 µg of the pCMV/VSV-G plasmid using FuGENE 6 transfection reagent (Roche). Media were changed 24 hr later, and supernatant containing retroviral particles was collected after an additional 24 hr, filtered, and combined with polybrene to a final concentration of 2.5 µg/ml. This mixture was used to infect Neuro2A cells in monolayer culture. The ratio of viral particles to cells was optimized to ensure a high probability of single infection/integration events; this ratio generally resulted in infection of 25 to 40% of the Neuro2A cells. After retroviral infection, each cell incorporated on average a single integrated DNA provirus containing a different Ran18 element upstream of the minimal promoter and the selectable markers, EGFP and pac. Identification of active Ran18 promoter elements involved two selection steps (see Example 1).

To quantify the activity of Ran18 elements, the Ran18/pLucPro plasmids were transfected into Neuro2A cells in 24 well tissue culture plates. One hundred nanograms of each reporter was transfected together with CMVβgal to normalize for transfection efficiency and 48 hr later the cells were harvested and assayed for β-galactosidase and luciferase activity (Example 1). The activity of pLucPro was used as a reference standard for measuring the levels of luciferase activity generated by selected Ran18/promoters.

Ran18 elements were sequenced using an automated DNA sequencer (Model 373, PE Biosystems, Foster City, Calif.). Sequences were searched for candidate transcription factor binding motifs present in the TransFac database (release 3.5) using the RIGHT (Reeke's Interactive Gene Hacking Tool) software package. RIGHT is a motif recognition program based on a regular expression search and is particularly useful for SPCM because it allows a batch format for sequence input and has the capacity to simultaneously analyze large numbers of Ran18 promoter sequences. The unselected ("U") Ran18 elements showed a Gaussian distribution with a mean activity of 2-fold and a standard deviation of 0.8. Using this distribution for the activities of the U Ran18 elements and allowing for a confidence interval of 98%, it was determined that 4-fold activity above that of the minimal promoter represented a statistically significant level.

Analysis of the distribution of activities of the 480 selected elements ("S"), superimposed upon the normal distribution from U Ran18 sequences revealed that 120 of the selected (S) Ran18 sequences (approximately 25%) had activity that was 4 to 50-fold greater than that of the minimal promoter. In comparison, only one sequence from the U Ran18 sequence (less than 1% of the total) showed greater than 4-fold activity. Thus, SPCM provided approximately 25-fold enrichment of active promoter elements. A group of S Ran18 sequences that was highly active in luciferase assays also was examined and is referred to at the SLA (selected luciferase activator) Ran18 elements.

The DNA sequences of 106 SLA, 133 S, and 132 U Ran18 elements were determined and compared to known motifs within the TransFac database. Only motifs having 100% sequence identity with TransFac motifs with a length of 6 base pairs or greater were scored as matches. Known regulatory motifs were identified in each of the three sets, but the prevalence and linear arrangement of particular motifs differed among the sets.

Twenty of the most active Ran18 sequences from the SLA set showed 78 matches with known motifs (Table 1; SEQ ID NOS: 20 to 39). A significant number of these matches occurred as composites consisting of two or more motifs that either were overlapping or contiguous. The two most active elements, MS44 (SEQ ID NO: 20) and S173 (SEQ ID NO: 21), registered 6 and 5 matches, respectively, with known motifs and contained a composite made up of ETS, AP1, CREB, and GATA motifs. These results indicate that a composite motif arrangement can contribute significantly to the high level of activity produced by these synthetic promoters.

An analysis of the complete SLA, S, and U sets was performed to compare the number of matches, the distribution of motifs, and the number and type of composite elements. Overall, the SLA and S sets contained approximately twice as many motifs as the U set. A significant proportion of the motifs identified in all three sets (46% for U, 46.5% for S, and 51% for SLA) were made up of only eight motifs, which represented putative binding sites for eight different families of transcriptional regulators—AP2, CEBP, GRE, E-box, ETS, CREB, AP1, and SP1/MAZ. The SLA and S sets also contained approximately twice as many of these motifs as the U set. A comparison of the occurrences of each of the 8 most frequent motifs among the three sets revealed a significant increase in the number of Ebox, ETS, CREB, AP1, and SP1/MAZ motifs in SLA and S sets as compared to the U set, but no significant increase in the number of GRE and CEBP motifs.

The total number of composites increased approximately 2.8-fold in both the SLA and S sets over the number found in the U set. Composites were further categorized into three types: category A, including those containing two or more of the 8 most common motifs; category B, including those containing one of the 8 common motifs and a motif other than one of the 8 common motifs; and category C, including those containing that two or more motifs other than the 8 most frequent motifs. A comparison of these three categories over the three sets of synthetic promoters revealed a dramatic increase in the number of category A composites in the SLA and S sets (3 and 5.7-fold, respectively) over that observed in the U set as well as in category B composites (2.7-fold for SLA and S sets). Category C composites also increased in the S set as compared to the U set (about 2.4-fold), but only increased 1.4-fold in the SLA set. These analyses indicate that composites containing one or more of the 8 frequent motifs correlate favorably with highly active synthetic promoters.

TABLE 1

| RANDOMER | SEQUENCE | MOTIF | ACTIV. |
|---|---|---|---|
| MS44 | cactcaCCTGTCCGCCGCACTTGTtaaatcacacgtgafccaCCAGGAAGTGAC GTATCAcgagcg (20) | SP1, EBOX, ETS, TRE, CREB, GATA | 56 |
| S173 | cgctcgCAACTCTTTCCCCCCCCCtggaccacgcgtgatccaCCAGGAAGTGAC GTATCAcgagca (21) | MAZ, ETS, TRE, CREB, GATA | 48 |
| MS72 | gatccaGGGAGGGGTAGGGTCTATcgagcaacgcatcactcgTCTCCTCTACAC CCGCTGtggatcacacgtcactcoTTGCCCTCCCCTTCCTCAtogatcacocgt cgctcgCTGTCCCCGCCCCACTCCtagatc (22) | MAZ/SP1, EA1, GATA, ETS, MAZ, ETS, GRE, SP1, P300 | 43 |
| MS143 | gatccaAGAGCGGGCAGGGGATTGGcgagcgacgcgtcgtcgctcgTCCCGCCC CCTCTATGCTtggatcacflcgtcgctcgTCCTCTTCTTTCCTTCCCtggatc (23) | UPA, CEBP, SP1, GRE, IE1, ETS | 43 |
| MS115 | cgctcgGCXJCCGCCCTCTTCCCCCtggatc (24) | SP1, GRE | 39 |
| S107 | cgctcgCTCTTGTGTACCTCTCCTtggateacgcgtcgctcaCCATCTTCrTGT CGCTGCtggatc (25) | HES, ETS, CF1, GRE, YY1 | 24 |
| MS91 | cgctcgTCTCTTCTCGCCCCCCCCtggate (26) | GRE.AP2 | 22 |

TABLE 1-continued

| RANDOMER | SEQUENCE | MOTIF | ACTIV. |
|---|---|---|---|
| MS137 | cgctcgCCCCTCCCCTAAGCGCGTtggatcacgcgtgatccaACGGGCAATGAA ACGAATcgagcg (27) | MAZ, TBF, myb, ECR | 16 |
| S125 | cgctcgCTGGCCCCGCCCTTAGTTtggatcacxicgtcgctcgACCCCGCCTTT CGTATCTtggatc (28) | SP1, SRY, GATA | 15 |
| MS165 | cgctcgTCGCCTGGGTTCTGCTActggatcacxjcgtgatccaGAAGAGCGGAA GGAGGGAcgaacg (29) | AP2, CP2, GRE, SP1 | 12 |
| MS144 | cgctcgCCTTCCCTTACTTCACGCtggatc (30) | CEBP/CREB | 12 |
| MS19 | cgctcoCCTCACGCGAATTCCCCCtggafcacocgtgatccaGAGAAGGGAGGG GGGGAcaagcg (31) | NFKB, MAZ7SP1 | 11 |
| MS113 | gatccaGGGGCAAAAAGGGAGGGGcgaacg (32) | MAZ/SP1 | 10 |
| MS25 | gatccaGGTGGGGCTAGTGACGTGcgaacg (33) | EBOX, SP1, CREB | 10 |
| S153 | gatccaGATAGACGGGAGTGAAAAcgagcgacgcgtgatccaAGCGGAGGAGGG ATGTGAcgagcg (34) | GATA, S1F1, P300, SP1, CREB | 9 |
| S158 | gatccaATCAAGGAGGAGGGATAGcgaacgacgcgtcgctcgTTTCCGGTCTTA TGTTTGtqgatc (35) | PBX.SP1, GATA, ETS, HNF5 | 9 |
| S185 | cgctcgCCCCCCGCCCTCTTTGCCtggatcacgcgtgatccaGGTGGGGCTAG TGACGTGcgacgc (36) | SP1, EBOX, SP1, CREB | 9 |
| MS123 | gatccaGAAAAGTGAGGGGAGGGGcgaocg (37) | TRE, MAZ/SP1 | 9 |
| MS77 | gatccaGGGACAGTGAGGGGGGGAcgagcgacgcgttgctcgTCCATTTCACGC CCCCGCtggatc (38) | GRE, MAZ, CF1, E2F, KROX | 8 |
| MS135 | gatccaACTGGAGAGTAACGCCCTcgagcg (39) | EBOX, TRE, SP1 | 8 | sequences corresponding to known motifs are underlined; bold and italics identify indicated motif imbedded within larger motif.
SEQ ID NOS: are indicated in parentheses at end of sequences.
"ACTIV." indicates promoter activity of sequence relative to minimal promoter.

The number of composites containing each of the 8 frequent motifs also was determined. In synthetic promoters of the SLA and S sets, as compared to the U set, the number of composites containing GRE, Ebox, API, CREB, and SP1/MAZ motifs increased dramatically and those containing ETS increased moderately. However, no increase was observed in the number of composites containing AP2 and CEBP elements. Taken together with the results described above showing the increased Ebox, CREB, API, and SP1/MAZ motifs in the SLA and S sets, these results demonstrate that 1) increases in both number and presence in composites of the E-box, AP1, ETS, CREB, and SP1/MAZ were correlated with active synthetic promoters; 2) an increase in the occurrence of GRE elements in composites but not in their abundance were correlated with active synthetic promoters: and 3) there was no correlation between either the number or the presence in composites of AP2 and CEBP elements with activity of synthetic promoters. Of the active Ran18 sequences from the SLA and S sets, 4% and 11%, respectively, showed no matches to known transcriptional regulatory motifs. As such, these sequences represent novel regulatory elements.

To determine whether some of the 8 most frequent motifs identified within the Ran18 sequences actually contributed to DNA binding and promoter activity, gel mobility-shift and promoter assays were performed on native and mutated versions of the ETS, CREB, and MAZ/SP1 motifs in the synthetic promoters MS44 (SEQ ID NO: 20) and MS113 (SEQ ID NO: 32; see Table 1). The right hand element found in MS44 (designated MS44B) and the Ran18 element in MS113 were examined for binding to Neuro2A nuclear extracts. MS44B contains an ETS/CREB composite and MS113 contains a MAZ/SP1 motif.

Gel mobility-shift experiments using the MS448 probe revealed high and low molecular weight DNA/protein complexes. Formation of high and low molecular weight complexes was eliminated in $^{32}$P-labeled variants of the MS448 sequence, ΔC and ΔE, which have multiple base pair substitutions in the CREB and ETS motifs, respectively. A probe having both ETS and CREB mutations (ΔEΔC) showed no binding to proteins in nuclear extracts of Neuro2A cells. Experiments that included these and mutated versions of these motifs as cold competitors in binding reactions provided similar results. These results indicate that the proteins involved in the higher and lower molecular weight complexes represent members of the CREB and ETS families of proteins, respectively. ETS and CREB mutations in MS446 also resulted in substantial reductions of MS448 promoter activity. Luciferase reporter variants of MS448 with mutations in the ETS, the CREB, or in both ETS and CREB motifs had only 27%, 5%, and 3%, respectively, of the promoter activity of MS44B.

Similar binding and activity assays were performed to investigate the efficacy of the SP1/MAZ motif in the MS113 (SEQ ID NO: 32; Table 1). Mutation of the SP1/MAZ motif resulted in a complete elimination of DNA binding of Neuro2A nuclear proteins to the MS113 element. A variant of the MS113 synthetic promoter containing these SP1/MAZ mutations showed only 18% of the promoter activity of MS113. Collectively, these experiments indicate that the ETS/CREB composite and SP1/MAZ motifs identified in searches of the TransFac database with the RIGHT software are major contributors to both the binding and activity of the synthetic promoters in which they were found.

SPCM was designed to address several problems confronted in analyzing the complex machinery of eukaryotic gene transcription. A basic problem is to survey the types and frequencies of DNA motifs that contribute to promoter activity. As such, it is important to understand which combinations of cis and trans elements work in concert with a core promoter and the basic transcription machinery in a given cellular context. The present results demonstrate that the disclosed methods can be used to identify functional motifs active in the context of a cell, including in various cell types, under a variety of conditions, and in various combinations.

After GFP selection of 480 sequences, 120 had greater than 4-fold activity over that of the minimal promoter in luciferase assays. The RIGHT software package was used to analyze the occurrence of various motifs in three different sets of synthetic promoters: unselected (the U set), those selected by GFP fluorescence to have promoter activity as integrants in the genome (the S set), and GFP-selected synthetic promoters that, as measured after cellular transfection, gave high levels of activity in an episomal state with the luciferase assay (the SLA set). Approximately twice as many matches with known transcriptional regulatory motifs were found in the SLA and S sets than were found in the U set. Fifty-one percent of the matches were with eight different motifs—AP2, CEBP, GRE, Ebox, ETS, CREB, AP1, and SP1/MAZ, and the most active sequences were made up of composites of these eight motifs, including the two most active sequences, both of which contained overlapping ETS and CRE motifs. A BLAST search for occurrence of this composite in natural promoters revealed an exact match with an element in the proximal promoter of a gene encoding a non-structural protein from the parvovirus B19 (Zakrzewska et al., GenBank Accession No. AF190208, 1999).

Of the eight prevalent known motifs identified using SPCM, several, including SP1, function within the core promoter (see, for example, Parks and Shenk, *J. Biol. Chem.* 271:4417-4430, 1996; Segal et al., *J. Mol. Evol.* 49:736-749. 1999). Others such as ETS and CRE are components of enhancers. Thus, the SPCM method provides a means to identify motifs that can act due to direct contributions to a core promoter and that can function within an enhancer.

The present methods allows for separate determinations of the activity of a motif when integrated in the genome or in the episomal state. Of 480 integrated motifs that were selected as active by GFP-sensitive cell sorting, 120 exceeded the 4-fold threshold as plasmids in the luciferase assay. Thus, the present method Selected transcriptional regulatory elements or combinations thereof as disclosed herein, for example, in matrix arrays, can be used to detect differential responses of normal cells and cells from various diseased tissues for diagnostic purposes or drug development.

EXHIBIT 3

Modification of the Transcriptional Regulatory Element Selection System

This example demonstrate that various vector constructs and reporter molecules can be used for identifying synthetic transcriptional regulatory elements.

The retroviral vector, MESVR/EGFP*/IRESNCAMPro(ori) (SEQ ID NO: 9), was made essentially by substituting a cDNA sequence encoding the 140 kD form of the human neural cell adhesion molecule, N-CAM, for the Pac coding sequence in the MESVR/EGFP*/IRESpacPro(ori) vector (SEQ ID NO: 1). The entire N-CAM cDNA was generated by PCR using 5' and 3' primers having Afl III and Sal I restriction sites, respectively. The selection system based on N-CAM uses an anti N-CAM antibody, which immunoreacts with eukaryotic cells that are expressing N-CAM under the control of an introduced synthetic oligonucleotide having transcriptional promoter activity. Selection can be performed, for example, by fluorescently labeling the anti-N-CAM antibody, contacting the cell with the antibody, and using a method such as FACS to select retroviral infected cells expressing the N-CAM marker.

The disclosed selection method also can be practiced using other expression vectors, including variants of the disclosed retroviral vectors. For example, the adenovirus major late promoter can be substituted with another minimal promoter such as the minimal enkephalin gene promoter (MEK). In addition, a nucleotide sequence encoding a reporter protein other than EGFP or puromycin can be used. For example, EGFP can be substituted with GFP or another fluorescent reporter, or with luciferase or other easily detectable reporter. Similarly, the nucleotide sequence encoding puromycin N-acetyltransferase can be substituted with one encoding hygromycin B phosphotransferase, which confers resistance to hygromycin B, the provides a means to identify regulatory elements that function only when integrated in a genome. The possibility that some of the activities seen in the integrated state arose because of proximity to unknown enhancers raises the issue of false positive responses.

In comparison to the use of retroviral infection and integration, which requires cell division, transfection and antibiotic resistance against selection by Zeocin® were used to construct stable cell lines that achieved results similar to those reported using the retroviral vector. However, integration of promoter constructs was less efficient than when a retroviral vector was used. The use of retroviruses allows application of SPCM to cells in an organism in vivo, thus providing a means to identify regulatory elements that are active only during particular stages of development.

Variations to the present method include, for example, the screening of libraries constructed from different lengths of randomers to minimize potential biasing. Moreover, the use of larger cell sample can improve statistical analysis of the prevalence of particular motifs. In addition, application of the present method to screening in various cell types and species can elucidate evolutionary changes in regulatory elements that occur, for example, as a result of speciation events, thus providing a means to classify an unknown sample. Consistent application of the current and related SPCM approaches should allow the creation of databases of truly functional promoters and also include cognate information on various species and developmental states.

Several extensions of the SPCM procedure can be useful. For example, in addition to the selection of random DNA sequences of a particular length, the method can be used to analyze combinations of a single known motifs such as an Octamer element with random sequences, thus providing a means to identify synergies between various cis acting regulatory elements and the modulation of interactions with corresponding transcription factors. Moreover, the deliberate assemblage of combinations of known elements in various lengths, orders, polarity, and spacings can provide a means to obtain regulatory elements having desirable characteristics. Sh ble gene product, which confers resistance to the antibiotic Zeocin® (bleomycin), or neomycin (aminoglycoside) phosphotransferase, which confers resistance to the aminoglycoside antibiotic, G418. Non-retroviral expression vectors also can be used, and similarly are designed to contain one or more polynucleotides encoding selectable markers such that cells containing an integrated form of the vector can be selected.

Figure 2A:
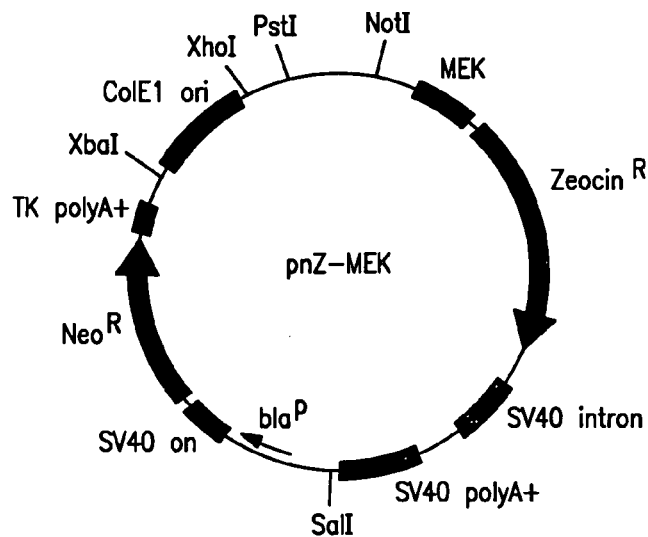
FIG. 2A illustrates the vector pnZ-MEK (SEQ ID NO: 2). Various restriction endonuclease recognition sites are indicated. MEK indicates minimal enkephalin promoter; Zeocin®, NeoR and bla$^P$ indicate coding sequences for polypeptides conferring Zeocin® (bleomycin), neomycin and kanamycin resistance, respectively. SV40 intron and SV40 polyA$^+$ signal sequence are indicated. TK polyA$^+$ indicates thymidine kinase polyA$^+$ signal sequence. ColE1 ori indicates *E. coli* origin of replication.

Additional exemplary vectors useful in the disclosed methods are provided. The pnZ-MEK vector (SEQ ID NO: 2; see, also, FIG. 2A) contains a MEK minimal promoter and nucleotide sequences encoding the prokaryotic Sh ble gene product and the neomycin (aminoglycoside) phosphotransferase, which confer resistance to antibiotics Zeocin® and G418, respectively. The pnZ-MEK vector also contains unique Pst I and Not I restriction sites, into which an oligonucleotide to be tested for transcriptional regulatory activity, for example, Ran18 or Ran12 cassettes or other putative regulatory elements can be inserted. Elements are cloned upstream of the MEK promoter upstream of the Zeocin (bleomycin) resistance gene.

Figure 2B:
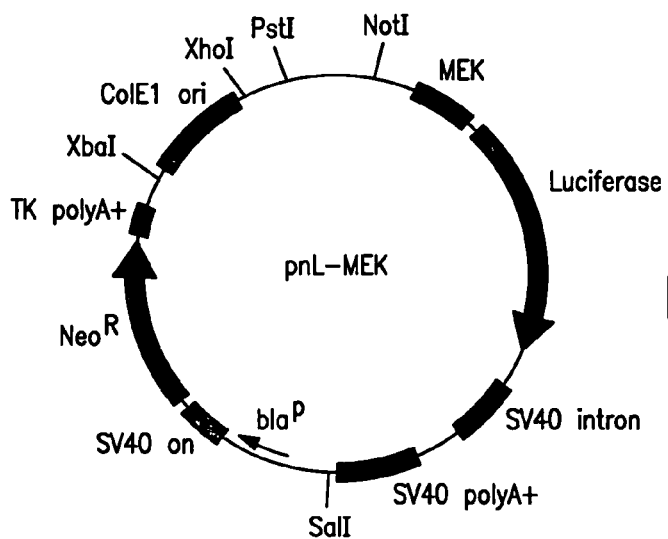
FIG. 2B illustrates the vector pnL-MEK. Various sites and sequences are as in FIG. 2A. Luciferase indicates luciferase coding sequence.
Figure 2C:
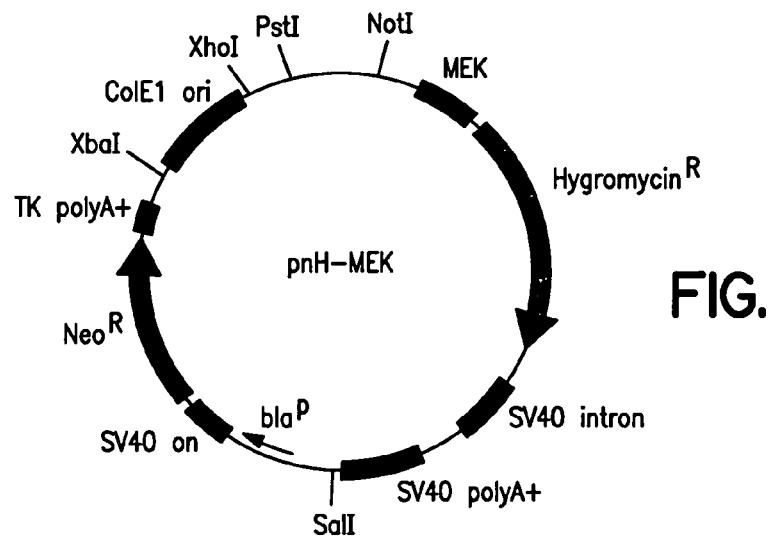
FIG. 2C illustrates the vector pnH-MEK (SEQ ID NO: 3). Various sites and sequences are as in FIG. 2A. Hygromycin$^R$ indicates coding sequence for polypeptide conferring hygromycin B resistance.

The pnL-MEK vector (see FIG. 2B) is similar to pnZ-MEK, except it contains a luciferase reporter gene substituted for the Sh ble gene, and can be used to corroborate the activity of regulatory elements that are selected in the procedure. An additional vector, pnH-MEK was constructed by substituting the sequence encoding Sh ble (or luciferase) reporter gene of pnZ-MEK (or pnL-MEK) with one encoding hygromycin B phosphotransferase, which confers resistance to hygromycin B (SEQ ID NO: 3; see, also, FIG. 2C). Each of these vectors contain a gene encoding neomycin resistance (aminoglycoside) phosphotransferase, which is driven by the strong SV40 early promoter. The neomycin resistance gene cassette allows selection for integration of a construct in the cellular genome using G418. In addition, the vectors contain a sequence encoding β-lactamase (bla), which confers resistance to kanamycin and allows for selection of the vectors in bacterial cells.

To confirm the utility of the above described expression vectors, a library of random 12mers was screened. Single stranded oligonucleotides containing a core of twelve random bases (Ran12) were synthesized using an Applied Biosystems DNA synthesizer, and annealed to two linkers forming a hemiduplex DNA with double stranded termini having Pst I and Not I compatible ends. To prepare the double stranded Ran12 oligonucleotides, two additional primers complementary to the Pst I and Not I portions of the single stranded oligonucleotide were synthesized and annealed to the Ran12 oligonucleotides. The annealing forms a hemiduplex DNA molecule that contains double-stranded ends that are compatible with Pst I and Not I restriction sites and a single-stranded portion that corresponds to the Ran12.

Annealing was performed with a 50-fold molar excess of the two primers relative to the Ran12 oligonucleotide in a solution containing Tris-HCl (pH 7.5), 1 mM $MgCl_2$ at 75° C. for 10 min, followed by slow cooling to room temperature. The library of Ran12 oligonucleotides was ligated into either the pnL-MEK or pnZ-MEK vectors in a 1:1 ratio of Ran12 oligonucleotide to vector. Generally, 100 to 500 ng of vector was used in each ligation in a volume of 10 μl. DNA was then purified using QiaQuick PCR purification columns (Qiagen) and 10% of the ligation mixture was used to transform frozen competent XL 10 Gold E. coli (Stratagene). DNA polymerase I in the bacteria fills-in the hemiduplex, thus producing a double stranded Ran12 sequence. Equal portions of the transformation mix were plated on 150 mm LB plates containing kanamycin.

Several cell lines can be used for transfection. The P19 cell line is a model system for the study of neuronal and muscle cell differentiation. In the presence of retinoic acid, the embryonal P19 cells differentiate into glial cells and neurons, whereas in the presence of DMSO, P19 cells differentiate into skeletal and cardiac muscle cells. Furthermore, these cells differentially express genes that are important to these induction processes. Regulatory elements identified as active in the P19 differentiation system can be tested in other cell lines of known phenotype to further define the role of the element in a particular step of differentiation. Other cell lines that can also be induced to differentiate include NG108-15 and Neuro2A cells. Although the latter cells are not pluripotent as is the P19 cell system, they provide a means to focus on more specific differentiation events within the nervous system.

The Ran12/pnZ-MEK constructs were introduced into P19 cells by electroporation using a BIORAD Gene Pulser, which results in the insertion of the expression constructs into one site within the genome. Electroporation was performed in either growth medium or Opti-MEM using 10 jug of linearized DNA in $15 \times 10^6$ cells. After electroporation, stably transfected cells were selected in 10 cm dishes in the presence of both G418 (0.2 mg/ml) and Zeocin® (0.1 mg/ml). Cells were selected for 2 weeks and colonies that survive were transferred to 96 well plates. Once stable cell lines were established, cells were induced to differentiate within the 96 well plates. In the first set of isolated Ran12 promoter elements, four million synthetic Ran12 elements were screened, and one thousand Zeocin-resistant cell colonies were isolated.

Cell lines were analyzed to identify the combinations of known elements or novel regulatory elements that allowed sufficient Zeocin® expression for survival. Cells were cultured in 96 well plates and genomic DNA was isolated using a Chelex lysis procedure and purified using the QiaAmp Tissue Kit (Qiagen). Regulatory elements were amplified by PCR (two rounds of 25 cycles) using primers that flank the regulatory element cassette. The amplified regulatory cassette was sequenced directly using the automated DNA sequencer. To independently assay the activity of elements selected in stable lines, each cassette was cloned into the pnL-MEK vector in order confirm and quantitate the activity of individual elements. Each luciferase reporter containing an element was transiently transfected into cells using Lipofectamine (Life Technologies) and luciferase activity was assayed 48 hr later using an enzymatic assay and detected on a luminometer.

A number of synthetic regulatory constructs that functioned well in a particular cell type and cell culture environment were identified and compared to others selected from cells cultured in a different environment to determine profiles of regulatory elements that function best in a particular cell and culture environment. Representative Ran12 sequences obtained by this selection procedure are shown in Table 2 (SEQ ID NOS: 40 to 82). Elements that resembled portions of the binding sites for known transcriptional regulatory proteins, including homeodomain binding sites, CCAAT boxes, CACCC boxes, binding sites for c-myb, hormone response elements (glucocorticoid receptor, progesterone receptor and estrogen receptor), binding sites for the products of immediate-early genes such as fos and jun and Ap-2, and other factors including C/EBP, USF, Zeste, and TBP are indicated. Elements that were selected by this procedure, but that do not contain otherwise identifiable known binding sites for transcription factors, also are indicated. Remarkably, several different core motifs were identified, including TTGGGT (SEQ ID NO: 83) present in SEQ ID NOS: 63 to 71, CTAGTGGG (SEQ ID NO: 84) present in SEQ ID NOS: 72 to 74, ATGCC (SEQ ID NO: 85) present in SEQ ID NOS: 75 and 76, GAAGG (SEQ ID NO: 86) present in SEQ ID NOS: 77 and 78, and CTTTTGCA (SEQ ID NO: 87) present in SEQ ID NOS: 79 and 80 (see Table 2). In addition, some Ran12 sequences were obtained more than once (see Table 1; SEQ ID NOS: 42, 68, 81 and 82). These results confirm the general utility of the disclosed methods for identifying transcriptional regulatory elements having a variety of lengths.

TABLE 2

1. Elements that resemble known transcription factor binding sites

Homeodomain factor binding sites

| | |
|---|---|
| GGCATTCATCGT | Pit-1a (40) |
| GCATTAGTATCT | IsI-1 (41) |

CAATbox

| | |
|---|---|
| TCGGTTATTGTT | (42) |
| TCCAATTGGGAA | (43) |
| ATCTATTGGCCA | gamma CAAT (44) |

CACCCbox

| | |
|---|---|
| TTACTGGGTGTT | (45) |
| AGGGTGAAGGTC | (46) |
| GGTGGGTGTGTC | (47) | c-myb

| | |
|---|---|
| CGCTTCAATGCT | (48) |
| TGCTTCAATGCC | (49) |

Hormone response elements (HRE)

| | |
|---|---|
| TGTGTCTTTGCA | GR (50) |
| CACGGGGACAGC | GR (51) |
| AAGCTGTACATG | GRPR (52) |
| GATGGGGCACA | GR (53) |
| ATATGTGCCCTT | GR (54) |
| TCCTTCTGGGTC | ER fos/jun (55) |
| GGTGGGTGTGTC | GR AP1 (56) |

Other

| | |
|---|---|
| GAATGGATGGGG | AP-2 (57) |
| CAXGTGATATTC | USF (58) |
| AGGAGGGTTTGT | C/EBP alpha (59) |
| TGGGCGAGTGGG | Zeste (60) |
| CGGCTCACCAGT | Zeste (61) |
| GGTTTCXATAAC | TBP (62) |

2. Novel elements

Repeated core motifs

| | |
|---|---|
| GGTGGGTGTGTC | (63) |
| TTACTGGGTGTT | (64) |
| AAGTCTTTGGGT | (65) |
| GGTTGGGTCCCC | (66) |
| TTGGGTCATTGT | (67) |

TABLE 2-continued

| | |
|---|---|
| TTGGGTCGTTGT | (68) |
| TCTGGGTCGCGC | (69) |
| TCCTTCTGGGTC | (70) |
| CCTTTGTGGGTC | (71) |
| TCACTTCTGGGC | (72) |
| CTAGTGGGAGCT | (73) |
| TGGGCGAGTGGG | (74) |
| TGCTTCAATGCC | (75) |
| CGCCTCGATGCC | (76) |
| AGGGTGAAGGTC | (77) |
| ACCCGGGGAAGG | (78) |
| TGTGTCTTTGCA | (79) |
| CGAACTTTGCAA | (80) |

Elements found more than once

| | |
|---|---|
| TTGGGTCGTTGT | found 4 times (68) |
| TGAGTAAGCTAT | found twice (81) |
| TATGTAAGAACG | found twice (82) |
| TCGGTTATTGTT | found twice (42) |

EXAMPLE 4

Selection of Synthetic Translational Regulatory Elements

This example describes the preparation of a vector useful for selecting oligonucleotide sequences having internal ribosome entry site (IRES) activity and the identification and characterization of such selected elements.

The disclosed synthetic IRES methodology provides a means for selecting functional IRES elements. Similar to the transcriptional regulatory element selection method disclosed above (Examples 1 to 3), the IRES selection method allows the parallel screening of $1 \times 10^6$ to $1 \times 10^{10}$ or more random oligonucleotide elements or combinations of elements for activity in mammalian cells. Selection of synthetic IRES elements in mammalian cells is facilitated if 1) each cell receives a single unique cassette to avoid selection of inactive elements that are fortuitously present in the same cell as an active element; 2) the delivery system is efficient so that a complex library can be readily screened; and 3) the selection process is stringent and is based on a reporter gene assay that is highly sensitive and faithfully reports the activity of the IRES elements.

As disclosed herein, a library of oligonucleotides was ligated immediately upstream of the second nucleotide sequence of a dicistronic reporter cassette comprising two reporter genes by insertion into a cloning site in the intercistronic spacer sequence. The exemplified reporter cassette (see below) contained nucleotide sequences encoding enhanced green fluorescent protein (EGFP) and enhanced cyan fluorescent protein (ECFP), which were arranged in a dicistronic construct that allows two separate gene products to be made from a single mRNA that is driven by a single promoter. After infection of cells with the retroviral IRES element library and integration into the genome, each IRES was scored for its translational activity by examining the activity of the ECFP reporter gene relative that of EGFP. After 2 to 3 days of infection, uninfected cells were selected by FACS to obtain cells expressing both EGFP and ECFP; the level of ECFP expression in each cell reflected the strength of an individual synthetic IRES element cassette, such that highly fluorescent cells are likely to contain highly active IRES elements. After multiple rounds of selection, the IRES sequences were amplified from the cellular genome by PCR and sequenced using an automated DNA sequencer to determine the identity of each of the synthetic IRES elements. The activity of each selected IRES element was confirmed by amplifying the entire IRES element, inserting the amplified element into a dicistronic luciferase reporter vector, and screening for the second luciferase reporter protein under translational control of the inserted IRES. This method allowed the testing of the regulatory cassette in a different reporter system, which was more amenable to quantitation of IRES activity levels.

Figure 3:
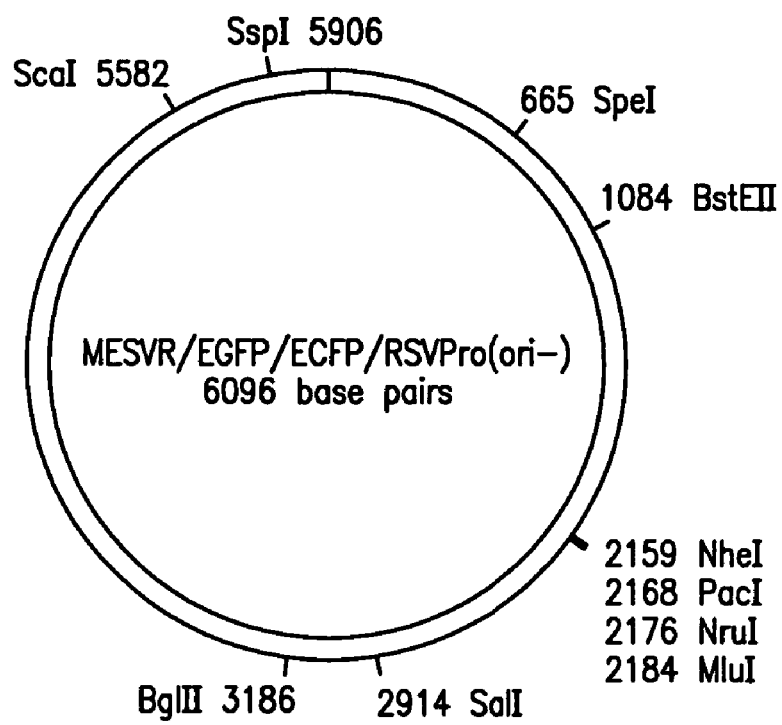
FIG. 3 illustrates the retroviral vector MESVR/EGFP/ECFP/RSVPro(ori-) (SEQ ID NO: 109). Various restriction endonuclease recognition sites are indicated.

The benefits of using a retroviral delivery system for identifying synthetic IRES elements are similar to those described in Example 1 for identifying transcriptional regulatory elements. The recombinant retroviral vector designed for the IRES selection procedure was designated MESVR/EGFP/ECFP/RSVPro (SEQ ID NO: 109; see, also, FIG. 3). This vector was based on the MESV/IRESneo (Owens et al., supra, 1998; Mooslehner et al., supra, 1990; Rohdewohld et al., supra, 1987), similarly to the MESVR/EGFP*/IRES/pacPro(ori) vector (SEQ ID NO: 1) described in Example 1.

Features of the MESVR/EGFP/ECFP/RSVPro vector include that 1) a multiple cloning site was introduced into the downstream LTR for insertion of the exogenous sequences that can regulate transcriptional activity of a transgene encoded by the recombinant retrovirus, and the endogenous viral core promoter was replaced with a strong basal promoter to potentiate transcription promoting activity of inserted sequences; 2) a mutated EGFP encoding sequence followed by a multiple cloning site to allow insertion of elements to be tested sequences and a sequence encoding ECFP to allow assay of translation^ activity on a single cell basis was introduced; 3) enhancer elements in the upstream LTR were replaced with those from RSV to drive higher levels of RNA genome production in the packaging cells; and 4) an SV40 origin of replication was inserted in order to increase the copy number of the retroviral plasmids in the packaging cells. The EGFP and ECFP reporter genes are expressed as a single transcript, in which the mRNAs are linked by an oligonucleotide to be examined for IRES activity. Expression of both reporter genes is controlled by a strong RSV promoter to ensure efficient transcription of the RNA viral genome and, therefore, a high viral titer. The multiple cloning site between the EGFP and ECFP coding sequences facilitates the insertion of an oligonucleotide to be examined for translational activity.

Except as indicated, methods were performed essentially as described in Examples 1 to 3. A pool of random 18mers, flanked on either side by two different invariant sequences each 6 base pairs in length, was prepared and inserted into the Mlu I site in the intercistronic spacer of MESV/EGFP/ECFP/RSVPro (see FIG. 3; cf. FIG. 1). A library of recombinant retroviruses was made by transiently transfecting COS1 cells together with plasmids encoding the MLV gag/pol genes and the VSV G glycoprotein gene. The library was introduced into B104 cells, then 48 In-later, the cells were subjected to FACS and cells expressing high levels of EGFP and ECFP were collected. The selected cells were replated, then sorted again for EGFP and ECFP expression. Genomic DNA was extracted from the twice-selected cells, and the 18mers were isolated by PCR using primers complementary to the sequences flanking the Mlu I cloning site in the vector.

IRES activity of the PCR amplified sequences was confirmed by cloning the fragments into the intercistronic region of the dicistronic reporter vector, RPh (Chappell et al., *Proc. Natl. Acad. Sci., USA* 97:1536-1541, 2000, which is incorporated herein by reference). Individual plasmid clones were transfected into B104 cells and the luciferase activities of the first cistron (*Renilla* luciferase) and the second cistron (*Photinus* luciferase) were assayed. For a given plasmid clone containing a particular 18mer sequence, an increase in the translation of the second cistron relative to the first cistron and normalized to the empty vector indicated that the 18mer functioned as an IRES element.

EXAMPLE 5

Modification of the Translational Regulatory Element Selection Method

This example demonstrates that various vectors and reporter cassettes can be used to identify synthetic translational regulatory elements.

In higher eukaryotes, translation of some mRNAs occurs by internal initiation. It is not known, however, whether this mechanism is used to initiate the translation of any yeast mRNAs. In this example, naturally occurring nucleotide sequences that function as IRES elements within the 5' leader sequences of *Saccharomyces cerevisiae* YAP1 and p150 mRNAs were identified. When tested in the 5' UTRs of monocistronic reporter genes, both leader sequences enhanced translation efficiency in vegetatively growing yeast cells. Moreover, when tested in the intercistronic region of dicistronic mRNAs, both sequences exhibited IRES activity that functioned in living yeast cells. The activity of the p150 leader was much greater than that of the YAP1 leader. The second cistron was not expressed in control dicistronic constructs that lacked these sequences or that contained the 5' leader sequence of a control (CLN3) mRNA in the intercistronic region. Further analyses of the p150 IRES revealed that it contained several non-overlapping segments that were able independently to mediate internal initiation. These results demonstrate that the pi50 IRES has a modular structure similar to IRES elements contained within some cellular mRNAs of higher eukaryotes. Both YAP1 and p150 leaders contained several complementary sequence matches to yeast 18S rRNA.

The plasmid pMyr (Stratagene) was used as backbone for both dicistronic and monocistronic constructs. An adaptor containing restriction sites Hind III, Pst I, Nhe I, Eco RI, Nco I, and Xba I was introduced into the pMyr vector immediately downstream of the GAL1 promoter, using Hind III and Xba I as cloning sites. The Pst I and Xba I sites were used as cloning sites for a fragment from the RPh dicistronic reporter vector (Stoneley et al., *Oncogene* 16:423-428, 1998, which is incorporated herein by reference; Chappell et al., supra, 2000). The resulting construct, pMyr-RP, encodes a dicistronic mRNA that encodes *Renilla* (sea pansy) and *Photinus* (firefly) luciferase proteins as the first (upstream) and second (downstream) cistrons, respectively. These cloning steps resulted in a 5' UTR that differs slightly from that in the RP mRNA described previously (Stoneley et al., supra, 1998; Chappell et al., supra, 2000). The CYC1 terminator sequence contained within pMyr-1 vector provides signals for termination of transcription and polyadenylation.

The p150, YAP1, and CLN3 leader sequences were PCR amplified using yeast genomic DNA as a template. These leader sequences were cloned into the intercistronic region of the pMyr-RP vector using Eco RI and Nco I restriction sites that were introduced at the 5' and 3' ends of the leader sequences to generate constructs designated as pMyr-p150/RP, pMyr-YAP1/RP, and pMyr-CLN3/RP. A hairpin structure with a predicted stability of −50 kcal mol"[1] (Stoneley et al., supra, 1998) was introduced into the 5' UTR of the dicistronic constructs to generate pMyr-p150/RPh, pMyr-YAP1/RPh, and pMyr-CLN3/RPh. Deletions and fragments of the p150 leader were generated by PCR amplification of the p150 sequence, again using Eco RI and Nco I as cloning sites.

Monocistronic constructs containing the *Photinus* luciferase gene were generated in the modified pMyr vector. The *Photinus* luciferase gene was obtained from the pGL3 control vector (Promega) as an Nco I/Xba I fragment and cloned using these same sites to generate construct pMyr/P. The leader sequences from YAP1, p150, and CLN3 mRNAs, as well as the hairpin structure were cloned into the pMyr/P vector using the same restriction sites used for the dicistronic constructs. Constructs containing the chloramphenicol acetyl transferase (CAT) gene were cloned into the pGAD 10 vector (CLONTECH). The pGAD 10 vector was digested with Hind III and an adaptor containing restriction sites Hind III, Pst I, Nhe I, Eco RI, Nco I, and Xba I was introduced into this site, which is immediately downstream of the ADH promoter. The CAT gene was obtained from the pCAT3 control vector (Promega) and cloned into the modified pGAD10 vector using Nco I and Xba I restriction sites. The p150 leader sequence was introduced into this vector as an EcoRI/NcoI fragment to generate the construct designated p150/CAT. The hairpin structure described above was introduced 5' of this leader sequence to generate the construct designated p150/CATh.

The yeast strain EGY48 (MATα, his3, trp1, ura3, LexA$_{op(X6)}$-LEU2; CLONTECH) was used throughout the study. Yeast strains harboring the pMyr based plasmids were grown overnight in 4 ml synthetic defined medium (SD) with uracil and glucose. The following morning, cells were harvested, washed with 4 ml H$_2$O, and grown for 3 hr in 4 ml SD medium without uracil with the addition of 2% galactose and 1% raffinose. Cells harboring the pGAD10-based constructs did not require induction and were cultured in 4 ml SD/Ura glucose medium overnight. Cells were lysed with 1× lysis buffer (diluted freshly from 5× stock; Promega) in tubes with glass beads. Tubes were vortexed twice for 30 sec and recovered in a microfuge spun at top speed for 3 min at 4° C. The supernatant was recovered and 20 µl of the lysate was used to assay luciferase activities using the dual reporter assay system (Promega). CAT activity was measured using N-butyl Co A according to technical bulletin no. 84 (Promega).

RNA was isolated from 4 ml cell culture samples. Cells were pelleted, washed with water, and resuspended in 400 ul of TES buffer (100 mM Tris-HCl, pH 7.5, 10 mM EDTA, 0.5% SDS). RNA was extracted using preheated phenol (65° C.); the mixture was vortexed for 1 min and incubated at 65° C. for one hr. Samples were put on ice for 5 min, then centrifuged at 15,000 rpm for 5 min and the top aqueous phase was collected, re-extracted with phenol once and chloroform once. RNA was precipitated with isopropanol, the precipitate was washed with 70% ethanol, dried and dissolved in water. RNA samples were separated by gel electrophoresis using 1% formaldehyde/agarose gels and transferred to Nytran Super-Charge nylon membrane (Schleicher & Schuell). The blots were probed with full-length fire-fly luciferase RNA antisense probe that was labeled with $^{32}$P.

The 164 nucleotide YAP1 leader sequence (SEQ ID NO: 88) was examined for translational regulatory activity in the 5' UTR of a firefly (Photinus) luciferase reporter mRNA (YAP1/P). Cells were transformed with constructs expressing the parent *Photinus* (−/P) mRNA, the YAP1/P mRNA, or the 364 nucleotide 5' leader of the CLN3/P mRNA as a spacer control. Transcription of these monocistronic mRNAs was under control of the GAL1 promoter; mRNA expression was induced with galactose, cells were lysed after 3 hr, and luciferase activities determined and normalized to *Photinus* luciferase mRNA levels. Translation efficiency of the YAP1/P mRNA was approximately 10-fold greater than that of either the control −/P or CLN3/P mRNAs. This result indicates that the YAP1 5' UTR has translational enhancing activity.

To determine whether the translation mediated by the YAP1 transcribed leader sequence has a cap-independent component, it was tested in a dicistronic mRNA for its ability to mediate internal initiation. The leader sequence of YAP1 mRNA was placed in the intercistronic region of a dual luciferase dicistronic mRNA and examined for IRES activity. In these mRNA transcripts, the upstream cistron encodes *Renilla* (sea pansy) luciferase and the downstream cistron encodes *Photinus* luciferase. Cells were transformed with constructs encoding the parent RP mRNA, or with constructs containing the YAP1 or CLN3 leaders in the intercistronic region of the RP mRNA. The YAP1 leader sequence enhanced the translation of the downstream *Photinus* luciferase cistron approximately 5-fold relative to that of the RP mRNA. In contrast, the CLN3 leader had almost no effect on the expression of the second cistron relative to that of the RP mRNA.

Hairpin structures were inserted in the discistronic constructs upstream of the *Renilla* luciferase gene to block scanning and, thereby, reduce the translation of this reporter molecule. The hairpin structures blocked *Renilla* luciferase expression by greater than 90%. Nevertheless, the YAP1 leader permitted translation of the *Photinus* luciferase gene, even when translation of the *Renilla* luciferase gene was blocked. This result demonstrates that the YAP1 leader did not increase expression of the second cistron by reinitiation or leaky scanning.

To exclude the possibility that enhanced expression of the downstream cistron was from shorter, monocistronic mRNAs generated by mechanisms such as RNA fragmentation or an unusual splicing event, RNA was isolated from transformed cells and analyzed by northern blot analysis using a probe to the downstream *Photinus* luciferase gene. The results demonstrated that the dicistronic mRNAs were intact. Thus, translation of the second cistron was not due to initiation via shorter transcripts. Together, these results demonstrate that the YAP1 5' UTR comprises a nucleotide sequence that has IRES activity and that has translational enhancing activity.

The yeast p150 5' UTR also was examined for translational regulatory activity. The 5' leader of the mRNA encoding the p150 protein was determined by primer extension analysis to contain 508 nucleotides (SEQ ID NO: 89; see, also, Goyer et al., *Mol. Cell. biol.* 13:4860-4874, 1993, which is incorporated herein by reference). This sequence contains 11 open reading frames (ORFs) and does not appear to contain or be part of an intron (Costanzo et al., *Nucl. Acids Res.* 28:73-76, 2000, which is incorporated herein by reference), consistent with the observation that only 4% of yeast genes contain introns, 90% of which encode ribosomal proteins. The presence of the upstream ORFs in the p150 leader might be expected to inhibit translation by a scanning mechanism.

The pi 50 sequence was tested in the 5' UTR of a monocistronic reporter mRNA. Constructs containing this sequence enhanced the translation efficiency of the reporter gene up to 10-fold. However, the analysis was complicated by the appearance of a second band approximately 1 kb, which may be a partial degradation product of the luciferase mRNA; this RNA was too short to encode a functional *Photinus* luciferase protein. Accordingly, the p150 leader was tested in the 5' UTR of the CAT reporter gene to further evaluate whether it was functioning as a translational enhancer. The results obtained using the CAT reporter construct were similar to those obtained with the *Photinus* luciferase reporter gene; the p150 leader sequence enhanced the translation efficiency of the CAT reporter gene 9-fold.

To determine whether any translation mediated by the p150 5' leader was cap-independent, a hairpin structure was inserted at the 5' end of this construct. Although the hairpin structure inhibited translation of a control CAT mRNA by greater than 90%, translation mediated by the p150 leader sequence was not inhibited but, instead, was enhanced by approximately 3-fold. The CAT mRNA levels did not appear to be affected. These results demonstrate that the translation mediated by this leader sequence is cap-independent.

To confirm that translation was cap-independent, the p150 leader was tested in the intercistronic region of the dual luciferase RP dicistronic mRNA. In this location, the p150 leader functioned as a potent IRES, enhancing translation of the downstream *Photinus* luciferase cistron approximately 200-fold relative to that of the RP parent vector. This increase in *Photinus* luciferase activity in the p150/RP mRNA resulted in *Photinus* luciferase protein levels that were approximately twice those of *Renilla* protein levels.

Blocking the translation of the upstream *Renilla* luciferase gene with a hairpin structure resulted in an even greater enhancement of the *Photinus-Renilla* luciferase ratio, indicating that the translation facilitated by this sequence was not dependent on the translation of the upstream *Renilla* luciferase cistron. As with the findings with YAP1, the enhanced expression of the downstream cistron was not associated with RNA fragmentation or unusual splicing events.

The p150 leader sequence was sequentially deleted from the 5' end and fragmented into shorter segments, including fragments consisting of nucleotides 100 to 508, 160 to 508, 250 to 508, 375 to 508, 429 to 508, 481 to 508, 250 to 390, and 1 to 250 of SEQ ID NO: 89, each of which was tested for IRES activity. Most of the IRES activity was associated with nucleotides 160 to 508. However, all of the fragments examined demonstrated some level of IRES activity. Furthermore, deletion of nucleotides 1 to 100 or nucleotides 100 to 160 increased translation by internal initiation, indicating that this 160 nucleotide region contains translational inhibitory sequences, which can inhibit IRES activity. The leader sequence in construct p150 (250-508) corresponds to that of a shorter leader sequence that occurs naturally (Goyer et al., supra, 1993). This shorter leader sequence has a level of IRES activity that is similar to that of the entire 508 nucleotide leader.

It was previously noted that many eukaryotic mRNAs contain short complementary sequence matches to 18S rRNA, raising the possibility that ribosome recruitment at some cellular IRESes might occur by base pairing between mRNA and 18S rRNA (Chappell et al., supra, 2000; Mauro and Edelman, *Proc. Natl. Acad. Sci., USA* 94:422-427, 1997; Tranque et al., *Proc. Natl. Acad. Sci., USA* 95:12238-12243, 1998; Hu et al., *Proc. Natl. Acad. Sci., USA* 96:1339-1344, 1999). Comparison of the YAP1 and p150 leader sequences to yeast 18S rRNA identified two and four complementary sequence matches, respectively, which contained stretches of up to 10 nucleotides of perfect complementarity (see FIG. 5). In addition, two of the matches are part of more extensive complementary matches of up to 25 nucleotides with 84% complementarity. The complementary match at nucleotides 130 to 142 of the p150 IRES (SEQ ID NO: 94; see FIG. 5) is correlated with a 60 nucleotide segment of the IRES that can inhibit IRES activity. Another complementary match of the p150 IRES at nucleotides 165 to 183 (SEQ ID NO: 96) is correlated with a 90 nucleotide segment of the IRES that contributes to internal initiation. Two other complementary matches of the p150 IRES at nucleotides 423 to 437 (SEQ ID NO: 98)

The p150 IRES element was particularly active. Although most of the IRES activity was localized to nucleotides 160 to 508 (SEQ ID NO: 89), the IRES boundaries were not distinct. Moreover, several non-overlapping segments functioned independently, suggesting that this IRES has a modular composition. In a previous study of the IRES contained within the mRNA that encodes the Gtx homeodomain protein, the apparent modularity was pursued to identify a 9 nucleotide segment that functioned independently as an IRES module (see Chappell et al., supra, 2000).

The notion that short nucleotide sequences can recruit the translation machinery is not consistent with the proposal that higher order RNA conformations are uniformly important for the activity of some cellular IRESes. Indeed, the results obtained from deletion and fragment analyses of IRESes contained within other mammalian and insect cellular mRNAs indicates that many of these IRESes may also be modular (see, for example, Yang and Sarnow, *Nucl. Acids Res.* 25:2800-2807, 1997; Sella et al., *Mol. Cell. Biol.* 19:5429-5440, 1999). The modular composition of cellular IRESes contrasts with those found in viruses. For example, in picornaviruses, the IRESes comprise several hundred nucleotides and contain RNA conformations that appear to be highly conserved and that are important for activity.

It is not known how widely internal initiation is used by yeast or higher eukaryotic mRNAs. The identification of numerous insect and mammalian IRESes may reflect a more extensive use of this mechanism in higher eukaryotes, or it may reflect incidental bias that has resulted in the evaluation of many more mRNAs from insects and mammals than from yeast. Some mammalian IRESes do not function in living yeast. In the case of poliovirus, the inactivity of its IRES in *S. cerevisiae* reflects a specific blockage that occurs via a short inhibitory RNA. The inactivity of some mammalian IRESes in yeast may also reflect trans factor requirements that are not provided by yeast cells or differences related to the ability of a sequence to bind a component of the translation machinery that is not identical to that in yeast. For example, p150 is the yeast homologue of mammalian translation initiation factor eIF4G, but the two are not functionally interchangeable.

In higher eukaryotes, IRESes are used by some mRNAs during the G2/M phase of the cell cycle and under conditions that reduce cap-dependent translation, as seen, for example, during different types of stress. In yeast, internal initiation may also be used to facilitate the translation of essential genes under similar conditions, including the condition of nutritional deficiency. It may be significant that IRESes were identified within the YAP1 and p150 leader sequences given that overexpression of YAP1 confers general resistance to many compounds. In addition, expression of p150 when cap-dependent translation is reduced may contribute to the translation of other mRNAs under these conditions.

The identification of yeast IRESes that function in vegetatively growing cells suggests that yeast and higher eukaryotes use similar mechanisms to initiate translation. The analysis of these mechanisms should be facilitated in yeast, since many strains of yeast exist with mutations in genes involved in translation. The ability to easily manipulate this organism genetically may also enable the identification of specific factors involved in internal initiation and should enable us to critically test the hypothesis that base pairing between certain IRES sequences and 18S rRNA is important for recruitment of ribosomes at these sites. In addition to these scientific interests, the identification of yeast IRESes that function as translational enhancers in monocistronic mRNAs also provides numerous applications for bioengineering.

EXAMPLE 6

Identification and Characterization of Synthetic IRES Elements

This example demonstrates that translational regulatory elements, including IRES elements, can be identified by screening libraries of random oligonucleotides.

To identify other short sequences with properties similar to those of the 9 nucleotide Gtx IRES module (CCGGCGGGT; SEQ ID NO: 102), B104 cells were infected with two retroviral libraries that contained random sequences of 9 or 18 nucleotides in the intercistronic region. Cells expressing both cistrons were sorted and sequences recovered from selected cells were examined for IRES activity using a dual luciferase dicistronic mRNA. Two novel IRES elements were identified, each of which contained a sequence with complementarity to 18S rRNA. When multiple copies of either element were linked together, IRES activities were dramatically enhanced. Moreover, the synthetic IRESes were differentially active in various cell types. The similarity of these properties to those of the Gtx IRES module (SEQ ID NO: 102) provides confirmatory evidence that short nucleotide sequences can function as translational regulatory elements.

The MESVR/EGFP/ECFP/RSVPro retroviral vector (SEQ ID NO: 109; see Example 4) was used to generate two libraries. In the first library, an oligonucleotide containing 18 random nucleotides $(N)_{18}$ was cloned into the Mlu I site of the polylinker. The sequence of this oligonucleotide is: acgcgtgatcca$(N)_{18}$cgagcgacgcgt (SEQ ID NO: 103; see Edelman et al., supra, 2000). In the second library, an oligonucleotide containing two segments of 9 random nucleotides $(N)_9$ was cloned into the Pac I and Mlu I sites of the polylinker. The sequence of this oligonucleotide was ttaattaagaattcttctgacat$(a)_9$ttctgacat$(a)_9$ttctgacat$(a)_9(N)_9(a)_9(N')_9(a)_9$-gactcacaac-cccagaaacagacatacgcgt (SEQ ID NO: 104), where N and N' are different random nucleotide sequences. The design of this oligonucleotide was based on another previously described oligonucleotide $(S_{III}/S_{II})_5\beta$ (Chappell et al., supra, 2000). This oligonucleotide did not have IRES activity and was used as a spacer control. The first library consisted of about 2.5×$10^5$ bacterial clones and the second consisted of about 1.5×$10^5$ bacterial clones. As such; each library represented only a small fraction of the potential sequence complexity of the random oligonucleotides (about $6.9\times10^{10}$).

The retroviral libraries were packaged in COS1 cells. Sub-confluent cells were triply-transfected using the FuGENE 6 reagent (Roche Molecular Chemicals; Indianapolis Ind.) with plasmids encoding 1) the retroviral library, 2) MoMuLV gag and pol genes (PCMV-GP$_{(SaI)}$) and 3) the VSV G glycoprotein (see Tranque et al., supra, 1998). After 48 hr, retroviral particles were recovered from culture supernatant, filtered through a 0.45 μm membrane, and then used to infect B104 rat neural tumor cells (Bottenstein and Sato, Proc. Natl. Acad. Sci., USA 76:514-517, 1979).

Approximately $2\times10^6$ COS1 cells were transfected, and approximately the same number of B104 cells were subsequently infected. After 72 hr, cells were harvested and sorted by FACS on a FACSVantage SE (Becton Dickinson; San Jose Calif.). EGFP was excited with an argon laser tuned to 488 nm and fluorescence was recorded through a 530 nm bandpass filter. ECFP was excited with a krypton/argon laser tuned to 457 nm, and fluorescence was measured through a 495 nm bandpass filter. As controls for the FACS, B104 cells were infected with the following reference viruses: the parent vector (MESV/EGFP/ECFP/RSVPro), a virus encoding EGFP, a virus encoding ECFP, and a virus that contains the IRES from the encephalomyocarditis virus (EMCV) in the intercistronic region of the parent vector.

Cells co-expressing both EGFP and ECFP were isolated and returned to culture for 14 days. These cells were then resorted, and high co-expressors were isolated and further expanded in culture for 5 to 7 days. Genomic DNA was prepared using a QIA amp DNA miniprep kit (Qiagen). Intercistronic sequences were amplified by PCR using flanking primers, and cloned into the intercistronic region of RPh, which is a dicistronic vector that encodes Renilla luciferase protein as the first cistron and Photinus luciferase protein as the second cistron (Example 1). B104 cells were transiently co-transfected with the dual luciferase vector and with a vector expressing β-galactosidase, and luciferase and β-galactosidase assays were performed (see Example 1). Photinus luciferase activity values were normalized for transfection efficiency by means of β-galactosidase activity, and were then normalized to the activity of the RPh parent vector (first library) or of RPh containing the $(S_{III}/S_{II})_5\beta$ oligonucleotide as a spacer control (second library).

Sequences of the oligonucleotide inserts were determined using an ABI system sequencer (PE Biosystems, Foster City, Calif.), and were compared using the Clustal X multiple sequence alignment program (Thompson et al., Nucl. Acids Res. 25:4876-4882, 1997), and with the BestFit program from the Genetics Computer Group software package (Devereux et al., Nucl. Acids Res. 12:387-395, 1984). Sequence matches were evaluated by comparing BestFit quality scores to those obtained when the selected sequences were randomly shuffled 10 times and compared to 18S rRNA. Secondary structure predictions were made using mfold version 3.0 (Zuker et al., in "RNA Biochemistry and Biotechnology" (ed. Clark; Kluwer academic publishers 1999), pages 11-43; Mathews et al., J. Mol. Biol. 288:911-940, 1999). Northern blot analysis was performed as described in Example 1 using a riboprobe encompassing the entire coding region of the Photinus luciferase gene.

The retroviral library containing the random 18 nucleotide inserts was examined. This library, derived from $2.5\times10^5$ retroviral plasmids was used to infect approximately $2\times10^6$ rat B104 neural tumor cells. After 72 hr, cells that co-expressed both EGFP and ECFP, corresponding to approximately 0.5% of the cells, were isolated by FACS. These cells were cultured for 14 days, sorted again by FACS, and high co-expressors, corresponding to approximately 4% of cells, were collected and grown. The twice sorted cells were compared to cells that had been infected with the virus that contained the EMCV IRES between the EGFP and ECFP genes. Both cell populations showed variable expression suggesting that IRES activity can vary among individual cells, perhaps reflecting cell cycle differences in the population.

Intercistronic sequences contained within the population of twice sorted cells were isolated by genomic PCR, and cloned into the intercistronic polylinker of the RPh vector (see Example 1). This dual luciferase vector has a stable hairpin-forming sequence in the transcribed leader region upstream of the Renilla open reading frame. The hairpin structure blocks scanning ribosomes and therefore suppresses translation of the first cistron. Fifty clones were picked at random and plasmid DNA was prepared, sequenced, and transiently transfected into B104 cells. Of the 45 clones that were successfully sequenced, 39 contained unique 18 nucleotide inserts. The sequences of the other 6 clones were each represented more than once, which may reflect the relatively low complexity of selected sequences in these twice sorted cells.

The sequenced clones were tested in transfected cells and most activities were weak or at a background level. However, one sequence, designated intercistronic sequence 1-23 (ICS1-23; SEQ ID NO: 105) demonstrated enhanced *Photinus* luciferase activity approximately 8-fold greater than the control constructs. This level of activity was similar to that observed for one copy of the Gtx IRES module (Example 1).

Figure 4:
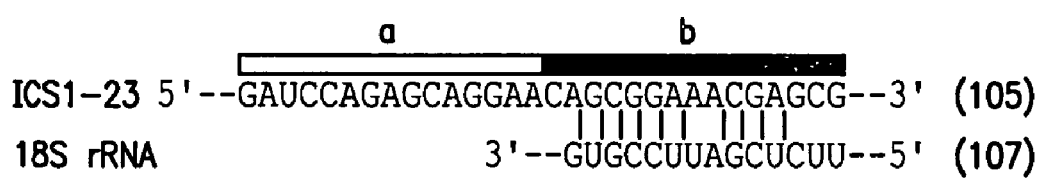
FIG. 4 shows the region of complementarity of the ICS1-23 sequence (SEQ ID NO: 105) and 18S rRNA (SEQ ID NO: 107). "a" and "b" indicate portions of the ICS1-23 sequence (SEQ ID NO: 105).

A sequence comparison between ICS1-23 (SEQ ID NO: 105) and 18S rRNA (SEQ ID NO: 107) revealed a complementary match between the 3' end of the IRES and 18S rRNA at nucleotides 1311-1324 (FIG. 4). This match has a BestFit quality score that is significantly greater than that obtained with 10 randomized variations of this sequence. To address whether the region of complementarity within ICS1-23 was associated with the IRES activity, the 30 nucleotide ICS1-23 sequence, which includes the 18 nucleotide random sequence together with 12 nucleotides of flanking sequence, was divided into two segments of 15 nucleotides each (see FIG. 4). The first 15 nucleotide segment lacked any complementarity to 18S rRNA, (ICS1-23a), while the second segment contained the complementary match to 18S rRNA (ICS1-23b; CAGCGGAAACGAGCG; SEQ ID NO: 106).

Multiple linked copies of the Gtx IRES module (SEQ ID NO: 102) had been shown to be more active than the corresponding monomer. Accordingly, multimers of each segment of ICS1-23 were synthesized, with each repeated segment separated by nine adenosine nucleotides (poly(A)$_9$). Although three linked copies of the ICS1-23a segment (see FIG. 4) did not enhance *Photinus* luciferase expression, constructs containing three and five linked copies of ICS1-23b (SEQ ID NO: 107) enhanced *Photinus* luciferase activity as compared to ICS1-23. These results indicate that the sequence of ICS1-23 that shares complementarity with 18S rRNA (i.e., SEQ ID NO: 106) has IRES activity. Northern blot analysis of RNA from cells expressing the five-linked copies of ICS1-23b (SEQ ID NO: 107) revealed a single hybridizing band corresponding in size to the full length dicistronic mRNA, thus confirming that ICS-23b did not enhance *Photinus* luciferase activity by other mechanisms such as alternative splicing or by functioning as a promoter.

The second retroviral library, which contained random 9 nucleotide segments separated by a poly(A)$_9$ spacer in the intercistronic region of the encoded dicistronic mRNA, was examined in order to identify smaller translational regulatory elements. Incorporation of the spacer sequence was based on the determination that 9 nucleotide Gtx IRES module (SEQ ID NO: 102), when present in multiple copies separated by the poly(A)$_9$ spacer, exhibited greater IRES activity than a single copy of the module.

Approximately 2×10$^6$ B104 cells were transduced with the second retroviral library, which was derived from 1.5×10$^5$ retroviral plasmids. Approximately 0.3% of the cells were selected by FACS, and cultured and sorted a second time. Approximately 3% of the latter cells were high co-expressors. The oligonucleotide inserts were recovered by genomic PCR and shotgun cloned into the intercistronic region of the RPh. One hundred clones were picked at random and 84 were successfully sequenced, yielding 37 different sequences. Fifteen of the sequences were represented two or more times, indicating that the complexity of the sequences represented in these twice sorted cells was somewhat lower than that of the first library. When tested by transient transfection in B104 cells, most sequences enhanced *Photinus* luciferase activity weakly (about 2-fold or less above background), and none were as active as ICS1-23 (SEQ ID NO: 105).

Six of the sequences, which were isolated four or more times from the twice sorted cells, were examined further. Each of these sequences contained two 9 nucleotide segments, which were tested individually as five linked copies. One of these constructs, containing a 9 nucleotide segment designated ICS2-17.2 (TCCGGTCGT; SEQ ID NO: 108), showed enhanced *Photinus* luciferase activity. In contrast to the five linked copies of ICS2-17.1, the other 9 nucleotide segment contained within selected sequence ICS2-17 did not have IRES activity. RNA analysis confirmed that a single transcript was produced from the construct, and that the increase in *Photinus* luciferase activity was derived from an intact dicistronic mRNA. These results indicate that ICS2-17.2 (SEQ ID NO: 108) functions as an IRES.

Five linked copies of both ICS1-23b (SEQ ID NO: 106) and ICS2-17.2 (SEQ ID NO: 108) also were examined using the 5' UTR of a monocistronic reporter mRNA. In 7 cell lines tested, (ICS1-23b)$_5$ blocked translation by approximately 70% and (ICS2-17.2)$_5$ slightly enhanced translation. In both cases, mRNA levels appeared to be unaffected. This result indicates that ICS1-23b (SEQ ID NO: 106) and ICS2-17.2 (SEQ ID NO: 108) function as IRES elements in the dicistronic mRNAs and not as transcriptional promoters or enhancers. As with ICS1-23b, sequence comparisons identified a complementary match between ICS2-17.2 and 18S rRNA with a BestFit quality score that is significantly greater than that obtained with 10 randomized variations of the this sequence.

The activity of the selected ICS1-23b (SEQ ID NO: 106) and ICS2-17.2 (SEQ ID NO: 108) IRES modules was examined in additional cell types other than the B1304 neuroblastoma cells. A construct of five linked copies of each module was active in each of the cells line tested, including rat glioma C6 cells, human neuroblastoma SK cells, mouse neuroblastoma N2a cells, mouse NIH-3T3 fibroblasts, human cervical carcinoma HeLa cells, normal rat kidney NRK cells, and mouse muscle myoblast C2C12 cells. The activities of these synthetic IRESes varied as much as ten-fold between cell lines, and also varied with respect to each other. However, the pattern of activity of the ICS-23b (SEQ ID NO: 106) module in the different cell lines tested was similar to that observed for ten-linked copies of the Gtx IRES module (SEQ ID NO: 102).

These results demonstrate that relatively small discrete nucleotide sequences can act as translational regulatory elements, including as IRES elements, which mediate cap-independent translation. Furthermore, the two IRES modules identified in this Example were selected from only a minute sampling of the total complexity of the random oligonucleotides. Thus, it is likely that screening a more complex library of random oligonucleotide will identify additional short nucleotide sequences having IRES or other translational regulatory activity.

It is remarkable that each of the short IRES element disclosed herein, including the Gtx IRES (SEQ ID NO: 102), the ICS1-23b IRES (SEQ ID NO: 106), and the ICS2-17.2 IRES (SEQ ID NO: 108) can promote internal initiation. Each of these three IRES modules contain a complementary match to different segments of 18S rRNA, suggesting that a direct interaction occurs between the IRES module and the 40S ribosomal subunit via base pairing to 18S rRNA. Alternatively, one or more of the IRES modules may recruits 40S ribosomal subunits by interacting with a protein component of the translational machinery, for example, a ribosomal protein, an initiation factor, or some other bridging protein. The ability to initiate translation internally by binding to an initiation factor has been reported, wherein an iron response element (IRE) and the bacteriophage λ transcriptional antiterminator box B element were both demonstrated to function as IRESes in the presence of fusion proteins between the appropriate binding protein for these RNA elements and eIF4G (DeGregorio et al., *EMBO J.* 18:4865-4874, 1999). However, the lack of appreciable sequence similarities between the IRES modules disclosed herein and cellular IRESes in general suggests that a wide variety of nucleotide sequences can function in internal translation initiation, and suggests that different sequences may recruit pre-initiation complexes by different mechanisms.

The observation that synthetic IRESes comprising multimers of ICS1-23b (SEQ ID NO: 106), ICS2-17.2 (SEQ ID NO: 108), or the Gtx (SEQ ID NO: 102) IRES module show enhanced IRES activity as compared to the corresponding monomers suggest that multiple copies of the IRES module may increase the probability of recruiting 40S ribosomal subunits. A similar observation has been made for eIF4G tethered to the IRE-binding protein, where there was an approximately linear increase in translation when the number of IRE binding sites was increased from one site to three (DeGregorio et al., supra, 1999).

An arresting feature of cellular IRESes, as well as of the disclosed IRES modules, is their variable potency in different cell types. As such, selection for IRESes in a variety of cell types can provide a means to identify additional elements having cell-specific and tissue-specific activities. If ribosomal recruitment requires direct interaction of IRESes with 18S rRNA, variations in efficiency may reflect differences in the accessibility of particular segments of 18S rRNA in different cell types. Alternatively, some IRES modules may require or be blocked by binding proteins that are differentially expressed in various cell types. Such possibilities can be distinguished by determining which proteins or components of the translation machinery bind to particular IRES sequences in various differentiated cells. In view of the modular nature of cellular IRES, combinations of synthetic IRESes can be constructed and elements having desirable regulatory actions can be selected. Such a combinatorial approach can be used to construct synthetic IRESes having variable translational regulatory activity, for example, highly restricted or widespread translational activity.

EXAMPLE 7

Design of IRES Modules Based on rRNA Structure

This example demonstrates that synthetic oligonucleotides having IRES activity can be designed based on the structure of ribosomal RNA molecules.

As disclosed herein, cellular IRESes exist as modular structures composed of short, independent oligonucleotides, including oligonucleotide that are complementary to 18S rRNA, and synthetic IRESes have been identified that also are complementary to rRNA oligonucleotide sequences. These results indicate that recruitment of ribosomal subunits by IRES modules is directed by base pairing of the IRES element to the rRNA within the ribosomal subunit.

The 9 nucleotide Gtx IRES module (SEQ ID NO: 102) is 100% complementary to an oligonucleotide sequence of 18S rRNA, and was tested as an IRES module based on this observation. In addition, the ability of the Gtx IRES module (SEQ ID NO: 102) to recruit 40S ribosomal subunits by base pairing to 18S rRNA was examined. Nitrocellulose filter-binding and electrophoretic mobility gel shift assays established a physical link between the 9 nucleotide Gtx IRES module (SEQ ID NO: 102) and dissociated ribosomal subunits, but not with other components of cell lysates. Transfection studies using dicistronic constructs that contained the Gtx IRES module (SEQ ID NO: 102) or mutants of this sequence demonstrated that internal initiation was maximal with a mutant module sharing 7 nucleotides of complementarity with 18S rRNA, and that as the degree of complementarity was progressively increased or decreased, IRES activity was decreased and, ultimately, lost. When tested in the 5' or 3' UTR of a monocistronic mRNA, sequences that enhanced internal initiation also functioned as translational enhancers. However, only those sequences with increased complementarity to 18S rRNA inhibited both internal initiation and translation in monocistronic mRNAs. This inhibition appeared to involve stable interactions between the mRNA and 40S ribosomal subunits as determined by polysome analysis. These results indicate that internal initiation of translation can occur at short nucleotide sequences by base pairing to 18S rRNA.

Figure 6A:
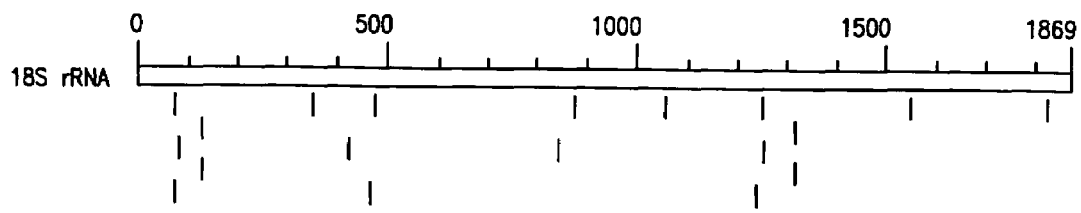
FIGS. 6A and 6B illustrate sites in which IRES modules of the invention share complementarity to mouse 18S ribosomal RNA (rRNA; SEQ ID NO: 196).
Figure 6B:
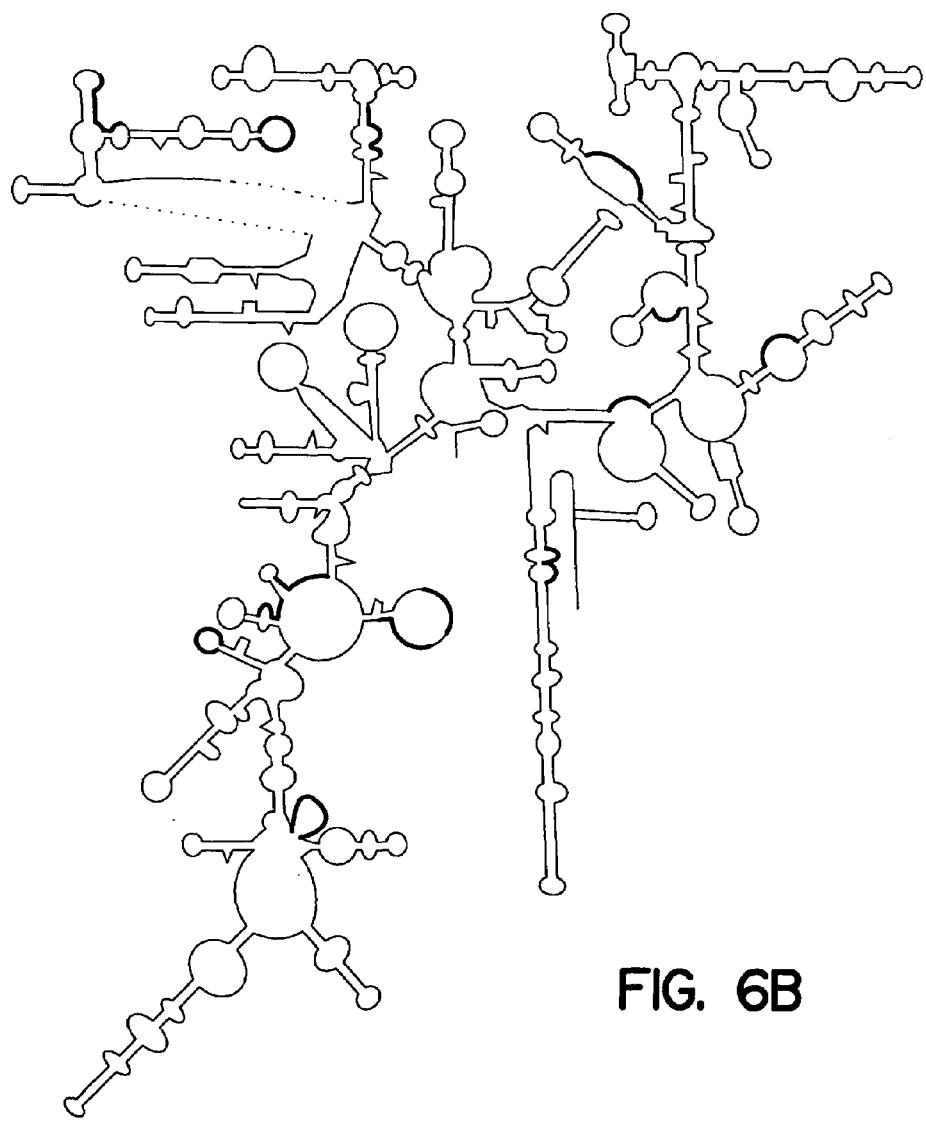

Sequence analysis of the IRES-modules recovered from the selection studies showed that most of the selected sequences contained complementary sequence matches of 8 to 9 nucleotides to different regions of the 18S rRNA (FIG. 6). Furthermore, many of the matches are to un-base paired regions of the rRNA (see FIG. 6B). Moreover, in some cases, several selected synthetic IRESes with slightly different sequences, were complementary to the same region of the 18S rRNA (see, also, Owens et al., 2001, which is incorporated herein by reference). These results indicate that synthetic translational regulatory elements can be designed based on rRNA sequences such as those set forth in SEQ ID NOS: 110-112, particularly to un-base paired rRNA sequences, which can be predicted using methods as disclosed herein, such that the synthetic translational regulatory elements are complementary to a selected rRNA target sequence. Methods of predicting secondary structure for rRNA are known in the art and include, for example, methods using the mfold version 3.0 software (Zuker et al., in "RNA Biochemistry and Biotechnology" (ed. Clark; Kluwer academic publishers 1999), pages 1'-43; Mathews et al., *J. Mol. Biol.* 288:911-940, 1999).

Although the invention has been described with reference to the above examples, it will be understood that modifications and variations are encompassed within the spirit and scope of the invention. Accordingly, the invention is limited only by the following claims.

What is claimed is:

1. An isolated transcriptional regulatory element selected from any of SEQ ID NOS: 40.

2. A recombinant nucleic acid molecule comprising a plurality of operatively linked isolated transcriptional regulatory elements of claim 1.

3. A kit, comprising an isolated transcriptional regulatory element according to claim 1.

4. The kit of claim 3, further comprising a vector for containing the regulatory element.

5. The kit of claim 3, comprising a plurality of isolated transcriptional regulatory elements.

* * * * *